(12) United States Patent
Park et al.

(10) Patent No.: US 6,455,677 B1
(45) Date of Patent: *Sep. 24, 2002

(54) FAPα-SPECIFIC ANTIBODY WITH IMPROVED PRODUCIBILITY

(75) Inventors: John Edward Park; Pilar Garin-Chesa, both of Biberach/Riss; Uwe Bamberger, Ochsenhausen; Wolfgang J. Rettig, Biberach/Riss, all of (DE); Olivier Lèger, Annemasse (FR); Jose William Saldanha, Middlesex (GB)

(73) Assignee: Boehringer Ingelheim International GmbH (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/301,593

(22) Filed: Apr. 29, 1999

Related U.S. Application Data

(60) Provisional application No. 60/086,049, filed on May 18, 1998.

(30) Foreign Application Priority Data

Apr. 30, 1998 (EP) .............................................. 98107925

(51) Int. Cl.$^7$ .............................................. C07K 16/30
(52) U.S. Cl. .............................. 530/388.85; 530/387.1; 530/391.3
(58) Field of Search .......................... 530/387.1, 387.3, 530/388.85, 388.8, 391.3; 424/130.1, 133.1, 155.1, 156.1, 181.1

(56) References Cited

U.S. PATENT DOCUMENTS

| | | |
|---|---|---|
| 5,059,523 A | 10/1991 | Rettig et al. |
| 5,693,761 A | 12/1997 | Queen et al. |

FOREIGN PATENT DOCUMENTS

| | | | |
|---|---|---|---|
| WO | WO 91/0996 | * | 7/1991 |
| WO | WO 93/05804 | | 4/1993 |
| WO | WO 94/05690 | | 3/1994 |
| WO | WO 97/08320 | | 3/1997 |
| WO | WO 97/34927 | | 9/1997 |
| WO | WO 97/41244 | | 11/1997 |

OTHER PUBLICATIONS

Axelsson, Acta Chemica Scandanavica Series B vol. 39:69–77, 1985.*
Lyons et al., Prot. Engineering 3:703–708, 1990.*
Walter et al., Proc. Natl. Acad. Sci. USA 77:5197–5200, 1980.*
Paulus et al., Behring Inst. Mitt 78:118–132, 1985.*
Rudikoff et al., Proc. Natl. Acad. Sci. USA 79:1979–1983, 1982.*
Panka et al., Proc. Natl. Acad. Sci. USA 85:3080–84, 1988.*
Amit et al., Science 233:747–753, 1986.*
Garin–Chesa, P. et al., "Cell surface glycoprotein of reactive stromal fibroblasts as a potential antibody target in human epithelial cancers", *Proc. Natl. Acad. Sci. USA* 87:7235–7239 (Sep. 1990).
Studnicka, G.M. et al., "Human–engineered monoclonal antibodies retain full specific binding activity by preserving non–CDR complementarity–modulating residues," *Protein Engin.* 7:805–814 (Jun. 1994).
Welt, S. et al., "Antibody Targeting in Metastatic Colon Cancer: A Phase I Study of Monoclonal Antibody F19 Against a Cell–Surface Protein of Reactive Tumor Stromal Fibroblasts," *J. Clin. Oncol.* 12:1193–1203 (Jun. 1994).
Wright, A. et al, "Genetically Engineered Antibodies: Progress and Prospects," *Crit. Rev. Immunol.* 12:125–168 (1992).
Partial European Search Report for European Application No. 98107925.4, mailed Jan. 15, 1999.

* cited by examiner

*Primary Examiner*—Sheela Huff
*Assistant Examiner*—Larry R. Helms
(74) *Attorney, Agent, or Firm*—Sterne, Kessler, Goldstei & Fox, P.L.L.C.

(57) ABSTRACT

Recombinant antibody proteins are provided that specifically bind fibroblast activation protein alpha (FAPα) and comprise framework modifications resulting in the improved producibility in host cells. The invention also relates to the use of said antibodies for diagnostic and therapeutic purposes and methods of producing said antibodies.

19 Claims, 49 Drawing Sheets

```
1          11         21         31         41
GACATTGTGA TGACCCAATC TCCAGACTCT TTGGCTGTGT CTCTAGGGGA
51         61         71         81         91
GAGGGCCACC ATCAACTGCA AGTCCAGTCA GAGCCTTTTA TATTCTAGAA
101        111        121        131        141
ATCAAAAGAA CTACTTGGCC TGGTATCAGC AGAAACCAGG ACAGCCACCC
151        161        171        181        191
AAACTCCTCA TCTTTTGGGC TAGCACTAGG GAATCTGGGG TACCTGATAG
201        211        221        231        241
GTTCAGTGGC AGTGGGTTTG GGACAGACTT CACCCTCACC ATTAGCAGCC
251        261        271        281        291
TGCAGGCTGA AGATGTGGCA GTTTATTACT GTCAGCAATA TTTTAGCTAT
301        311        321        331   339
CCGCTCACGT TCGGACAAGG GACCAAGGTG GAAATAAAA
```

FIG.1

```
1          11         21         31         41
DIVMTQSPDS LAVSLGERAT INCKSSQSLL YSRNQKNYLA WYQQKPGQPP
51         61         71         81         91
KLLIFWASTR ESGVPDRFSG SGFGTDFTLT ISSLQAEDVA VYYCQQYFSY
101        111
PLTFGQGTKV EIK
```

FIG.2

```
1          11         21         31         41
GACATTGTGA TGACCCAATC TCCAGACTCT TTGGCTGTGT CTCTAGGGGA
51         61         71         81         91
GAGGGCCACC ATCAACTGCA AGTCCAGTCA GAGCCTTTTA TATTCTAGAA
101        111        121        131        141
ATCAAAAGAA CTACTTGGCC TGGTTCCAGC AGAAACCAGG ACAGCCACCC
151        161        171        181        191
AAACTCCTCA TCTTTTGGGC TAGCACTAGG GAATCTGGGG TACCTGATAG
201        211        221        231        241
GTTCAGTGGC AGTGGGTTTG GGACAGACTT CACCCTCACC ATTAGCAGCC
251        261        271        281        291
TGCAGGCTGA AGATGTGGCA GTTTATGACT GTCAACAATA TTTTAGCTAT
301        311        321        331   339
CCGCTCACGT TCGGACAAGG GACCAAGGTG GAAATAAAA
```

FIG.3

```
1           11          21          31          41
DIVMTQSPDS  LAVSLGERAT  INCKSSQSLL  YSRNQKNYLA  WFQQKPGQPP
51          61          71          81          91
KLLIFWASTR  ESGVPDRFSG  SGFGTDFTLT  ISSLQAEDVA  VYDCQQYFSY
101         111
PLTFGQGTKV  EIK
```

FIG.4

```
1           11          21          31          41
GACATTGTGA  TGACCCAATC  TCCAGACTCT  TTGGCTGTGT  CTCTAGGGGA
51          61          71          81          91
GAGGGCCACC  ATCAACTGCA  AGTCCAGTCA  GAGCCTTTTA  TATTCTAGAA
101         111         121         131         141
ATCAAAAGAA  CTACTTGGCC  TGGTATCAGC  AGAAACCAGG  ACAGCCACCC
151         161         171         181         191
AAACTCCTCA  TCTATTGGGC  TAGCACTAGG  GAATCTGGGG  TACCTGATAG
201         211         221         231         241
GTTCAGTGGC  AGTGGGTTTG  GGACAGACTT  CACCCTCACC  ATTAGCAGCC
251         261         271         281         291
TGCAGGCTGA  AGATGTGGCA  GTTTATTACT  GTCAGCAATA  TTTTAGCTAT
301         311         321         331    339
CCGCTCACGT  TCGGACAAGG  GACCAAGGTG  GAAATAAAA
```

FIG.5

```
1           11          21          31          41
DIVMTQSPDS  LAVSLGERAT  INCKSSQSLL  YSRNQKNYLA  WYQQKPGQPP
51          61          71          81          91
KLLIYWASTR  ESGVPDRFSG  SGFGTDFTLT  ISSLQAEDVA  VYYCQQYFSY
101         111
PLTFGQGTKV  EIK
```

FIG.6

```
1
CAGGTGCAAC TAGTGCAGTC CGGCGCCGAA GTGAAGAAAC CCGGTGCTTC
51
CGTGAAAGTC AGCTGTAAAA CTAGTAGATA CACCTTCACT GAATACACCA
101
TACACTGGGT TAGACAGGCC CCTGGCCAAA GGCTGGAGTG GATAGGAGGT
151
ATTAATCCTA ACAATGGTAT TCCTAACTAC AACCAGAAGT TCAAGGGCCG
201
GGCCACCTTG ACCGTAGGCA AGTCTGCCAG CACCGCCTAC ATGGAACTGT
251
CCAGCCTGCG CTCCGAGGAC ACTGCAGTCT ACTACTGCGC CAGAAGAAGA
301
ATCGCCTATG GTTACGACGA GGGCCATGCT ATGGACTACT GGGGTCAAGG
351                    372
AACCCTTGTC ACCGTCTCCT CA
```

FIG.7

```
1          11         21         31         41
QVQLVQSGAE VKKPGASVKV SCKTSRYTFT EYTIHWVRQA PGQRLEWIGG
51         61         71         81         91
INPNNGIPNY NQKFKGRATL TVGKSASTAY MELSSLRSED TAVYYCARRR
101        111        121-124
IAYGYDEGHA MDYWGQGTLV TVSS
```

FIG.8

```
1
CAGGTGCAAC TAGTGCAGTC CGGCGCCGAA GTGAAGAAAC CCGGTGCTTC
51
CGTGAAAGTC AGCTGTAAAA CTAGTAGATA CACCTTCACT GAATACACCA
101
TACACTGGGT TAGACAGGCC CCTGGCCAAA GGCTGGAGTG GATAGGAGGT
151
ATTAATCCTA ACAATGGTAT TCCTAACTAC AACCAGAAGT TCAAGGGCCG
201
GGCCACCTTG ACCGTAGGCA AGTCTGCCAG CACCGCCTAC ATGGAACTGT
251
CCAGCCTGCG CTCCGAGGAC ACTGCAGTCT ACTTCTGCGC CAGAAGAAGA
301
ATCGCCTATG GTTACGACGA GGGCCATGCT ATGGACTACT GGGGTCAAGG
351                    372
AACCCTTGTC ACCGTCTCCT CA
```

FIG.9

```
1          11         21         31         41
QVQLVQSGAE VKKPGASVKV SCKTSRYTFT EYTIHWVRQA PGQRLEWIGG
51         61         71         81         91
INPNNGIPNY NQKFKGRATL TVGKSASTAY MELSSLRSED TAVYFCARRR
101        111        121-124
IAYGYDEGHA MDYWGQGTLV TVSS
```

FIG.10

```
1
CAGGTGCAAC TAGTGCAGTC CGGCGCCGAA GTGAAGAAAC CCGGTGCTTC
51
CGTGAAAGTC AGCTGTAAAA CTAGTAGATA CACCTTCACT GAATACACCA
101
TACACTGGGT TAGACAGGCC CCTGGCCAAA GGCTGGAGTG GATAGGAGGT
151
ATTAATCCTA ACAATGGTAT TCCTAACTAC AACCAGAAGT TCAAGGGCCG
201
GGTCACCATC ACCGTAGACA CCTCTGCCAG CACCGCCTAC ATGGAACTGT
251
CCAGCCTGCG CTCCGAGGAC ACTGCAGTCT ACTACTGCGC CAGAAGAAGA
301
ATCGCCTATG GTTACGACGA GGGCCATGCT ATGGACTACT GGGGTCAAGG
351                   372
AACCCTTGTC ACCGTCTCCT CA
```

FIG.11

```
1          11         21         31         41
QVQLVQSGAE VKKPGASVKV SCKTSRYTFT EYTIHWVRQA PGQRLEWIGG
51         61         71         81         91
INPNNGIPNY NQKFKGRVTI TVDTSASTAY MELSSLRSED TAVYYCARRR
101        111        121-124
IAYGYDEGHA MDYWGQGTLV TVSS
```

FIG.12

```
1
CAGGTGCAAC TAGTGCAGTC CGGCGCCGAA GTGAAGAAAC CCGGTGCTTC
51
CGTGAAAGTC AGCTGTAAAA CTAGTAGATA CACCTTCACT GAATACACCA
101
TACACTGGGT TAGACAGGCC CCTGGCCAAA GGCTGGAGTG GATAGGAGGT
151
ATTAATCCTA ACAATGGTAT TCCTAACTAC AACCAGAAGT TCAAGGGCCG
201
GGTCACCATC ACCGTAGACA CCTCTGCCAG CACCGCCTAC ATGGAACTGT
251
CCAGCCTGCG CTCCGAGGAC ACTGCAGTCT ACTTCTGCGC CAGAAGAAGA
301
ATCGCCTATG GTTACGACGA GGGCCATGCT ATGGACTACT GGGGTCAAGG
351                   372
AACCCTTGTC ACCGTCTCCT CA
```

FIG.13

```
1          11         21         31         41
QVQLVQSGAE VKKPGASVKV SCKTSRYTFT EYTIHWVRQA PGQRLEWIGG
51         61         71         81         91
INPNNGIPNY NQKFKGRVTI TVDTSASTAY MELSSLRSED TAVYFCARRR
101        111        121-124
IAYGYDEGHA MDYWGQGTLV TVSS
```

FIG.14

```
1
CAGGTGCAAC TAGTGCAGTC CGGCGCCGAA GTGAAGAAAC CCGGTGCTTC
51
CGTGAAAGTC AGCTGTAAAA CTAGTGGATA CACCTTCACT GAATACACCA
101
TACACTGGGT TAGACAGGCC CCTGGCCAAA GGCTGGAGTG GATAGGAGGT
151
ATTAATCCTA ACAATGGTAT TCCTAACTAC AACCAGAAGT TCAAGGGCCG
201
GGTCACCATC ACCGTAGACA CCTCTGCCAG CACCGCCTAC ATGGAACTGT
251
CCAGCCTGCG CTCCGAGGAC ACTGCAGTCT ACTACTGCGC CAGAAGAAGA
301
ATCGCCTATG GTTACGACGA GGGCCATGCT ATGGACTACT GGGGTCAAGG
351                   372
AACCCTTGTC ACCGTCTCCT CA
```

FIG.15

```
1          11         21         31         41
QVQLVQSGAE VKKPGASVKV SCKTSGYTFT EYTIHWVRQA PGQRLEWIGG
51         61         71         81         91
INPNNGIPNY NQKFKGRVTI TVDTSASTAY MELSSLRSED TAVYYCARRR
101        111        121-124
IAYGYDEGHA MDYWGQGTLV TVSS
```

FIG.16

```
1
DIVMSQSPSS LAVSVGEKVT MSCKSSQSLL YSRNQKNYLA WFQQKPGQSP
51
KLLIFWASTR ESGVPDRFTG SGFGTDFNLT ISSVQAEDLA VYDCQQYFSY
101
PLTFGAGTKL ELKRTVAAPS VFIFPPSDEQ LKSGTASVVC LLNNFYPREA
151
KVQWKVDNAL QSGNSQESVT EQDSKDSTYS LSSTLTLSKA DYEKHKVYAC
201
EVTHQGLSSP VTKSFNRGEC
```

FIG.17

```
1
VQLQQSGPEL VKPGASVKMS CKTSRYTFTE YTIHWVRQSH GKSLEWIGGI
51
NPNNGIPNYN QKFKGRATLT VGKSSSTAYM ELRSLTSEDS AVYFCARRRI
101
AYGYDEGHAM DYWGQGTSVT VSSASTKGPS VFPLAPSSKS TSGGTAALGC
151
LVKDYFPEPV TVSWNSGALT SGVHTFPAVL QSSGLYSLSS VVTVPSSSLG
201
TQTYICNVNH KPSNTKVDKK VEPKSCDKTH TCPPCPAPEL LGGPSVFLFP
251
PKPKDTLMIS RTPEVTCVVV DVSHEDPEVK FNWYVDGVEV HNAKTKPREE
301
QYNSTYRVVS VLTVLHQDWL NGKEYKCKVS NKALPAPIEK TISKAKGQPR
351
EPQVYTLPPS REEMTKNQVS LTCLVKGFYP SDIAVEWESN GQPENNYKTT
401
PPVLDSDGSF FLYSKLTVDK SRWQQGNVFS CSVMHEALHN HYTQKSLSLS
451
PGK
```

FIG.18

```
340        350        360        370        380
CGTACTGTGG CTGCACCATC TGTCTTCATC TTCCCGCCAT CTGATGAGCA
390        400        410        420        430
GTTGAAATCT GGAACTGCCT CTGTTGTGTG CCTGCTGAAT AACTTCTATC
440        450        460        470        480
CCAGAGAGGC CAAAGTACAG TGGAAGGTGG ATAACGCCCT CCAATCGGGT
490        500        510        520        530
AACTCCCAGG AGAGTGTCAC AGAGCAGGAC AGCAAGGACA GCACCTACAG
540        550        560        570        580
CCTCAGCAGC ACCCTGACGC TGAGCAAAGC AGACTACGAG AAACACAAAG
590        600        610        620        630
TCTACGCCTG CGAAGTCACC CATCAGGGCC TGAGCTCGCC CGTCACAAAG
640        650        660
AGCTTCAACA GGGGAGAGTGT
```

FIG.19

```
114        124        134        144        154
RTVAAPSVFI FPPSDEQLKS GTASVVCLLN NFYPREAKVQ WKVDNALQSG
164        174        184        194        204
NSQESVTEQD SKDSTYSLSS TLTLSKADYE KHKVYACEVT HQGLSSPVTK
214-220
SFNRGEC
```

FIG.20

```
373
GCCTCCACCA AGGGCCCATC GGTCTTCCCC CTGGCACCCT CCTCCAAGAG
423
CACCTCTGGG GGCACAGCGG CCCTGGGCTG CCTGGTCAAG GACTACTTCC
473
CCGAACCGGT GACGGTGTCG TGGAACTCAG GCGCCCTGAC CAGCGGCGTG
523
CACACCTTCC CGGCTGTCCT ACAGTCCTCA GGACTCTACT CCCTCAGCAG
573
CGTGGTGACC GTGCCCTCCA GCAGCTTGGG CACCCAGACC TACATCTGCA
623
ACGTGAATCA CAAGCCCAGC AACACCAAGG TGGACAAGAA AGTTGAGCCC
673
AAATCTTGTG ACAAAACTCA CACATGCCCA CCGTGCCCAG CACCTGAACT
723
CCTGGGGGGA CCGTCAGTCT TCCTCTTCCC CCCAAAACCC AAGGACACCC
773
TCATGATCTC CCGGACCCCT GAGGTCACAT GCGTGGTGGT GGACGTGAGC
823
```

FIG.21A

```
CACGAAGACC CTGAGGTCAA GTTCAACTGG TACGTGGACG GCGTGGAGGT
873
GCATAATGCC AAGACAAAGC CGCGGGAGGA GCAGTACAAC AGCACGTACC
923
GGGTGGTCAG CGTCCTCACC GTCCTGCACC AGGACTGGCT GAATGGCAAG
973
GAGTACAAGT GCAAGGTCTC CAACAAAGCC CTCCCAGCCC CCATCGAGAA
1023
AACCATCTCC AAAGCCAAAG GGCAGCCCCG AGAACCACAG GTGTACACCC
1073
TGCCCCCATC CCGGGAGGAG ATGACCAAGA ACCAGGTCAG CCTGACCTGC
1123
CTGGTCAAAG GCTTCTATCC CAGCGACATC GCCGTGGAGT GGGAGAGCAA
1173
TGGGCAGCCG GAGAACAACT ACAAGACCAC GCCTCCCGTG CTGGACTCCG
1223
ACGGCTCCTT CTTCCTCTAC AGCAAGCTCA CCGTGGACAA GAGCAGGTGG
1273
CAGCAGGGGA ACGTCTTCTC ATGCTCCGTG ATGCATGAGG CTCTGCACAA
1323                                           1362
CCACTACACG CAGAAGAGCC TCTCCCTGTC TCCGGGTAAA
```

FIG.21B

```
                                                       125
ASTKGPSVFP LAPSSKSTSG GTAALGCLVK DYFPEPVTVS WNSGALTSGV
                                                       175
HTFPAVLQSS GLYSLSSVVT VPSSSLGTQT YICNVNHKPS NTKVDKKVEP
                                                       225
KSCDKTHTCP PCPAPELLGG PSVFLFPPKP KDTLMISRTP EVTCVVVDVS
                                                       275
HEDPEVKFNW YVDGVEVHNA KTKPREEQYN STYRVVSVLT VLHQDWLNGK
                                                       325
EYKCKVSNKA LPAPIEKTIS KAKGQPREPQ VYTLPPSREE MTKNQVSLTC
                                                       375
LVKGFYPSDI AVEWESNGQP ENNYKTTPPV LDSDGSFFLY SKLTVDKSRW
425                           454
QQGNVFSCSV MHEALHNHYT QKSLSLSPGK
```

FIG.22

HindIII
```
       aagcttGCCGCCACCatggattcacaggcccaggttcttatgttactgccgctatgggta
  1    ----------+---------+---------+---------+---------+---------+
       ttcgaaCGGCGGTGGtacctaagtgtccgggtccaagaatacaatgacggcgatacccat
         Kozak sequence
                         M  D  S  Q  A  Q  V  L  M  L  L  P  L  W  V tctggtacctgtggggacattgtgatgtcacagtctccatcctccctagctgtgtcagtt
  61   ----------+---------+---------+---------+---------+---------+
       agaccatggacaccctgtaacactacagtgtcagaggtaggagggatcgacacagtcaa
        S  G  T  C  G  D  I  V  M  S  Q  S  P  S  S  L  A  V  S  V ggagagaaggttactatgagctgcaagtccagtcagagcctttatatagtcgtaatcaa
  121  ----------+---------+---------+---------+---------+---------+
       cctctcttccaatgatactcgacgttcaggtcagtctcggaaaatatatcagcattagtt
        G  E  K  V  T  M  S  C  K  S  S  Q  S  L  L  Y  S  R  N  Q
                                  ‾‾‾‾‾‾‾‾‾‾‾‾‾‾‾‾‾‾‾‾‾‾‾‾‾‾‾‾‾‾
                                              CDR 1 aagaactacttggcctggttccagcagaagccagggcagtctcctaaactgctgattttc
  181  ----------+---------+---------+---------+---------+---------+
       ttcttgatgaaccggaccaaggtcgtcttcggtcccgtcagaggatttgacgactaaaag
        K  N  Y  L  A  W  F  Q  Q  K  P  G  Q  S  P  K  L  L  I  F
       ‾‾‾‾‾‾‾‾‾‾‾‾‾‾ tgggcatccactagggaatctggggtccctgatcgcttcacaggcagtggatttgggacg
  241  ----------+---------+---------+---------+---------+---------+
       acccgtaggtgatcccttagaccccagggactagcgaagtgtccgtcacctaaaccctgc
        W  A  S  T  R  E  S  G  V  P  D  R  F  T  G  S  G  F  G  T
        ‾‾‾‾‾‾‾‾‾‾‾‾‾‾‾‾
              CDR 2 gatttcaatctcaccatcagcagtgtgcaggctgaggacctggcagtttatgactgtcag
  301  ----------+---------+---------+---------+---------+---------+
       ctaaagttagagtggtagtcgtcacacgtccgactcctggaccgtcaaatactgacagtc
        D  F  N  L  T  I  S  S  V  Q  A  E  D  L  A  V  Y  D  C  Q
                                                                 ‾ caatattttagctatccgctcacgttcggtgctgggaccaagctggagctgaAACGTGAG
  361  ----------+---------+---------+---------+---------+---------+
       gttataaaatcgataggcgagtgcaagccacgaccctggttcgacctcgactTTGCACTG
                                                              splice donor site
        Q  Y  F  S  Y  P  L  T  F  G  A  G  T  K  L  E  L  K
       ‾‾‾‾‾‾‾‾‾‾‾‾‾‾‾‾‾‾‾‾‾‾‾‾
              CDR 3

BamHI
       Tggatcc
  421  ------- 427
       Acctagg
```

FIG.24

```
         HindIII
         AAGCTTGCCGCCACCATGGGATGGAGCTGGGTCTTTCTCTTTCTCCTGTCAGGAACTGCA
      1  ----------+----------+----------+----------+----------+----------+
         TTCGAACGGCGGTGGTACCCTACCTCGACCCAGAAAGAGAAAGAGGACAGTCCTTGACGT
             Kozak sequence
                     M  G  W  S  W  V  F  L  F  L  L  S  G  T  A GGTGTCCTCTCTGAGGTCCAGCTGCAACAGTCTGGACCTGAGCTGGTGAAGCCTGGGGCT
     61  ----------+----------+----------+----------+----------+----------+
         CCACAGGAGAGACTCCAGGTCGACGTTGTCAGACCTGGACTCGACCACTTCGGACCCCGA

G  V  L  S  E  V  Q  L  Q  Q  S  G  P  E  L  V  K  P  G  A

TCAGTAAAGATGTCCTGCAAGACTTCTAGATACACATTCACTGAATACACCATACACTGG
    121  ----------+----------+----------+----------+----------+----------+
         AGTCATTTCTACAGGACGTTCTGAAGATCTATGTGTAAGTGACTTATGTGGTATGTGACC

S  V  K  M  S  C  K  T  S  R  Y  T  F  T  E  Y  T  I  H  W
                                                    CDR 1

GTGAGACAGAGCCATGGAAAGAGCCTTGAGTGGATTGGAGGTATTAATCCTAACAATGGT
    181  ----------+----------+----------+----------+----------+----------+
         CACTCTGTCTCGGTACCTTTCTCGGAACTCACCTAACCTCCATAATTAGGATTGTTACCA

V  R  Q  S  H  G  K  S  L  E  W  I  G  G  I  N  P  N  N  G
                                                    CDR 2

ATTCCTAACTACAACCAGAAGTTCAAGGGCAGGGCCACATTGACTGTAGGCAAGTCCTCC
    241  ----------+----------+----------+----------+----------+----------+
         TAAGGATTGATGTTGGTCTTCAAGTTCCCGTCCCGGTGTAACTGACATCCGTTCAGGAGG

I  P  N  Y  N  Q  K  F  K  G  R  A  T  L  T  V  G  K  S  S

AGCACCGCCTACATGGAGCTCCGCAGCCTGACATCTGAGGATTCTGCGGTCTATTTCTGT
    301  ----------+----------+----------+----------+----------+----------+
         TCGTGGCGGATGTACCTCGAGGCGTCGGACTGTAGACTCCTAAGACGCCAGATAAAGACA

```
     GCAAGAAGAAGAATCGCCTATGGTTACGACGAGGGCCATGCTATGGACTACTGGGGTCAA
361  ----------+----------+----------+----------+----------+----------+
     CGTTCTTCTTCTTAGCGGATACCAATGCTGCTCCCGGTACGATACCTGATGACCCCAGTT

A  R   R  R  I  A  Y  G  Y  D  E  G  H  A  M  D  Y   W  G  Q
                              CDR 3
                                                    BamHI
     GGAACCTCAGTCACCGTCTCCTCAGGTGAGTGGATCC
421  ----------+----------+----------+-------- 468
     CCTTGGAGTCAGTGGCAGAGGAGTCCACTCACCTAGG
                            splice donor site
      G  T  S  V  T  V  S  S
```

FIG.25B

```
                             Spe I
  1  gaattccagc acactggcgg ccgttACTAG TTATTAATAG TAATCAATTA

51  CGGGGTCATT AGTTCATAGC CCATATATGG AGTTCCGCGT TACATAACTT

101  ACGGTAAATG GCCCGCCTGG CTGACCGCCC AACGACCCCC GCCCATTGAC

151  GTCAATAATG ACGTATGTTC CCATAGTAAC GCCAATAGGG ACTTTCCATT

201  GACGTCAATG GGTGGAGTAT TTACGGTAAA CTGCCCACTT GGCAGTACAT

251  CAAGTGTATC ATATGCCAAG TACGCCCCCT ATTGACGTCA ATGACGGTAA

301  ATGGCCCGCC TGGCATTATG CCCAGTACAT GACCTTATGG GACTTTCCTA
                   SnaB I
351  CTTGGCAGTA CATCTACGTA TTAGTCATCG CTATTACCAT GGTGATGCGG

401  TTTTGGCAGT ACATCAATGG GCGTGGATAG CGGTTTGACT CACGGGGATT

451  TCCAAGTCTC CACCCCATTG ACGTCAATGG GAGTTTGTTT TGGCACCAAA

501  ATCAACGGGA CTTTCCAAAA TGTCGTAACA ACTCCGCCCC ATTGACGCAA

551  ATGGGCGGTA GGCGTGTACG GTGGGAGGTC TATATAAGCA GAGCTCGTTT

601  AGTGAACCGT CAGATCGCCT GGAGACGCCA TCCACGCTGT TTTGACCTCC
                                                 Sac II
651  ATAGAAGACA CCGGGACCGA TCCAGCCTCC GCGGCCGGGA ACGGTGCATT

701  GGAACGCGGA TTCCCCGTGC CAAGAGTGAC GTAAGTACCG CCTATAGAGT
```

FIG.26A

```
 751  CTATAGGCCC ACCCCCTTGG CTTCTTATGC ATGCTATACT GTTTTTGGCT

801  TGGGGTCTAT ACACCCCCGC TTCCTCATGT TATAGGTGAT GGTATAGCTT

851  AGCCTATAGG TGTGGGTTAT TGACCATTAT TGACCACTCC CCTATTGGTG

901  ACGATACTTT CCATTACTAA TCCATAACAT GGCTCTTTGC CACAACTCTC

951  TTTATTGGCT ATATGCCAAT ACACTGTCCT TCAGAGACTG ACACGGACTC

1001  TGTATTTTTA CAGGATGGGG TCTCATTTAT TATTTACAAA TTCACATATA

1051  CAACACCACC GTCCCCAGTG CCCGCAGTTT TTATTAAACA TAACGTGGGA
                                          BspE I
1101  TCTCCACGCG AATCTCGGGT ACGTGTTCCG GACATGGGCT CTTCTCCGGT

1151  AGCGGCGGAG CTTCTACATC CGAGCCCTGC TCCCATGCCT CCAGCGACTC

1201  ATGGTCGCTC GGCAGCTCCT TGCTCCTAAC AGTGGAGGCC AGACTTAGGC

1251  ACAGCACGAT GCCCACCACC ACCAGTGTGC CGCACAAGGC CGTGGCGGTA

1301  GGGTATGTGT CTGAAAATGA GCTCggggag cgggcttgca ccgctgacgc
                      Afl II
1351  atttggaaga cttaaggcag cggcagaaga agatgcaggc agctgagttg 1401  ttgtgttctg ataagagtca gaggtaactc cgttgcggt gctgttaacg 1451  gtggagggca gtgtagtctg agcagtactc gttgctgccg cgcgcgccac 1501  cagacataat agctgacaga ctaacagact gttcctttcc atgggtcttt
                                    Mlu I           Hind III
1551  tctgcagtca ccgtccttga cacgcgtctc gggaagcttG CCGCCACCAT
                                                          M
                                                          Kpn I
1601  GGATTCACAG GCCCAGGTTC TTATGTTACT GCCGCTATGG GTATCTGGTA
       D  S  Q    A  Q  V   L  M  L  L   P  L  W   V  S  G
1651  CCTGTGGGGA CATTGTGATG TCACAGTCTC CATCCTCCCT AGCTGTGTCA
       T  C  G   D  I  V  M   S  Q  S   P  S  S  L   A  V  S
1701  GTTGGAGAGA AGGTTACTAT GAGCTGCAAG TCCAGTCAGA GCCTTTTATA
       V  G  E   K  V  T  M   S  C  K   S  S  Q   S  L  L  Y
       XbaI                              CDR 1
1751  TTCTAGAAAT CAAAAGAACT ACTTGGCCTG GTTCCAGCAG AAGCCAGGGC
       S  R  N    Q  K  N   Y  L  A   W  F  Q  Q    K  P  G
1801  AGTCTCCTAA ACTGCTGATT TTCTGGGCAT CCACTAGGGA ATCTGGGGTC
       Q  S  P  K   L  L  I   F  W  A    S  T  R  E   S   G  V
                                            CDR 2
```

FIG. 26B

```
1851  CCTGATCGCT  TCACAGGCAG  TGGATTTGGG  ACGGATTTCA  ATCTCACCAT
        P  D  R    F  T  G  S    G  F  G    T  D  F    N  L  T  I

1901  CAGCAGTGTG  CAGGCTGAGG  ACCTGGCAGT  TTATGACTGT  CAGCAATATT
        S  S  V    Q  A  E    D  L  A  V    Y  D  C    Q  Q  Y

1951  TTAGCTATCC  GCTCACGTTC  GGTGCTGGGA  CCAAGCTGGA  GCTGAAACGT
       F  S  Y  P    L  T  F    G  A  G    T  K  L  E    L  K  R
              CDR 3
           BamH I
2001  GAGTggatcc  ATCTGGGATA  AGCATGCTGT  TTTCTGTCTG  TCCCTAACAT

2051  GCCCTGTGAT  TATGCGCAAA  CAACACACCC  AAGGGCAGAA  CTTTGTTACT

2101  TAAACACCAT  CCTGTTTGCT  TCTTTCCTCA  GGAACTGTGG  CTGCACCATC
                                                  T  V    A  A  P  S
2151  TGTCTTCATC  TTCCCGCCAT  CTGATGAGCA  GTTGAAATCT  GGAACTGCCT
        V  F  I    F  P  P    S  D  E  Q    L  K  S    G  T  A
2201  CTGTTGTGTG  CCTGCTGAAT  AACTTCTATC  CAGAGAGGC  CAAAGTACAG
        S  V  V  C    L  L  N    N  F  Y    P  R  E  A    K  V  Q
2251  TGGAAGGTGG  ATAACGCCCT  CCAATCGGGT  AACTCCCAGG  AGAGTGTCAC
        W  K  V    D  N  A  L    Q  S  G    N  S  Q    E  S  V  T
2301  AGAGCAGGAC  AGCAAGGACA  GCACCTACAG  CCTCAGCAGC  ACCCTGACGC
        E  Q  D    S  K  D    S  T  Y  S    L  S  S    T  L  T
2351  TGAGCAAAGC  AGACTACGAG  AAACACAAAG  TCTACGCCTG  CGAAGTCACC
        L  S  K  A    D  Y  E    K  H  K    V  Y  A  C    E  V  T
2401  CATCAGGGCC  TGAGCTCGCC  CGTCACAAAG  AGCTTCAACA  GGGGAGAGTG
        H  Q  G    L  S  S  P    V  T  K    S  F  N    R  G  E  C
2451  TTAGAGGGAG  AAGTGCCCCC  ACCTGCTCCT  CAGTTCCAGC  CTGACCCCCT
          *
2501  CCCATCCTTT  GGCCTCTGAC  CCTTTTTCCA  CAGGGGACCT  ACCCCTATTG

2551  CGGTCCTCCA  GCTCATCTTT  CACCTCACCC  CCCTCCTCCT  CCTTGGCTTT

2601  AATTATGCTA  ATGTTGGAGG  AGAATGAATA  AATAAAGTGA  ATCTTTGCAC

2651  CTGTGGTGGA  TCTAATAAAA  GATATTTATT  TTCATTAGAT  ATGTGTGTTG

2701  GTTTTTTGTG  TGCAGTGCCT  CTATCTGGAG  GCCAGGTAGG  GCTGGCCTTG

2751  GGGGAGGGGG  AGGCCAGAAT  GACTCCAAGA  GCTACAGGAA  GGCAGGTCAG

2801  AGACCCCACT  GGACAAACAG  TGGCTGGACT  CTGCACCATA  ACACACAATC

2851  AACAGGGGAG  TGAGCTGGAA  ATTTGCTAGC  GAATTCTTGA  AGACGAAAGG

2901  GCCTCGTGAT  ACGCCTATTT  TTATAGGTTA  ATGTCATGAT  AATAATGGTT
```

FIG.26C

```
2951 TCTTAGACGT CAGGTGGCAC TTTTCGGGGA AATGTGCGCG GAACCCCTAT

3001 TTGTTTATTT TTCTAAATAC ATTCAAATAT GTATCCGCTC ATGAGACAAT

3051 AACCCTGATA AATGCTTCAA TAATATTGAA AAAGGAAGAG TATGAGTATT

3101 CAACATTTCC GTGTCGCCCT TATTCCCTTT TTTGCGGCAT TTTGCCTTCC

3151 TGTTTTTGCT CACCCAGAAA CGCTGGTGAA AGTAAAAGAT GCTGAAGATC

3201 AGTTGGGTGC ACGAGTGGGT TACATCGAAC TGGATCTCAA CAGCGGTAAG

3251 ATCCTTGAGA GTTTTCGCCC CGAAGAACGT TTTCCAATGA TGAGCACTTT

3301 TAAAGTTCTG CTATGTGGCG CGGTATTATC CCGTGTTGAC GCCGGGCAAG

3351 AGCAACTCGG TCGCCGCATA CACTATTCTC AGAATGACTT GGTTGAGTAC

3401 TCACCAGTCA CAGAAAAGCA TCTTACGGAT GGCATGACAG TAAGAGAATT

3451 ATGCAGTGCT GCCATAACCA TGAGTGATAA CACTGCGGCC AACTTACTTC
                Pvu I
3501 TGACAACGAT CGGAGGACCG AAGGAGCTAA CCGCTTTTTT GCACAACATG

3551 GGGGATCATG TAACTCGCCT TGATCGTTGG GAACCGGAGC TGAATGAAGC

3601 CATACCAAAC GACGAGCGTG ACACCACGAT GCCTGCAGCA ATGGCAACAA

3651 CGTTGCGCAA ACTATTAACT GGCGAACTAC TTACTCTAGC TTCCCGGCAA

3701 CAATTAATAG ACTGGATGGA GGCGGATAAA GTTGCAGGAC CACTTCTGCG

3751 CTCGGCCCTT CCGGCTGGCT GGTTTATTGC TGATAAATCT GGAGCCGGTG

3801 AGCGTGGGTC TCGCGGTATC ATTGCAGCAC TGGGGCCAGA TGGTAAGCCC

3851 TCCCGTATCG TAGTTATCTA CACGACGGGG AGTCAGGCAA CTATGGATGA

3901 ACGAAATAGA CAGATCGCTG AGATAGGTGC CTCACTGATT AAGCATTGGT

3951 AACTGTCAGA CCAAGTTTAC TCATATATAC TTTAGATTGA TTTAAAACTT

4001 CATTTTTAAT TTAAAAGGAT CTAGGTGAAG ATCCTTTTTG ATAATCTCAT

4051 GACCAAAATC CCTTAACGTG AGTTTTCGTT CCACTGAGCG TCAGACCCCG

4101 TAGAAAAGAT CAAAGGATCT TCTTGAGATC CTTTTTTTCT GCGCGTAATC
```

FIG. 26D

```
4151  TGCTGCTTGC AAACAAAAAA ACCACCGCTA CCAGCGGTGG TTTGTTTGCC

4201  GGATCAAGAG CTACCAACTC TTTTTCCGAA GGTAACTGGC TTCAGCAGAG

4251  CGCAGATACC AAATACTGTC CTTCTAGTGT AGCCGTAGTT AGGCCACCAC

4301  TTCAAGAACT CTGTAGCACC GCCTACATAC CTCGCTCTGC TAATCCTGTT

4351  ACCAGTGGCT GCTGCCAGTG GCGATAAGTC GTGTCTTACC GGGTTGGACT

4401  CAAGACGATA GTTACCGGAT AAGGCGCAGC GGTCGGGCTG AACGGGGGGT

4451  TCGTGCACAC AGCCCAGCTT GGAGCGAACG ACCTACACCG AACTGAGATA

4501  CCTACAGCGT GAGCTATGAG AAAGCGCCAC GCTTCCCGAA GGGAGAAAGG

4551  CGGACAGGTA TCCGGTAAGC GGCAGGGTCG AACAGGAGA GCGCACGAGG

4601  GAGCTTCCAG GGGGAAACGC CTGGTATCTT TATAGTCCTG TCGGGTTTCG

4651  CCACCTCTGA CTTGAGCGTC GATTTTTGTG ATGCTCGTCA GGGGGGCGGA

4701  GCCTATGGAA AAACGCCAGC AACGCGGCCT TTTTACGGTT CCTGGCCTTT
                                              BspLU11I
4751  TGCTGGCCTT TTGCTCACAT GTTCTTTCCT GCGTTATCCC CTGATTCTGT

4801  GGATAACCGT ATTACCGCCT TGAGTGAGC TGATACCGCT CGCCGCAGCC

4851  GAACGACCGA GCGCAGCGAG TCAGTGAGCG AGGAAGCGGA AGAGCGCCTG

4901  ATGCGGTATT TTCTCCTTAC GCATCTGTGC GGTATTTCAC ACCGCATATG
                                                    Bst1107I
4951  GTGCACTCTC AGTACAATCT GCTCTGATGC CGCATAGTTA AGCCAGTATA

5001  CACTCCGCTA TCGCTACGTG ACTGGGTCAT GGCTGCGCCC CGACACCCGC

5051  CAACACCCGC TGACGCGCCC TGACGGGCTT GTCTGCTCCC GGCATCCGCT

5101  TACAGACAAG CTGTGACCGT CTCCGGGAGC TGCATGTGTC AGAGGTTTTC

5151  ACCGTCATCA CCGAAACGCG CGAGGCAGCT GTGGAATGTG TGTCAGTTAG

5201  GGTGTGGAAA GTCCCCAGGC TCCCCAGCAG GCAGAAGTAT GCAAAGCATG

5251  CATCTCAATT AGTCAGCAAC CAGGCTCCCC AGCAGGCAGA AGTATGCAAA

5301  GCATGCATCT CAATTAGTCA GCAACCATAG TCCCGCCCCT AACTCCGCCC
```

FIG.26E

```
5351  ATCCCGCCCC TAACTCCGCC CAGTTCCGCC CATTCTCCGC CCCATGGCTG
                                                    Sfi I
5401  ACTAATTTTT TTTATTTATG CAGAGGCCGA GGCCGCCTCG GCCTCTGAGC
                                              Stu I/Avr II
5451  TATTCCAGAA GTAGTGAGGA GGCTTTTTTG GAGGCCTAGG CTTTTGCAAA

5501  AAGCTAGCTT CACGCTGCCG CAAGCACTCA GGGCGCAAGG GCTGCTAAAG

5551  GAAGCGGAAC ACGTAGAAAG CCAGTCCGCA GAAACGGTGC TGACCCCGGA

5601  TGAATGTCAG CTACTGGGCT ATCTGGACAA GGGAAAACGC AAGCGCAAAG

5651  AGAAAGCAGG TAGCTTGCAG TGGGCTTACA TGGCGATAGC TAGACTGGGC

5701  GGTTTTATGG ACAGCAAGCG AACCGGAATT GCCAGCTGGG GCGCCCTCTG

5751  GTAAGGTTGG GAAGCCCTGC AAAGTAAACT GGATGGCTTT CTTGCCGCCA
                                          Bgl II/Bcl I
5801  AGGATCTGAT GGCGCAGGGG ATCAAGATCT GATCAAGAGA CAGGATGAGG

5851  ATCGTTTCGC ATGATTGAAC AAGATGGATT GCACGCAGGT TCTCCGGCCG

5901  CTTGGGTGGA GAGGCTATTC GGCTATGACT GGGCACAACA GACAATCGGC

5951  TGCTCTGATG CCGCCGTGTT CCGGCTGTCA GCGCAGGGGC GCCCGGTTCT

6001  TTTTGTCAAG ACCGACCTGT CCGGTGCCCT GAATGAACTG CAGGACGAGG
                     Msc I
6051  CAGCGCGGCT ATCGTGGCTG GCCACGACGG GCGTTCCTTG CGCAGCTGTG

6101  CTCGACGTTG TCACTGAAGC GGGAAGGGAC TGGCTGCTAT TGGGCGAAGT

6151  GCCGGGGCAG GATCTCCTGT CATCTCACCT TGCTCCTGCC GAGAAAGTAT

6201  CCATCATGGC TGATGCAATG CGGCGGCTGC ATACGCTTGA TCCGGCTACC

6251  TGCCCATTCG ACCACCAAGC GAAACATCGC ATCGAGCGAG CACGTACTCG

6301  GATGGAAGCC GGTCTTGTCG ATCAGGATGA TCTGGACGAA GAGCATCAGG

6351  GGCTCGCGCC AGCCGAACTG TTCGCCAGGC TCAAGGCGCG CATGCCCGAC

6401  GGCGAGGATC TCGTCGTGAC CCATGGCGAT GCCTGCTTGC CGAATATCAT

6451  GGTGGAAAAT GGCCGCTTTT CTGGATTCAT CGACTGTGGC CGGCTGGGTG
          Rsr II
6501  TGGCGGACCG CTATCAGGAC ATAGCGTTGG CTACCCGTGA TATTGCTGAA
```

FIG.26F

6551 GAGCTTGGCG GCGAATGGGC TGACCGCTTC CTCGTGCTTT ACGGTATCGC

6601 CGCTCCCGAT TCGCAGCGCA TCGCCTTCTA TCGCCTTCTT GACGAGTTCT
                                            Nsp V
6651 TCTGAGCGGG ACTCTGGGGT TCGAAATGAC CGACCAAGCG ACGCCCAACC

6701 TGCCATCACG AGATTTCGAT TCCACCGCCG CCTTCTATGA AGGTTGGGC

6751 TTCGGAATCG TTTTCCGGGA CGCCGGCTGG ATGATCCTCC AGCGCGGGGA
                                   Sma I              Nru I
6801 TCTCATGCTG GAGTTCTTCG CCCACCCCGG GCTCGATCCC CTCGCGAGTT

6851 GGTTCAGCTG CTGCCTGAGG CTGGACGACC TCGCGGAGTT CTACCGGCAG

6901 TGCAAATCCG TCGGCATCCA GGAAACCAGC AGCGGCTATC CGCGCATCCA

6951 TGCCCCCGAA CTGCAGGAGT GGGGAGGCAC GATGGCCGCT TTGGTCCCGG

7001 ATCTTTGTGA AGGAACCTTA CTTCTGTGGT GTGACATAAT TGGACAAACT

7051 ACCTACAGAG ATTTAAAGCT CTAAGGTAAA TATAAAATTT TTAAGTGTAT

7101 AATGTGTTAA ACTACTGATT CTAATTGTTT GTGTATTTTA GATTCCAACC

7151 TATGGAACTG ATGAATGGGA GCAGTGGTGG AATGCCTTTA ATGAGGAAAA

7201 CCTGTTTTGC TCAGAAGAAA TGCCATCTAG TGATGATGAG GCTACTGCTG

7251 ACTCTCAACA TTCTACTCCT CCAAAAAAGA AGAGAAAGGT AGAAGACCCC

7301 AAGGACTTTC CTTCAGAATT GCTAAGTTTT TTGAGTCATG CTGTGTTTAG

7351 TAATAGAACT CTTGCTTGCT TTGCTATTTA CACCACAAAG GAAAAAGCTG

7401 CACTGCTATA CAAGAAAATT ATGGAAAAAT ATTCTGTAAC CTTTATAAGT

7451 AGGCATAACA GTTATAATCA TAACATACTG TTTTTTCTTA CTCCACACAG

7501 GCATAGAGTG TCTGCTATTA ATAACTATGC TCAAAAATTG TGTACCTTTA

7551 GCTTTTTAAT TTGTAAAGGG GTTAATAAGG AATATTTGAT GTATAGTGCC

7601 TTGACTAGAG ATCATAATCA GCCATACCAC ATTTGTAGAG GTTTTACTTG

7651 CTTTAAAAAA CCTCCCACAC CTCCCCCTGA ACCTGAAACA TAAAATGAAT
        Mun I
7701 GCAATTGTTG TTGTTAACTT GTTTATTGCA GCTTATAATG GTTACAAATA

FIG.26G

7751 AAGCAATAGC ATCACAAATT TCACAAATAA AGCATTTTTT TCACTGCATT

7801 CTAGTTGTGG TTTGTCCAAA CTCATCAATG TATCTTATCA TGTCTGGATC

7851 TAATAAAAGA TATTTATTTT CATTAGATAT GTGTGTTGGT TTTTTGTGTG

7901 CAGTGCCTCT ATCTGGAGGC CAGGTAGGGC TGGCCTTGGG GGAGGGGGAG

7951 GCCAGAATGA CTCCAAGAGC TACAGGAAGG CAGGTCAGAG ACCCCACTGG

8001 ACAAACAGTG GCTGGACTCT GCACCATAAC ACACAATCAA CAGGGGAGTG

8051 AGCTGGAAAT TTGCTAGC

FIG.26H

1 TTGAAGACGAAAGGGCCTCGTGATACGCCTATTTTTATAGGTTAATGTCATGATAATAAT

61 GGTTTCTTAGACGTCAGGTGGCACTTTTCGGGGAAATGTGCGCGGAACCCCTATTTGTTT

121 ATTTTTCTAAATACATTCAAATATGTATCCGCTCATGAGACAATAACCCTGATAAATGCT

181 TCAATAATATTGAAAAAGGAAGAGTATGAGTATTCAACATTTCCGTGTCGCCCTTATTCC

241 CTTTTTTGCGGCATTTTGCCTTCCTGTTTTTGCTCACCCAGAAACGCTGGTGAAAGTAAA

301 AGATGCTGAAGATCAGTTGGGTGCACGAGTGGGTTACATCGAACTGGATCTCAACAGCGG

361 TAAGATCCTTGAGAGTTTTCGCCCCGAAGAACGTTTTCCAATGATGAGCACTTTTAAAGT

421 TCTGCTATGTGGCGCGGTATTATCCCGTGTTGACGCCGGGCAAGAGCAACTCGGTCGCCG

481 CATACACTATTCTCAGAATGACTTGGTTGAGTACTCACCAGTCACAGAAAAGCATCTTAC

541 GGATGGCATGACAGTAAGAGAATTATGCAGTGCTGCCATAACCATGAGTGATAACACTGC
                                                          Pvu I
601 GGCCAACTTACTTCTGACAACGATCGGAGGACCGAAGGAGCTAACCGCTTTTTTGCACAA

661 CATGGGGGATCATGTAACTCGCCTTGATCGTTGGGAACCGGAGCTGAATGAAGCCATACC
                                                          Fsp I
721 AAACGACGAGCGTGACACCACGATGCCTGCAGCAATGGCAACAACGTTGCGCAAACTATT

781 AACTGGCGAACTACTTACTCTAGCTTCCCGGCAACAATTAATAGACTGGATGGAGGCGGA

FIG.27A

```
 841 TAAAGTTGCAGGACCACTTCTGCGCTCGGCCCTTCCGGCTGGCTGGTTTATTGCTGATAA

901 ATCTGGAGCCGGTGAGCGTGGGTCTCGCGGTATCATTGCAGCACTGGGGCCAGATGGTAA

961 GCCCTCCCGTATCGTAGTTATCTACACGACGGGGAGTCAGGCAACTATGGATGAACGAAA

1021 TAGACAGATCGCTGAGATAGGTGCCTCACTGATTAAGCATTGGTAACTGTCAGACCAAGT

1081 TTACTCATATATACTTTAGATTGATTTAAAACTTCATTTTTAATTTAAAAGGATCTAGGT

1141 GAAGATCCTTTTTGATAATCTCATGACCAAAATCCCTTAACGTGAGTTTTCGTTCCACTG

1201 AGCGTCAGACCCCGTAGAAAAGATCAAAGGATCTTCTTGAGATCCTTTTTTTCTGCGCGT

1261 AATCTGCTGCTTGCAAACAAAAAAACCACCGCTACCAGCGGTGGTTTGTTTGCCGGATCA

1321 AGAGCTACCAACTCTTTTTCCGAAGGTAACTGGCTTCAGCAGAGCGCAGATACCAAATAC

1381 TGTCCTTCTAGTGTAGCCGTAGTTAGGCCACCACTTCAAGAACTCTGTAGCACCGCCTAC

1441 ATACCTCGCTCTGCTAATCCTGTTACCAGTGGCTGCTGCCAGTGGCGATAAGTCGTGTCT

1501 TACCGGGTTGGACTCAAGACGATAGTTACCGGATAAGGCGCAGCGGTCGGGCTGAACGGG

1561 GGGTTCGTGCACACAGCCCAGCTTGGAGCGAACGACCTACACCGAACTGAGATACCTACA

1621 GCGTGAGCTATGAGAAAGCGCCACGCTTCCCGAAGGGAGAAAGGCGGACAGGTATCCGGT

1681 AAGCGGCAGGGTCGGAACAGGAGAGCGCACGAGGGAGCTTCCAGGGGGAAACGCCTGGTA

1741 TCTTTATAGTCCTGTCGGGTTTCGCCACCTCTGACTTGAGCGTCGATTTTTGTGATGCTC

1801 GTCAGGGGGGCGGAGCCTATGGAAAAACGCCAGCAACGCGGCCTTTTTACGGTTCCTGGC
                                          BspLU11I
1861 CTTTTGCTGGCCTTTTGCTCACATGTTCTTTCCTGCGTTATCCCCTGATTCTGTGGATAA

1921 CCGTATTACCGCCTTTGAGTGAGCTGATACCGCTCGCCGCAGCCGAACGACCGAGCGCAG

1981 CGAGTCAGTGAGCGAGGAAGCGGAAGAGCGCCTGATGCGGTATTTTCTCCTTACGCATCT

2041 GTGCGGTATTTCACACCGCATATGGTGCACTCTCAGTACAATCTGCTCTGATGCCGCATA
             Bst1107 I
2101 GTTAAGCCAGTATACACTCCGCTATCGCTACGTGACTGGGTCATGGCTGCGCCCCGACAC

2161 CCGCCAACACCCGCTGACGCGCCCTGACGGGCTTGTCTGCTCCCGGCATCCGCTTACAGA

2221 CAAGCTGTGACCGTCTCCGGGAGCTGCATGTGTCAGAGGTTTTCACCGTCATCACCGAAA
```

FIG.27B

2281 CGCGCGAGGCAGCATGCATCTCAATTAGTCAGCAACCATAGTCCCGCCCCTAACTCCGCC

2341 CATCCCGCCCCTAACTCCGCCCAGTTCCGCCCATTCTCCGCCCCATGGCTGACTAATTTT
                                    Sfi I
2401 TTTTATTTATGCAGAGGCCGA<u>GGCCGCCTCGGCC</u>TCTGAGCTATTCCAGAAGTAGTGAGG
                Stu I/Avr II
2461 AGGCTTTTTTGG<u>AGGCCTAGG</u>CTTTTGCAAAAAGCTAGCTTACAGCTCAGGGCTGCGATT

2521 TCGCGCCAAACTTGACGGCAATCCTAGCGTGAAGGCTGGTAGGATTTTATCCCCGCTGCC

2581 ATCATGGTTCGACCATTGAACTGCATCGTCGCCGTGTCCCAAAATATGGGGATTGGCAAG

2641 AACGGAGACCTACCCTGGCCTCCGCTCAGGAACGAGTTCAAGTACTTCCAAAGAATGACC

2701 ACAACCTCTTCAGTGGAAGGTAAACAGAATCTGGTGATTATGGGTAGGAAAACCTGGTTC

2761 TCCATTCCTGAGAAGAATCGACCTTTAAAGGACAGAATTAATATAGTTCTCAGTAGAGAA

2821 CTCAAAGAACCACCACGAGGAGCTCATTTTCTTGCCAAAAGTTTGGATGATGCCTTAAGA

2881 CTTATTGAACAACCGGAATTGGCAAGTAAAGTAGACATGGTTTGGATAGTCGGAGGCAGT

2941 TCTGTTTACCAGGAAGCCATGAATCAACCAGGCCACCTCAGACTCTTTGTGACAAGGATC

3001 ATGCAGGAATTTGAAAGTGACACGTTTTTCCCAGAAATTGATTTGGGGAAATATAAACTT

3061 CTCCCAGAATACCCAGGCGTCCTCTCTGAGGTCCAGGAGGAAAAAGGCATCAAGTATAAG

3121 TTTGAAGTCTACGAGAAGAAAGACTAACAGGAAGATGCTTTCAAGTTCTCTGCTCCCCTC
                                                        Bgl II
3181 CTAAAGCTATGCATTTTTATAAGACCATGGGACTTTTGCTGGCTTT<u>AGATCT</u>TTGTGAAG

3241 GAACCTTACTTCTGTGGTGTGACATAATTGGACAAACTACCTACAGAGATTTAAAGCTCT

3301 AAGGTAAATATAAAATTTTTAAGTGTATAATGTGTTAAACTACTGATTCTAATTGTTTGT

3361 GTATTTAGATTCCAACCTATGGAACTGATGAATGGGAGCAGTGGTGGAATGCCTTTAAT

3421 GAGGAAAACCTGTTTTGCTCAGAAGAAATGCCATCTAGTGATGATGAGGCTACTGCTGAC

3481 TCTCAACATTCTACTCCTCCAAAAAAGAAGAGAAAGGTAGAAGACCCCAAGGACTTTCCT

3541 TCAGAATTGCTAAGTTTTTTGAGTCATGCTGTGTTTAGTAATAGAACTCTTGCTTGCTTT

3601 GCTATTTACACCACAAAGGAAAAAGCTGCACTGCTATACAAGAAAATTATGGAAAAATAT

3661 TCTGTAACCTTTATAAGTAGGCATAACAGTTATAATCATAACATACTGTTTTTTCTTACT

FIG.27C

3721 CCACACAGGCATAGAGTGTCTGCTATTAATAACTATGCTCAAAAATTGTGTACCTTTAGC

3781 TTTTTAATTTGTAAAGGGGTTAATAAGGAATATTTGATGTATAGTGCCTTGACTAGA<u>GAT</u>
　　　　　　　　　　　　　　　　　　　　　　　　　　　　　　　　　　BsaB I
3841 <u>CATAATC</u>AGCCATACCACATTTGTAGAGGTTTTACTTGCTTTAAAAAACCTCCCACACCT
　　　　　　　　　　　　　　　　　　　　　　　　　Mun I
3901 CCCCCTGAACCTGAAACATAAAATGAATG<u>CAATTG</u>TTGTTGTTAACTTGTTTATTGCAGC

3961 TTATAATGGTTACAAATAAAGCAATAGCATCACAAATTTCACAAATAAAGCATTTTTTC

4021 ACTGCATTCTAGTTGTGGTTTGTCCAAACTCATCAATGTATCTTATCATGTCTGGATCTA

4081 ATAAAAGATATTTATTTTCATTAGATATGTGTGTTGGTTTTTTGTGTGCAGTGCCTCTAT

4141 CTGGAGGCCAGGTAGGGCTGGCCTTGGGGGAGGGGGAGGCCAGAATGACTCCAAGAGCTA

4201 CAGGAAGGCAGGTCAGAGACCCCACTGGACAAACAGTGGCTGGACTCTGCACCATAACAC
　　　　　　　　　　　　　　　　　　　　　　　　　　　　　　EcoR I
4261 ACAATCAACAGGGGAGTGAGCTGGAAATTTGCTAGC<u>GAATTC</u>cagcacactggcggccgt
　　　　Spe I
4321 t<u>ACTAGT</u>TATTAATAGTAATCAATTACGGGGTCATTAGTTCATAGCCCATATATGGAGTT

4381 CCGCGTTACATAACTTACGGTAAATGGCCCGCCTGGCTGACCGCCCAACGACCCCCGCCC

4441 ATTGACGTCAATAATGACGTATGTTCCCATAGTAACGCCAATAGGGACTTTCCATTGACG

4501 TCAATGGGTGGAGTATTTACGGTAAACTGCCCACTTGGCAGTACATCAAGTGTATCATAT

4561 GCCAAGTACGCCCCCTATTGACGTCAATGACGGTAAATGGCCCGCCTGGCATTATGCCCA
　　　　　　　　　　　　　　　　　　　　　　　　　　　　　　SnaB I
4621 GTACATGACCTTATGGGACTTTCCTACTTGGCAGTACATC<u>TACGTA</u>TTAGTCATCGCTAT

4681 TACCATGGTGATGCGGTTTTGGCAGTACATCAATGGGCGTGGATAGCGGTTTGACTCACG

4741 GGGATTTCCAAGTCTCCACCCCATTGACGTCAATGGGAGTTTGTTTTGGCACCAAAATCA

4801 ACGGGACTTTCCAAAATGTCGTAACAACTCCGCCCCATTGACGCAAATGGGCGGTAGGCG

4861 TGTACGGTGGGAGGTCTATATAAGCAGAGCTCGTTTAGTGAACCGTCAGATCGCCTGGAG

4921 ACGCCATCCACGCTGTTTTGACCTCCATAGAAGACACCGGGACCGATCCAGCCTCCGCGG

4981 CCGGGAACGGTGCATTGGAACGCGGATTCCCCGTGCCAAGAGTGACGTAAGTACCGCCTA

5041 TAGAGTCTATAGGCCCACCCCCTTGGCTTCTTATGCATGCTATACTGTTTTTGGCTTGGG
　　　　　　　　　　　　　　　　　　　　　　　　　　　　　Bpu1102I
5101 GTCTATACACCCCCGCTTCCTCATGTTATAGGTGATGGTATA<u>GCTTAGC</u>CTATAGGTGTG

FIG.27D

```
                           Xcm I
5161  GGTTATTGACCATTATTGACCACTCCCCTATTGGTGACGATACTTTCCATTACTAATCCA

5221  TAACATGGCTCTTTGCCACAACTCTCTTTATTGGCTATATGCCAATACACTGTCCTTCAG

5281  AGACTGACACGGACTCTGTATTTTTACAGGATGGGGTCTCATTTATTATTTACAAATTCA

5341  CATATACAACACCACCGTCCCCAGTGCCCGCAGTTTTTATTAAACATAACGTGGGATCTC
                           BspE I
5401  CACGCGAATCTCGGGTACGTGTTCCGGACATGGGCTCTTCTCCGGTAGCGGCGGAGCTTC

5461  TACATCCGAGCCCTGCTCCCATGCCTCCAGCGACTCATGGTCGCTCGGCAGCTCCTTGCT

5521  CCTAACAGTGGAGGCCAGACTTAGGCACAGCACGATGCCCACCACCACCAGTGTGCCGCA

5581  CAAGGCCGTGGCGGTAGGGTATGTGTCTGAAAATGAGCTCggggagcgggcttgcaccgc
                                                        (Pvu II)
5641  tgacgcatttggaagacttaaggcagcggcagaagaagatgcaggcagctgagttgttgt 5701  gttctgataagagtcagaggtaactcccgttgcggtgctgttaacggtggagggcagtgt 5761  agtctgagcagtactcgttgctgccgcgcgcgccaccagacataatagctgacagactaa
                                                        Mlu I
5821  cagactgttcctttccatgggtcttttctgcagtcaccgtccttgacACGCGTCTCGGGA
      Hind III
5881  AGCTTGCCGCCACCATGGGATGGAGCTGGGTCTTTCTCTTTCTCCTGTCAGGAACTGCAG
                M  G  W  S  W  V  F  L  F  L  L  S  G  T  A
             (Pvu II)
5941  GTGTCCTCTCTGAGGTCCAGCTGCAACAGTCTGGACCTGAGCTGGTGAAGCCTGGGGCTT
       G  V  L  S  E  V  Q  L  Q  Q  S  G  P  E  L  V  K  P  G  A
                   Xba I                              Dra III
6001  CAGTAAAGATGTCCTGCAAGACTTCTAGATACACATTCACTGAATACACCATACACTGGG
       S  V  .K  M  S  C  K  T  S  R  Y  T  F  T  E  Y  T  I  H  W
                                                     CDR 1
6061  TGAGACAGAGCCATGGAAAGAGCCTTGAGTGGATTGGAGGTATTAATCCTAACAATGGTA
       V  R  Q  S  H  G  K  S  L  E  W  I  G  G  I  N  P  N  N  G
6121  TTCCTAACTACAACCAGAAGTTCAAGGGCAGGGCCACATTGACTGTAGGCAAGTCCTCCA
       I  P  N  Y  N  Q  K  F  K  G  R  A  T  L  T  V  G  K  S  S
            CDR 2
6181  GCACCGCCTACATGGAGCTCCGCAGCCTGACATCTGAGGATTCTGCGGTCTATTTCTGTG
       S  T  A  Y  M  E  L  R  S  L  T  S  E  D  S  A  V  Y  F  C 6241  CAAGAAGAAGAATCGCCTATGGTTACGACGAGGGCCATGCTATGGACTACTGGGGTCAAG
       A  R  R  R  I  A  Y  G  Y  D  E  G  H  A  M  D  Y  W  G  Q
                CDR 3                      BamH I
6301  GAACCTCAGTCACCGTCTCCTCAGGTGAGTGGATCCTCTGCGCCTGGGCCCAGCTCTGTC
       G  T  S  V  T  V  S  S
```

FIG.27E

```
6361 CCACACCGCGGTCACATGGCACCACCTCTCTTGCAGCCTCCACCAAGGGCCCATCGGTCT
                                           S  T  K  G  P  S  V

6421 TCCCCCTGGCACCCTCCTCCAAGAGCACCTCTGGGGGCACAGCGGCCCTGGGCTGCCTGG
      F  P  L  A  P  S  S  K  S  T  S  G  G  T  A  A  L  G  C  L
                           Age I
6481 TCAAGGACTACTTCCCCGAACCGGTGACGGTGTCGTGGAACTCAGGCGCCCTGACCAGCG
      V  K  D  Y  F  P  E  P  V  T  V  S  W  N  S  G  A  L  T  S

6541 GCGTGCACACCTTCCCGGCTGTCCTACAGTCCTCAGGACTCTACTCCCTCAGCAGCGTGG
      G  V  H  T  F  P  A  V  L  Q  S  S  G  L  Y  S  L  S  S  V
     BstE II
6601 TGACCGTGCCCTCCAGCAGCTTGGGCACCCAGACCTACATCTGCAACGTGAATCACAAGC
      V  T  V  P  S  S  S  L  G  T  Q  T  Y  I  C  N  V  N  H  K

6661 CCAGCAACACCAAGGTGGACAAGAAAGTTGAGCCCAAATCTTGTGACAAAACTCACACAT
      P  S  N  T  K  V  D  K  K  V  E  P  K  S  C  D  K  T  H  T

6721 GCCCACCGTGCCCAGCACCTGAACTCCTGGGGGGACCGTCAGTCTTCCTCTTCCCCCCAA
      C  P  P  C  P  A  P  E  L  L  G  G  P  S  V  F  L  F  P  P

6781 AACCCAAGGACACCCTCATGATCTCCCGGACCCCTGAGGTCACATGCGTGGTGGTGGACG
     ….. K  P  K  D  T  L  M  I  S  R  T  P  E  V  T  C  V  V  D

6841 TGAGCCACGAAGACCCTGAGGTCAAGTTCAACTGGTACGTGGACGGCGTGGAGGTGCATA
      V  S  H  E  D  P  E  V  K  F  N  W  Y  V  D  G  V  E  V  H

6901 ATGCCAAGACAAAGCCGCGGGAGGAGCAGTACAACAGCACGTACCGGGTGGTCAGCGTCC
      N  A  K  T  K  P  R  E  E  Q  Y  N  S  T  Y  R  V  V  S  V

6961 TCACCGTCCTGCACCAGGACTGGCTGAATGGCAAGGAGTACAAGTGCAAGGTCTCCAACA
      L  T  V  L  H  Q  D  W  L  N  G  K  E  Y  K  C  K  V  S  N

7021 AAGCCCTCCCAGCCCCCATCGAGAAAACCATCTCCAAAGCCAAAGGGCAGCCCCGAGAAC
      K  A  L  P  A  P  I  E  K  T  I  S  K  A  K  G  Q  P  R  E

7081 CACAGGTGTACACCCTGCCCCCATCCCGGGAGGAGATGACCAAGAACCAGGTCAGCCTGA
      P  Q  V  Y  T  L  P  P  S  R  E  E  M  T  K  N  Q  V  S  L

7141 CCTGCCTGGTCAAAGGCTTCTATCCCAGCGACATCGCCGTGGAGTGGGAGAGCAATGGGC
      T  C  L  V  K  G  F  Y  P  S  D  I  A  V  E  W  E  S  N  G

7201 AGCCGGAGAACAACTACAAGACCACGCCTCCCGTGCTGGACTCCGACGGCTCCTTCTTCC
      Q  P  E  N  N  Y  K  T  T  P  P  V  L  D  S  D  G  S  F  F

7261 TCTACAGCAAGCTCACCGTGGACAAGAGCAGGTGGCAGCAGGGGAACGTCTTCTCATGCT
      L  Y  S  K  L  T  V  D  K  S  R  W  Q  Q  G  N  V  F  S  C
```

FIG.27F

```
7321 CCGTGATGCATGAGGCTCTGCACAACCACTACACGCAGAAGAGCCTCTCCCTGTCTCCGG
      S  V  M  H  E  A  L  H  N  H  Y  T  Q  K  S  L  S  L  S  P
                              NgoM I
7381 GTAAATGAGTGCGACGGCCGGCAAGCCCCGCTCCCCGGGCTCTCGCGGTCGCACGAGGAT
      G  K  *
7441 GCTTGGCACGTACCCCCTGTACATACTTCCCGGGCGCCCAGCATGGAAATAAAGCACCGG

7501 ATCTAATAAAAGATATTTATTTTCATTAGATATGTGTGTTGGTTTTTTGTGTGCAGTGCC

7561 TCTATCTGGAGGCCAGGTAGGGCTGGCCTTGGGGGAGGGGGAGGCCAGAATGACTCCAAG

7621 AGCTACAGGAAGGCAGGTCAGAGACCCCACTGGACAAACAGTGGCTGGACTCTGCACCAT

7681 AACACACAATCAACAGGGGAGTGAGCTGGaaatttgctagcgaattaattc 7731
```

FIG.27G

```
     1                                                                            19
     D   I   V   M   T   Q   S   P   D   S   L   A   V   S   L   G   E   R   A
A   GAC ATT GTG ATG ACC CAA TCT CCA GAC TCT TTG GCT GTG TCT CTA GGG GAG AGG GCC

B   --- --- --- --- --- --- --- --- --- --- --- --- --- --- --- --- --- --- ---

C   --- --- --- --- --- --- --- --- --- --- --- --- --- --- --- --- --- --- ---

20                    CDR1   27  A   B   C   D   E   F   28                32
     T   I   N   C | K   S   S   Q   S   L   L   Y   S   R   N   Q   K   N   Y
A   ACC ATC AAC TGC|AAG TCC AGT CAG AGC CTT TTA TAT TCT AGA AAT CAA AAG AAC TAC
                   |
B   --- --- --- ---|--- --- --- --- --- --- --- --- --- --- --- --- --- --- ---
                   |
C   --- --- --- ---|--- --- --- --- --- --- --- --- --- --- --- --- --- --- ---

33                                                                          51
     L   A | W   Y   Q   Q   K   P   G   Q   P   P   K   L   L   I   F | W   A
A   TTG GCC|TGG TAT CAG CAG AAA CCA GGA CAG CCA CCC AAA CTC CTC ATC TTT|TGG GCT
         . |  .   F                                                     |  .   .
B   --- ---|--- -TC --- --- --- --- --- --- --- --- --- --- --- --- ---|--- ---
           |                                                        Y   |
C   --- ---|--- --- --- --- --- --- --- --- --- --- --- --- --- --- -A-|--- ---

52        CDR2                                                              70
     S   T   R   E   S | G   V   P   D   R   F   S   G   S   G   F   G   T   D
A   AGC ACT AGG GAA TCT|GGG GTA CCT GAT AGG TTC AGT GGC AGT GGG TTT GGG ACA GAC
                       |
B   --- --- --- --- ---|--- --- --- --- --- --- --- --- --- --- --- --- --- ---
                       |
C   --- --- --- --- ---|--- --- --- --- --- --- --- --- --- --- --- --- --- ---
```

FIG. 29A

```
       71                                                                              88
        F   T   L   T   I   S   S   L   Q   A   E   D   V   A   V   Y   Y   C
A      TTC ACC CTC ACC ATT AGC AGC CTG CAG GCT GAA GAT GTG GCA GTT TAT TAC TGT
                                                                        D   .
B      --- --- --- --- --- --- --- --- --- --- --- --- --- --- --- --- G-- ---

C      --- --- --- --- --- --- --- --- --- --- --- --- --- --- --- --- --- ---

89              CDR3                                                           107
      | Q   Q   Y   F   S   Y   P   L   T |F   G   Q   G   T   K   V   E   I   K
A     |CAG CAA TAT TTT AGC TAT CCG CTC ACG|TTC GGA CAA GGG ACC AAG GTG GAA ATA AAA
      |                                   |
B     |--A --- --- --- --- --- --- --- ---|--- --- --- --- --- --- --- --- --- ---
      |                                   |
C     |--- --- --- --- --- --- --- --- ---|--- --- --- --- --- --- --- --- --- ---
```

FIG. 29B

```
                              Spe I
   1  gaattccagc acactggcgg ccgttACTAG TTATTAATAG TAATCAATTA
  51  CGGGGTCATT AGTTCATAGC CCATATATGG AGTTCCGCGT TACATAACTT
 101  ACGGTAAATG GCCCGCCTGG CTGACCGCCC AACGACCCCC GCCCATTGAC
 151  GTCAATAATG ACGTATGTTC CCATAGTAAC GCCAATAGGG ACTTTCCATT
 201  GACGTCAATG GGTGGAGTAT TTACGGTAAA CTGCCCACTT GGCAGTACAT
 251  CAAGTGTATC ATATGCCAAG TACGCCCCCT ATTGACGTCA ATGACGGTAA
 301  ATGGCCCGCC TGGCATTATG CCCAGTACAT GACCTTATGG GACTTTCCTA
                   SnaB I
 351  CTTGGCAGTA CATCTACGTA TTAGTCATCG CTATTACCAT GGTGATGCGG
 401  TTTTGGCAGT ACATCAATGG GCGTGGATAG CGGTTTGACT CACGGGGATT
 451  TCCAAGTCTC CACCCCATTG ACGTCAATGG GAGTTTGTTT TGGCACCAAA
 501  ATCAACGGGA CTTTCCAAAA TGTCGTAACA ACTCCGCCCC ATTGACGCAA
 551  ATGGGCGGTA GGCGTGTACG GTGGGAGGTC TATATAAGCA GAGCTCGTTT
 601  AGTGAACCGT CAGATCGCCT GGAGACGCCA TCCACGCTGT TTTGACCTCC
                                        Sac II
 651  ATAGAAGACA CCGGGACCGA TCCAGCCTCC GCGGCCGGGA ACGGTGCATT
 701  GGAACGCGGA TTCCCCGTGC CAAGAGTGAC GTAAGTACCG CCTATAGAGT
 751  CTATAGGCCC ACCCCCTTGG CTTCTTATGC ATGCTATACT GTTTTTGGCT
 801  TGGGGTCTAT ACCCCCCGC TTCCTCATGT TATAGGTGAT GGTATAGCTT
 851  AGCCTATAGG TGTGGGTTAT TGACCATTAT TGACCACTCC CCTATTGGTG
 901  ACGATACTTT CCATTACTAA TCCATAACAT GGCTCTTTGC CACAACTCTC
 951  TTTATTGGCT ATATGCCAAT ACACTGTCCT TCAGAGACTG ACACGGACTC
1001  TGTATTTTTA CAGGATGGGG TCTCATTTAT TATTTACAAA TTCACATATA
1051  CAACACCACC GTCCCCAGTG CCCGCAGTTT TTATTAAACA TAACGTGGGA
                                (BspE I)
1101  TCTCCACGCG AATCTCGGGT ACGTGTTCCG GACATGGGCT CTTCTCCGGT
1151  AGCGGCGGAG CTTCTACATC CGAGCCCTGC TCCCATGCCT CCAGCGACTC
```

FIG.30A

```
1201  ATGGTCGCTC  GGCAGCTCCT  TGCTCCTAAC  AGTGGAGGCC  AGACTTAGGC

1251  ACAGCACGAT  GCCCACCACC  ACCAGTGTGC  CGCACAAGGC  CGTGGCGGTA

1301  GGGTATGTGT  CTGAAAATGA  GCTCggggag  cgggcttgca  ccgctgacgc
                              Afl II
1351  atttggaaga  cttaaggcag  cggcagaaga  agatgcaggc  agctgagttg 1401  ttgtgttctg  ataagagtca  gaggtaactc  ccgttgcggt  gctgttaacg 1451  gtggagggca  gtgtagtctg  agcagtactc  gttgctgccg  cgcgcgccac 1501  cagacataat  agctgacaga  ctaacagact  gttcctttcc  atgggtcttt
                                          Mlu I        Hind III
1551  tctgcagtca  ccgtccttga  cacgcgtctc  gggaagcttG  CCGCCACCAT
                                                                    M
1601  GGAGACAGAC  ACACTCCTGC  TATGGGTGCT  GCTGCTCTGG  GTTCCAGGTT
         E  T  D   T  L  L    L  W  V  L   L  L  W    V  P  G
      (BspE I)
1651  CCTCCGGAGA  CATTGTGATG  ACCCAATCTC  CAGACTCTTT  GGCTGTGTCT
       S  S  G  D   I  V  M   T  Q  S  P   D  S  L    A  V  S 1701  CTAGGGGAGA  GGGCCACCAT  CAACTGCAAG  TCCAGTCAGA  GCCTTTTATA
       L  G  E   R  A  T  I   N  C  K    S  S  Q    S  L  L  Y
       XbaI                              CDR 1
1751  TTCTAGAAAT  CAAAAGAACT  ACTTGGCCTG  GTATCAGCAG  AAACCAGGAC
       S  R  N   Q  K  N    Y  L  A       W  Y  Q  Q   K  P  G
                                                               KpnI
1801  AGCCACCCAA  ACTCCTCATC  TTTTGGGCTA  GCACTAGGGA  ATCTGGGGTA
       Q  P  P  K   L  L  I   F  W  A    S  T  R  E  S    G  V
                                         CDR 2
1851  CCTGATAGGT  TCAGTGGCAG  TGGGTTTGGG  ACAGACTTCA  CCCTCACCAT
       P  D  R    F  S  G  S   G  F  G   T  D  F    T  L  T  I 1901  TAGCAGCCTG  CAGGCTGAAG  ATGTGGCAGT  TTATTACTGT  CAGCAATATT
       S  S  L    Q  A  E    D  V  A  V   Y  Y  C    Q  Q  Y 1951  TTAGCTATCC  GCTCACGTTC  GGACAAGGGA  CCAAGGTGGA  AATAAAACGT
       F  S  Y  P   L  T    F  G  Q  G    T  K  V  E   I  K  R
             CDR 3
          BamH I
2001  GAGTggatcc  ATCTGGGATA  AGCATGCTGT  TTTCTGTCTG  TCCCTAACAT

2051  GCCCTGTGAT  TATGCGCAAA  CAACACACCC  AAGGGCAGAA  CTTTGTTACT

2101  TAAACACCAT  CCTGTTTGCT  TCTTTCCTCA  GGAACTGTGG  CTGCACCATC
                                                       T  V  A  A  P  S
```

FIG.30B

```
2151 TGTCTTCATC TTCCCGCCAT CTGATGAGCA GTTGAAATCT GGAACTGCCT
       V  F  I    F  P  P     S  D  E  Q    L  K  S     G  T  A
2201 CTGTTGTGTG CCTGCTGAAT AACTTCTATC CCAGAGAGGC CAAAGTACAG
      S  V  V  C  L  L  N    N  F  Y    P  R  E  A    K  V  Q
2251 TGGAAGGTGG ATAACGCCCT CCAATCGGGT AACTCCCAGG AGAGTGTCAC
      W  K  V    D  N  A  L    Q  S  G    N  S  Q    E  S  V  T
2301 AGAGCAGGAC AGCAAGGACA GCACCTACAG CCTCAGCAGC ACCCTGACGC
       E  Q  D    S  K  D    S  T  Y  S    L  S  S    T  L  T
2351 TGAGCAAAGC AGACTACGAG AAACACAAAG TCTACGCCTG CGAAGTCACC
      L  S  K  A    D  Y  E    K  H  K    V  Y  A  C    E  V  T
2401 CATCAGGGCC TGAGCTCGCC CGTCACAAAG AGCTTCAACA GGGGAGAGTG
      H  Q  G    L  S  S  P    V  T  K    S  F  N    R  G  E  C
2451 TTAGAGGGAG AAGTGCCCCC ACCTGCTCCT CAGTTCCAGC CTGACCCCCT
        *                                        Psp5 II
2501 CCCATCCTTT GGCCTCTGAC CCTTTTTCCA CAGGGGACCT ACCCCTATTG

2551 CGGTCCTCCA GCTCATCTTT CACCTCACCC CCCTCCTCCT CCTTGGCTTT

2601 AATTATGCTA ATGTTGGAGG AGAATGAATA AATAAAGTGA ATCTTTGCAC

2651 CTGTGGTGGA TCTAATAAAA GATATTTATT TTCATTAGAT ATGTGTGTTG

2701 GTTTTTTGTG TGCAGTGCCT CTATCTGGAG GCCAGGTAGG GCTGGCCTTG

2751 GGGGAGGGGG AGGCCAGAAT GACTCCAAGA GCTACAGGAA GGCAGGTCAG

2801 AGACCCCACT GGACAAACAG TGGCTGGACT CTGCACCATA ACACACAATC

2851 AACAGGGGAG TGAGCTGGAA ATTTGCTAGC GAATTCTTGA AGACGAAAGG

2901 GCCTCGTGAT ACGCCTATTT TTATAGGTTA ATGTCATGAT AATAATGGTT

2951 TCTTAGACGT CAGGTGGCAC TTTTCGGGGA AATGTGCGCG GAACCCCTAT

3001 TTGTTTATTT TTCTAAATAC ATTCAAATAT GTATCCGCTC ATGAGACAAT

3051 AACCCTGATA AATGCTTCAA TAATATTGAA AAAGGAAGAG TATGAGTATT

3101 CAACATTTCC GTGTCGCCCT TATTCCCTTT TTTGCGGCAT TTTGCCTTCC

3151 TGTTTTTGCT CACCCAGAAA CGCTGGTGAA AGTAAAAGAT GCTGAAGATC

3201 AGTTGGGTGC ACGAGTGGGT TACATCGAAC TGGATCTCAA CAGCGGTAAG

3251 ATCCTTGAGA GTTTTCGCCC CGAAGAACGT TTTCCAATGA TGAGCACTTT

3301 TAAAGTTCTG CTATGTGGCG CGGTATTATC CCGTGTTGAC GCCGGGCAAG
```

FIG.30C

```
3351  AGCAACTCGG TCGCCGCATA CACTATTCTC AGAATGACTT GGTTGAGTAC

3401  TCACCAGTCA CAGAAAAGCA TCTTACGGAT GGCATGACAG TAAGAGAATT

3451  ATGCAGTGCT GCCATAACCA TGAGTGATAA CACTGCGGCC AACTTACTTC
                Pvu I
3501  TGACAACGAT CGGAGGACCG AAGGAGCTAA CCGCTTTTTT GCACAACATG

3551  GGGGATCATG TAACTCGCCT TGATCGTTGG GAACCGGAGC TGAATGAAGC

3601  CATACCAAAC GACGAGCGTG ACACCACGAT GCCTGCAGCA ATGGCAACAA

3651  CGTTGCGCAA ACTATTAACT GGCGAACTAC TTACTCTAGC TTCCCGGCAA

3701  CAATTAATAG ACTGGATGGA GGCGGATAAA GTTGCAGGAC CACTTCTGCG

3751  CTCGGCCCTT CCGGCTGGCT GGTTTATTGC TGATAAATCT GGAGCCGGTG

3801  AGCGTGGGTC TCGCGGTATC ATTGCAGCAC TGGGGCCAGA TGGTAAGCCC

3851  TCCCGTATCG TAGTTATCTA CACGACGGGG AGTCAGGCAA CTATGGATGA

3901  ACGAAATAGA CAGATCGCTG AGATAGGTGC CTCACTGATT AAGCATTGGT

3951  AACTGTCAGA CCAAGTTTAC TCATATATAC TTTAGATTGA TTTAAAACTT

4001  CATTTTTAAT TTAAAAGGAT CTAGGTGAAG ATCCTTTTTG ATAATCTCAT

4051  GACCAAAATC CCTTAACGTG AGTTTTCGTT CCACTGAGCG TCAGACCCCG

4101  TAGAAAAGAT CAAAGGATCT TCTTGAGATC CTTTTTTTCT GCGCGTAATC

4151  TGCTGCTTGC AAACAAAAAA ACCACCGCTA CCAGCGGTGG TTTGTTTGCC

4201  GGATCAAGAG CTACCAACTC TTTTTCCGAA GGTAACTGGC TTCAGCAGAG

4251  CGCAGATACC AAATACTGTC CTTCTAGTGT AGCCGTAGTT AGGCCACCAC

4301  TTCAAGAACT CTGTAGCACC GCCTACATAC CTCGCTCTGC TAATCCTGTT

4351  ACCAGTGGCT GCTGCCAGTG GCGATAAGTC GTGTCTTACC GGGTTGGACT

4401  CAAGACGATA GTTACCGGAT AAGGCGCAGC GGTCGGGCTG AACGGGGGGT

4451  TCGTGCACAC AGCCCAGCTT GGAGCGAACG ACCTACACCG AACTGAGATA

4501  CCTACAGCGT GAGCTATGAG AAAGCGCCAC GCTTCCCGAA GGGAGAAAGG
```

FIG.30D

```
4551  CGGACAGGTA  TCCGGTAAGC  GGCAGGGTCG  GAACAGGAGA  GCGCACGAGG

4601  GAGCTTCCAG  GGGGAAACGC  CTGGTATCTT  TATAGTCCTG  TCGGGTTTCG

4651  CCACCTCTGA  CTTGAGCGTC  GATTTTGTG   ATGCTCGTCA  GGGGGGCGGA

4701  GCCTATGGAA  AAACGCCAGC  AACGCGGCCT  TTTTACGGTT  CCTGGCCTTT
                                 BspLU11I
4751  TGCTGGCCTT  TTGCTCACAT GTTCTTTCCT  GCGTTATCCC  CTGATTCTGT

4801  GGATAACCGT  ATTACCGCCT  TTGAGTGAGC  TGATACCGCT  CGCCGCAGCC

4851  GAACGACCGA  GCGCAGCGAG  TCAGTGAGCG  AGGAAGCGGA  AGAGCGCCTG

4901  ATGCGGTATT  TTCTCCTTAC  GCATCTGTGC  GGTATTTCAC  ACCGCATATG
                                                                  Bst1107I
4951  GTGCACTCTC  AGTACAATCT  GCTCTGATGC  CGCATAGTTA  AGCCAGTATA

5001  CACTCCGCTA  TCGCTACGTG  ACTGGGTCAT  GGCTGCGCCC  CGACACCCGC

5051  CAACACCCGC  TGACGCGCCC  TGACGGGCTT  GTCTGCTCCC  GGCATCCGCT

5101  TACAGACAAG  CTGTGACCGT  CTCCGGGAGC  TGCATGTGTC  AGAGGTTTTC

5151  ACCGTCATCA  CCGAAACGCG  CGAGGCAGCT  GTGGAATGTG  TGTCAGTTAG

5201  GGTGTGGAAA  GTCCCCAGGC  TCCCCAGCAG  GCAGAAGTAT  GCAAAGCATG

5251  CATCTCAATT  AGTCAGCAAC  CAGGCTCCCC  AGCAGGCAGA  AGTATGCAAA

5301  GCATGCATCT  CAATTAGTCA  GCAACCATAG  TCCCGCCCCT  AACTCCGCCC

5351  ATCCCGCCCC  TAACTCCGCC  CAGTTCCGCC  CATTCTCCGC  CCCATGGCTG
                                                       Sfi I
5401  ACTAATTTTT  TTTATTTATG  CAGAGGCCGA  GGCCGCCTCG GCCTCTGAGC
                                                    Stu I/Avr II
5451  TATTCCAGAA  GTAGTGAGGA  GGCTTTTTTG  GAGGCCTAGG  CTTTTGCAAA

5501  AAGCTAGCTT  CACGCTGCCG  CAAGCACTCA  GGGCGCAAGG  GCTGCTAAAG

5551  GAAGCGGAAC  ACGTAGAAAG  CCAGTCCGCA  GAAACGGTGC  TGACCCCGGA

5601  TGAATGTCAG  CTACTGGGCT  ATCTGGACAA  GGGAAAACGC  AAGCGCAAAG

5651  AGAAAGCAGG  TAGCTTGCAG  TGGGCTTACA  TGGCGATAGC  TAGACTGGGC

5701  GGTTTTATGG  ACAGCAAGCG  AACCGGAATT  GCCAGCTGGG  GCGCCCTCTG
```

FIG. 30E

```
5751  GTAAGGTTGG GAAGCCCTGC AAAGTAAACT GGATGGCTTT CTTGCCGCCA
                                       Bgl II/Bcl I
5801  AGGATCTGAT GGCGCAGGGG ATCAAGATCT GATCAAGAGA CAGGATGAGG

5851  ATCGTTTCGC ATGATTGAAC AAGATGGATT GCACGCAGGT TCTCCGGCCG

5901  CTTGGGTGGA GAGGCTATTC GGCTATGACT GGGCACAACA GACAATCGGC

5951  TGCTCTGATG CCGCCGTGTT CCGGCTGTCA GCGCAGGGGC GCCCGGTTCT

6001  TTTTGTCAAG ACCGACCTGT CCGGTGCCCT GAATGAACTG CAGGACGAGG
                         Msc I
6051  CAGCGCGGCT ATCGTGGCTG GCCACGACGG GCGTTCCTTG CGCAGCTGTG

6101  CTCGACGTTG TCACTGAAGC GGGAAGGGAC TGGCTGCTAT TGGGCGAAGT

6151  GCCGGGGCAG GATCTCCTGT CATCTCACCT TGCTCCTGCC GAGAAAGTAT

6201  CCATCATGGC TGATGCAATG CGGCGGCTGC ATACGCTTGA TCCGGCTACC

6251  TGCCCATTCG ACCACCAAGC GAAACATCGC ATCGAGCGAG CACGTACTCG

6301  GATGGAAGCC GGTCTTGTCG ATCAGGATGA TCTGGACGAA GAGCATCAGG

6351  GGCTCGCGCC AGCCGAACTG TTCGCCAGGC TCAAGGCGCG CATGCCCGAC

6401  GGCGAGGATC TCGTCGTGAC CCATGGCGAT GCCTGCTTGC CGAATATCAT

6451  GGTGGAAAAT GGCCGCTTTT CTGGATTCAT CGACTGTGGC CGGCTGGGTG
          Rsr II
6501  TGGCGGACCG CTATCAGGAC ATAGCGTTGG CTACCCGTGA TATTGCTGAA

6551  GAGCTTGGCG GCGAATGGGC TGACCGCTTC CTCGTGCTTT ACGGTATCGC

6601  CGCTCCCGAT TCGCAGCGCA TCGCCTTCTA TCGCCTTCTT GACGAGTTCT
                         Nsp V
6651  TCTGAGCGGG ACTCTGGGGT TCGAAATGAC CGACCAAGCG ACGCCCAACC

6701  TGCCATCACG AGATTTCGAT TCCACCGCCG CCTTCTATGA AAGGTTGGGC

6751  TTCGGAATCG TTTTCCGGGA CGCCGGCTGG ATGATCCTCC AGCGCGGGGA
                              Sma I                Nru I
6801  TCTCATGCTG GAGTTCTTCG CCCACCCCGG GCTCGATCCC CTCGCGAGTT

6851  GGTTCAGCTG CTGCCTGAGG CTGGACGACC TCGCGGAGTT CTACCGGCAG

6901  TGCAAATCCG TCGGCATCCA GGAAACCAGC AGCGGCTATC CGCGCATCCA
```

FIG.30F

```
6951  TGCCCCCGAA CTGCAGGAGT GGGGAGGCAC GATGGCCGCT TTGGTCCCGG

7001  ATCTTTGTGA AGGAACCTTA CTTCTGTGGT GTGACATAAT TGGACAAACT

7051  ACCTACAGAG ATTTAAAGCT CTAAGGTAAA TATAAAATTT TTAAGTGTAT

7101  AATGTGTTAA ACTACTGATT CTAATTGTTT GTGTATTTTA GATTCCAACC

7151  TATGGAACTG ATGAATGGGA GCAGTGGTGG AATGCCTTTA ATGAGGAAAA

7201  CCTGTTTTGC TCAGAAGAAA TGCCATCTAG TGATGATGAG GCTACTGCTG

7251  ACTCTCAACA TTCTACTCCT CCAAAAAAGA AGAGAAAGGT AGAAGACCCC

7301  AAGGACTTTC CTTCAGAATT GCTAAGTTTT TGAGTCATG CTGTGTTTAG

7351  TAATAGAACT CTTGCTTGCT TTGCTATTTA CACCACAAAG GAAAAAGCTG

7401  CACTGCTATA CAAGAAAATT ATGGAAAAAT ATTCTGTAAC CTTTATAAGT

7451  AGGCATAACA GTTATAATCA TAACATACTG TTTTTTCTTA CTCCACACAG

7501  GCATAGAGTG TCTGCTATTA ATAACTATGC TCAAAAATTG TGTACCTTTA

7551  GCTTTTTAAT TTGTAAAGGG GTTAATAAGG AATATTTGAT GTATAGTGCC

7601  TTGACTAGAG ATCATAATCA GCCATACCAC ATTTGTAGAG GTTTTACTTG

7651  CTTTAAAAAA CCTCCCACAC CTCCCCCTGA ACCTGAAACA TAAAATGAAT
           Mun I
7701  GCAATTGTTG TTGTTAACTT GTTTATTGCA GCTTATAATG GTTACAAATA

7751  AAGCAATAGC ATCACAAATT TCACAAATAA AGCATTTTTT TCACTGCATT

7801  CTAGTTGTGG TTTGTCCAAA CTCATCAATG TATCTTATCA TGTCTGGATC

7851  TAATAAAAGA TATTTATTTT CATTAGATAT GTGTGTTGGT TTTTTGTGTG

7901  CAGTGCCTCT ATCTGGAGGC CAGGTAGGGC TGGCCTTGGG GGAGGGGGAG

7951  GCCAGAATGA CTCCAAGAGC TACAGGAAGG CAGGTCAGAG ACCCCACTGG

8001  ACAAACAGTG GCTGGACTCT GCACCATAAC ACACAATCAA CAGGGGAGTG

8051  AGCTGGAAAT TTGCTAGC
```

```
      104                                              113
       G    Q    G    T    L    V    T    V    S    S
A     GGT  CAA  GGA  ACC  CTT  GTC  ACC  GTC  TCC  TCA

```
   1 TTGAAGACGAAAGGGCCTCGTGATACGCCTATTTTTATAGGTTAATGTCATGATAATAAT

61 GGTTTCTTAGACGTCAGGTGGCACTTTTCGGGGAAATGTGCGCGGAACCCCTATTTGTTT

121 ATTTTTCTAAATACATTCAAATATGTATCCGCTCATGAGACAATAACCCTGATAAATGCT

181 TCAATAATATTGAAAAGGAAGAGTATGAGTATTCAACATTTCCGTGTCGCCCTTATTCC

241 CTTTTTTGCGGCATTTTGCCTTCCTGTTTTTGCTCACCCAGAAACGCTGGTGAAAGTAAA

301 AGATGCTGAAGATCAGTTGGGTGCACGAGTGGGTTACATCGAACTGGATCTCAACAGCGG

361 TAAGATCCTTGAGAGTTTTCGCCCCGAAGAACGTTTTCCAATGATGAGCACTTTTAAAGT

421 TCTGCTATGTGGCGCGGTATTATCCCGTGTTGACGCCGGGCAAGAGCAACTCGGTCGCCG

481 CATACACTATTCTCAGAATGACTTGGTTGAGTACTCACCAGTCACAGAAAAGCATCTTAC

541 GGATGGCATGACAGTAAGAGAATTATGCAGTGCTGCCATAACCATGAGTGATAACACTGC
                                  Pvu I
 601 GGCCAACTTACTTCTGACAACGATCGGAGGACCGAAGGAGCTAACCGCTTTTTTGCACAA

661 CATGGGGGATCATGTAACTCGCCTTGATCGTTGGGAACCGGAGCTGAATGAAGCCATACC
                                                              Fsp I
 721 AAACGACGAGCGTGACACCACGATGCCTGCAGCAATGGCAACAACGTTGCGCAAACTATT

781 AACTGGCGAACTACTTACTCTAGCTTCCCGGCAACAATTAATAGACTGGATGGAGGCGGA

841 TAAAGTTGCAGGACCACTTCTGCGCTCGGCCCTTCCGGCTGGCTGGTTTATTGCTGATAA

901 ATCTGGAGCCGGTGAGCGTGGGTCTCGCGGTATCATTGCAGCACTGGGGCCAGATGGTAA

961 GCCCTCCCGTATCGTAGTTATCTACACGACGGGGAGTCAGGCAACTATGGATGAACGAAA

1021 TAGACAGATCGCTGAGATAGGTGCCTCACTGATTAAGCATTGGTAACTGTCAGACCAAGT

1081 TTACTCATATATACTTTAGATTGATTTAAAACTTCATTTTTAATTTAAAAGGATCTAGGT

1141 GAAGATCCTTTTTGATAATCTCATGACCAAAATCCCTTAACGTGAGTTTTCGTTCCACTG

1201 AGCGTCAGACCCCGTAGAAAAGATCAAAGGATCTTCTTGAGATCCTTTTTTTCTGCGCGT

1261 AATCTGCTGCTTGCAAACAAAAAAACCACCGCTACCAGCGGTGGTTTGTTTGCCGGATCA

1321 AGAGCTACCAACTCTTTTTCCGAAGGTAACTGGCTTCAGCAGAGCGCAGATACCAAATAC

1381 TGTCCTTCTAGTGTAGCCGTAGTTAGGCCACCACTTCAAGAACTCTGTAGCACCGCCTAC
```

FIG.33A

1441 ATACCTCGCTCTGCTAATCCTGTTACCAGTGGCTGCTGCCAGTGGCGATAAGTCGTGTCT

1501 TACCGGGTTGGACTCAAGACGATAGTTACCGGATAAGGCGCAGCGGTCGGGCTGAACGGG

1561 GGGTTCGTGCACACAGCCCAGCTTGGAGCGAACGACCTACACCGAACTGAGATACCTACA

1621 GCGTGAGCTATGAGAAAGCGCCACGCTTCCCGAAGGGAGAAAGGCGGACAGGTATCCGGT

1681 AAGCGGCAGGGTCGGAACAGGAGAGCGCACGAGGGAGCTTCCAGGGGGAAACGCCTGGTA

1741 TCTTTATAGTCCTGTCGGGTTTCGCCACCTCTGACTTGAGCGTCGATTTTGTGATGCTC

1801 GTCAGGGGGCGGAGCCTATGGAAAAACGCCAGCAACGCGGCCTTTTTACGGTTCCTGGC
                                          BspLU11I
1861 CTTTTGCTGGCCTTTTGCTC<u>ACATGT</u>TCTTTCCTGCGTTATCCCCTGATTCTGTGGATAA

1921 CCGTATTACCGCCTTTGAGTGAGCTGATACCGCTCGCCGCAGCCGAACGACCGAGCGCAG

1981 CGAGTCAGTGAGCGAGGAAGCGGAAGAGCGCCTGATGCGGTATTTTCTCCTTACGCATCT

2041 GTGCGGTATTTCACACCGCATATGGTGCACTCTCAGTACAATCTGCTCTGATGCCGCATA
            Bst1107 I
2101 GTTAAGCCA<u>GTATAC</u>ACTCCGCTATCGCTACGTGACTGGGTCATGGCTGCGCCCCGACAC

2161 CCGCCAACACCCGCTGACGCGCCCTGACGGGCTTGTCTGCTCCCGGCATCCGCTTACAGA

2221 CAAGCTGTGACCGTCTCCGGGAGCTGCATGTGTCAGAGGTTTTCACCGTCATCACCGAAA

2281 CGCGCGAGGCAGCATGCATCTCAATTAGTCAGCAACCATAGTCCCGCCCCTAACTCCGCC

2341 CATCCCGCCCCTAACTCCGCCCAGTTCCGCCCATTCTCCGCCCCATGGCTGACTAATTTT
                                               Sfi I
2401 TTTTATTTATGCAGAGGCCGA<u>GGCCGCCTCGGCC</u>TCTGAGCTATTCCAGAAGTAGTGAGG
                 Stu I/Avr II
2461 AGGCTTTTTTGG<u>AGGCCTAGG</u>CTTTTGCAAAAAGCTAGCTTACAGCTCAGGGCTGCGATT

2521 TCGCGCCAAACTTGACGGCAATCCTAGCGTGAAGGCTGGTAGGATTTTATCCCCGCTGCC

2581 ATCATGGTTCGACCATTGAACTGCATCGTCGCCGTGTCCCAAAATATGGGGATTGGCAAG

2641 AACGGAGACCTACCCTGGCCTCCGCTCAGGAACGAGTTCAAGTACTTCCAAAGAATGACC

2701 ACAACCTCTTCAGTGGAAGGTAAACAGAATCTGGTGATTATGGGTAGGAAAACCTGGTTC

2761 TCCATTCCTGAGAAGAATCGACCTTTAAAGGACAGAATTAATATAGTTCTCAGTAGAGAA

2821 CTCAAAGAACCACCACGAGGAGCTCATTTTCTTGCCAAAAGTTTGGATGATGCCTTAAGA

FIG.33B

2881 CTTATTGAACAACCGGAATTGGCAAGTAAAGTAGACATGGTTTGGATAGTCGGAGGCAGT

2941 TCTGTTTACCAGGAAGCCATGAATCAACCAGGCCACCTCAGACTCTTTGTGACAAGGATC

3001 ATGCAGGAATTTGAAAGTGACACGTTTTTCCCAGAAATTGATTTGGGGAAATATAAACTT

3061 CTCCCAGAATACCCAGGCGTCCTCTCTGAGGTCCAGGAGGAAAAAGGCATCAAGTATAAG

3121 TTTGAAGTCTACGAGAAGAAAGACTAACAGGAAGATGCTTTCAAGTTCTCTGCTCCCCTC

Bgl II

3181 CTAAAGCTATGCATTTTTATAAGACCATGGGACTTTTGCTGGCTTT<u>AGATCT</u>TTGTGAAG

3241 GAACCTTACTTCTGTGGTGTGACATAATTGGACAAACTACCTACAGAGATTTAAAGCTCT

3301 AAGGTAAATATAAAATTTTTAAGTGTATAATGTGTTAAACTACTGATTCTAATTGTTTGT

3361 GTATTTTAGATTCCAACCTATGGAACTGATGAATGGGAGCAGTGGTGGAATGCCTTTAAT

3421 GAGGAAAACCTGTTTTGCTCAGAAGAAATGCCATCTAGTGATGATGAGGCTACTGCTGAC

3481 TCTCAACATTCTACTCCTCCAAAAAAGAAGAGAAAGGTAGAAGACCCCAAGGACTTTCCT

3541 TCAGAATTGCTAAGTTTTTTGAGTCATGCTGTGTTTAGTAATAGAACTCTTGCTTGCTTT

3601 GCTATTTACACCACAAAGGAAAAAGCTGCACTGCTATACAAGAAAATTATGGAAAAATAT

3661 TCTGTAACCTTTATAAGTAGGCATAACAGTTATAATCATAACATACTGTTTTTTCTTACT

3721 CCACACAGGCATAGAGTGTCTGCTATTAATAACTATGCTCAAAAATTGTGTACCTTTAGC

3781 TTTTTAATTTGTAAAGGGGTTAATAAGGAATATTTGATGTATAGTGCCTTGACTAGA<u>GAT</u>
     BsaB I

3841 <u>CATAATC</u>AGCCATACCACATTTGTAGAGGTTTTACTTGCTTTAAAAAACCTCCCACACCT

Mun I

3901 CCCCCTGAACCTGAAACATAAAATGAATG<u>CAATTG</u>TTGTTGTTAACTTGTTTATTGCAGC

3961 TTATAATGGTTACAAATAAAGCAATAGCATCACAAATTTCACAAATAAAGCATTTTTTTC

4021 ACTGCATTCTAGTTGTGGTTTGTCCAAACTCATCAATGTATCTTATCATGTCTGGATCTA

4081 ATAAAAGATATTTATTTTCATTAGATATGTGTGTTGGTTTTTTGTGTGCAGTGCCTCTAT

4141 CTGGAGGCCAGGTAGGGCTGGCCTTGGGGGAGGGGGAGGCCAGAATGACTCCAAGAGCTA

4201 CAGGAAGGCAGGTCAGAGACCCCACTGGACAAACAGTGGCTGGACTCTGCACCATAACAC

FIG.33C

```
                                              EcoR I
4261  ACAATCAACAGGGGAGTGAGCTGGAAATTTGCTAGCGAATTCcagcacactggcggccgt
          (Spe I)
4321  tACTAGTTATTAATAGTAATCAATTACGGGGTCATTAGTTCATAGCCCATATATGGAGTT

4381  CCGCGTTACATAACTTACGGTAAATGGCCCGCCTGGCTGACCGCCCAACGACCCCCGCCC

4441  ATTGACGTCAATAATGACGTATGTTCCCATAGTAACGCCAATAGGGACTTTCCATTGACG

4501  TCAATGGGTGGAGTATTTACGGTAAACTGCCCACTTGGCAGTACATCAAGTGTATCATAT

4561  GCCAAGTACGCCCCCTATTGACGTCAATGACGGTAAATGGCCCGCCTGGCATTATGCCCA
                                                       SnaB I
4621  GTACATGACCTTATGGGACTTTCCTACTTGGCAGTACATCTACGTATTAGTCATCGCTAT

4681  TACCATGGTGATGCGGTTTTGGCAGTACATCAATGGGCGTGGATAGCGGTTTGACTCACG

4741  GGGATTTCCAAGTCTCCACCCCATTGACGTCAATGGGAGTTTGTTTTGGCACCAAAATCA

4801  ACGGGACTTTCCAAAATGTCGTAACAACTCCGCCCCATTGACGCAAATGGGCGGTAGGCG

4861  TGTACGGTGGGAGGTCTATATAAGCAGAGCTCGTTTAGTGAACCGTCAGATCGCCTGGAG

4921  ACGCCATCCACGCTGTTTTGACCTCCATAGAAGACACCGGGACCGATCCAGCCTCCGCGG

4981  CCGGGAACGGTGCATTGGAACGCGGATTCCCCGTGCCAAGAGTGACGTAAGTACCGCCTA

5041  TAGAGTCTATAGGCCCACCCCCTTGGCTTCTTATGCATGCTATACTGTTTTTGGCTTGGG
                                                  Bpu1102I
5101  GTCTATACACCCCCGCTTCCTCATGTTATAGGTGATGGTATAGCTTAGCCTATAGGTGTG
              Xcm I
5161  GGTTATTGACCATTATTGACCACTCCCCTATTGGTGACGATACTTTCCATTACTAATCCA

5221  TAACATGGCTCTTTGCCACAACTCTCTTTATTGGCTATATGCCAATACACTGTCCTTCAG

5281  AGACTGACACGGACTCTGTATTTTTACAGGATGGGGTCTCATTTATTATTTACAAATTCA

5341  CATATACAACACCACCGTCCCCAGTGCCCGCAGTTTTTATTAAACATAACGTGGGATCTC
                          BspE I
5401  CACGCGAATCTCGGGTACGTGTTCCGGACATGGGCTCTTCTCCGGTAGCGGCGGAGCTTC

5461  TACATCCGAGCCCTGCTCCCATGCCTCCAGCGACTCATGGTCGCTCGGCAGCTCCTTGCT

5521  CCTAACAGTGGAGGCCAGACTTAGGCACAGCACGATGCCCACCACCACCAGTGTGCCGCA

5581  CAAGGCCGTGGCGGTAGGGTATGTGTCTGAAAATGAGCTCggggagcgggcttgcaccgc
                                                        (Pvu II)
5641  tgacgcatttggaagacttaaggcagcggcagaagaagatgcaggcagctgagttgttgt
```

FIG.33D

```
5701 gttctgataagagtcagaggtaactcccgttgcggtgctgttaacggtggagggcagtgt 5761 agtctgagcagtactcgttgctgccgcgcgcgccaccagacataatagctgacagactaa
                                                         Mlu I
5821 cagactgttcctttccatgggtcttttctgcagtcaccgtccttgacACGCGTCTCGGGA Hind III
5881 AGCTTGCCGCCACCATGGACTGGACCTGGCGCGTGTTTTGCCTGCTCGCCGTGGCTCCTG
            M  D  W  T  W  R  V  F  C  L  L  A  V  A  P 5941 GGGCCCACAGCCAGGTGCAACTGGTGCAGTCCGGCGCCGAAGTGAAGAAACCCGGTGCTT
      G  A  H  S  Q  V  Q  L  V  Q  S  G  A  E  V  K  K  P  G  A
                       (Pvu II)  (Spe I)
6001 CCGTGAAAGTCAGCTGTAAAACTAGTAGATACACCTTCACTGAATACACCATACACTGGG
      S  V  K  V  S  C  K  T  S  R  Y  T  F  T  E  Y  T  I  H  W
                Msc I                           CDR 1
6061 TTAGACAGGCCCCTGGCCAAAGGCTGGAGTGGATAGGAGGTATTAATCCTAACAATGGTA
      V  R  Q  A  P  G  Q  R  L  E  W  I  G  G  I  N  P  N  N  G 6121 TTCCTAACTACAACCAGAAGTTCAAGGGCCGGGCCACCTTGACCGTAGGCAAGTCTGCCA
      I  P  N  Y  N  Q  K  F  K  G  R  A  T  L  T  V  G  K  S  A
               CDR 2
6181 GCACCGCCTACATGGAACTGTCCAGCCTGCGCTCCGAGGACACTGCAGTCTACTACTGCG
      S  T  A  Y  M  E  L  S  S  L  R  S  E  D  T  A  V  Y  Y  C 6241 CCAGAAGAAGAATCGCCTATGGTTACGACGAGGGCCATGCTATGGACTACTGGGGTCAAG
      A  R  R  R  I  A  Y  G  Y  D  E  G  H  A  M  D  Y  W  G  Q
                CDR 3                            BamH I
6301 GAACCCTTGTCACCGTCTCCTCAGGTGAGTGGATCCTCTGCGCCTGGGCCCAGCTCTGTC
      G  T  L  V  T  V  S  S 6361 CCACACCGCGGTCACATGGCACCACCTCTCTTGCAGCCTCCACCAAGGGCCCATCGGTCT
                                                 S  T  K  G  P  S  V 6421 TCCCCCTGGCACCCTCCTCCAAGAGCACCTCTGGGGGCACAGCGGCCCTGGGCTGCCTGG
      F  P  L  A  P  S  S  K  S  T  S  G  G  T  A  A  L  G  C  L
                                                       Age I
6481 TCAAGGACTACTTCCCCGAACCGGTGACGGTGTCGTGGAACTCAGGCGCCCTGACCAGCG
      V  K  D  Y  F  P  E  P  V  T  V  S  W  N  S  G  A  L  T  S 6541 GCGTGCACACCTTCCCGGCTGTCCTACAGTCCTCAGGACTCTACTCCCTCAGCAGCGTGG
      G  V  H  T  F  P  A  V  L  Q  S  S  G  L  Y  S  L  S  S  V
     BstE II
6601 TGACCGTGCCCTCCAGCAGCTTGGGCACCCAGACCTACATCTGCAACGTGAATCACAAGC
      V  T  V  P  S  S  S  L  G  T  Q  T  Y  I  C  N  V  N  H  K 6661 CCAGCAACACCAAGGTGGACAAGAAAGTTGAGCCCAAATCTTGTGACAAAACTCACACAT
      P  S  N  T  K  V  D  K  K  V  E  P  K  S  C  D  K  T  H  T
```

FIG.33E

```
6721 GCCCACCGTGCCCAGCACCTGAACTCCTGGGGGGACCGTCAGTCTTCCTCTTCCCCCCAA
      C  P  P  C  P  A  P  E  L  L  G  G  P  S  V  F  L  F  P  P

6781 AACCCAAGGACACCCTCATGATCTCCCGGACCCCTGAGGTCACATGCGTGGTGGTGGACG
      K  P  K  D  T  L  M  I  S  R  T  P  E  V  T  C  V  V  V  D

6841 TGAGCCACGAAGACCCTGAGGTCAAGTTCAACTGGTACGTGGACGGCGTGGAGGTGCATA
      V  S  H  E  D  P  E  V  K  F  N  W  Y  V  D  G  V  E  V  H

6901 ATGCCAAGACAAAGCCGCGGGAGGAGCAGTACAACAGCACGTACCGGGTGGTCAGCGTCC
      N  A  K  T  K  P  R  E  E  Q  Y  N  S  T  Y  R  V  V  S  V

6961 TCACCGTCCTGCACCAGGACTGGCTGAATGGCAAGGAGTACAAGTGCAAGGTCTCCAACA
      L  T  V  L  H  Q  D  W  L  N  G  K  E  Y  K  C  K  V  S  N

7021 AAGCCCTCCCAGCCCCCATCGAGAAAACCATCTCCAAAGCCAAAGGGCAGCCCCGAGAAC
      K  A  L  P  A  P  I  E  K  T  I  S  K  A  K  G  Q  P  R  E

7081 CACAGGTGTACACCCTGCCCCCATCCCGGGAGGAGATGACCAAGAACCAGGTCAGCCTGA
      P  Q  V  Y  T  L  P  P  S  R  E  E  M  T  K  N  Q  V  S  L

7141 CCTGCCTGGTCAAAGGCTTCTATCCCAGCGACATCGCCGTGGAGTGGGAGAGCAATGGGC
      T  C  L  V  K  G  F  Y  P  S  D  I  A  V  E  W  E  S  N  G

7201 AGCCGGAGAACAACTACAAGACCACGCCTCCCGTGCTGGACTCCGACGGCTCCTTCTTCC
      Q  P  E  N  N  Y  K  T  T  P  P  V  L  D  S  D  G  S  F  F

7261 TCTACAGCAAGCTCACCGTGGACAAGAGCAGGTGGCAGCAGGGGAACGTCTTCTCATGCT
      L  Y  S  K  L  T  V  D  K  S  R  W  Q  Q  G  N  V  F  S  C

7321 CCGTGATGCATGAGGCTCTGCACAACCACTACACGCAGAAGAGCCTCTCCCTGTCTCCGG
      S  V  M  H  E  A  L  H  N  H  Y  T  Q  K  S  L  S  L  S  P
                                                         NgoM I
7381 GTAAATGAGTGCGACGGCCGGCAAGCCCCGCTCCCCGGGCTCTCGCGGTCGCACGAGGAT
      G  K  *

7441 GCTTGGCACGTACCCCCTGTACATACTTCCCGGGCGCCCAGCATGGAAATAAAGCACCGG

7501 ATCTAATAAAAGATATTTATTTTCATTAGATATGTGTGTTGGTTTTTTGTGTGCAGTGCC

7561 TCTATCTGGAGGCCAGGTAGGGCTGGCCTTGGGGGAGGGGGAGGCCAGAATGACTCCAAG

7621 AGCTACAGGAAGGCAGGTCAGAGACCCCACTGGACAAACAGTGGCTGGACTCTGCACCAT

7681 AACACACAATCAACAGGGGAGTGAGCTGGaaatttgctagcgaattaattc 7731
```

FIG. 33F

```
                                    INTRON
3' end V gene  -------------------------------  5' end of CH1
ACC GTC TCC TCA G::GTGAGTGGATCC-(N)48-CCTCTCTTGCAG::CC-
 T   V   S   S splice donor site BamHI       splice acceptor site

-TCC ACC AAG GGC
  S   T   K   G                       ⇓

ACC GTC TCC TCA G::::CC TCC ACC AAG GGC
               T   V   S   S          S   T   K   G
                                ⇓
              ACC GTC TCC TCA GCC TCC ACC AAG GGC
               T   V   S   S   A   S   T   K   G
```

FIG.34A

```
                                    INTRON
3' end V gene  -------------------------------  5' end Kappa constant
GAA ATA AAA C::GTGAGTGGATCC-(N)108-CTTCTTTCCTCAG::GA-
 E   I   K splice donor site BamHI         splice acceptor site

-ACT GTG GCT GCA
  T   V   A   A

⇓
              GAA ATA AAA C::::GA ACT GTG GCT GCA
               E   I   K         T   V   A   A
                                ⇓
              GAA ATA AAA CGA ACT GTG GCT GCA
               E   I   K   R   T   V   A   A
```

FAPα-SPECIFIC ANTIBODY WITH IMPROVED PRODUCIBILITY

The present application claims the benefit of U.S. application Ser. No. 60/086,049, filed May 18, 1998, and EPO 98107925.4, filed Apr. 30, 1998.

BACKGROUND OF THE INVENTION

1. Field of the Invention

The present invention relates to antibody proteins that specifically bind fibroblast activation protein alpha (FAPα). The invention also relates to the use of said antibodies for diagnostic and therapeutic purposes and methods of producing said antibodies.

2. Related Art

The invasive growth of epithelial cancers is associated with a number of characteristic cellular and molecular changes in the supporting stroma. A highly consistent molecular trait of the reactive stroma of many types of epithelial cancer is induction of the fibroblast activation protein alpha (from now on referred to as FAP), a cell surface molecule of reactive stromal fibroblasts originally identified with monoclonal antibody F 19 (Garin-Chesa, P., et al., "Cell surface glycoprotein of reactive stromal fibroblasts as a potential antibody target in human epithelial cancers," Proc. Natl. Acad. Sci. 87:7235 (1990)). Since the FAP antigen is selectively expressed in the stroma of a range of epithelial carcinomas, independent of location and histological type, a FAP-targeting concept has been developed for imaging, diagnosis and treatment of epithelial cancers and certain other conditions. For this purpose a monoclonal antibody termed F19 that specifically binds to FAP was developed and described in U.S. Pat. No. 5,059,523 and WO 93/05804, which are hereby incorporated by reference in their entirety.

One serious problem that arises when using non-human antibodies for applications in vivo in humans is that they quickly raise a human anti-non-human response that reduces the efficacy of the antibody in patients and impairs continued administration. Humanization of non-human antibodies is commonly achieved in one of two ways: (1) by constructing non-human/human chimeric antibodies, wherein the non-human variable regions are joined to human constant regions (Boulianne, G. L., et al., "Production of functional chimeric mouse/human antibody," Nature 312:643 (1984)) or (2) by grafting the complementarity determining regions (CDRs) from the non-human variable regions to human variable regions and then joining these "reshaped human" variable regions to human constant regions (Riechmann L., et al., "Reshaping human antibodies for therapy," Nature 332:323 (1988)). Chimeric antibodies, although significantly better than mouse antibodies, can still elicit an anti-mouse response in humans (LoBuglio, A. F., et al., "Mouse/human chimeric monoclonal antibody in man: Kinetics and immune response," Proc. Natl. Acad. Sci. 86:4220 (1989)). CDR-grafted or reshaped human antibodies contain little or no protein sequences that can be identified as being derived from mouse antibodies. Although an antibody humanized by CDR-grafting may still be able to elicit some immune reactions, such as an anti-allotype or an anti-idiotypic response, as seen even with natural human antibodies, the CDR-grafted antibody will be significantly less immunogenic than a mouse antibody thus enabling a more prolonged treatment of patients.

Another serious limitation relating to the commercial use of antibodies for diagnosis, imaging and therapy is their producibility in large amounts. In many instances recombinant expression of native, chimeric and/or CDR-grafted antibodies in cell culture systems is poor. Factors contributing to poor producibility may include the choice of leader sequences and the choice of host cells for production as well as improper folding and reduced secretion. Improper folding can lead to poor assembly of heavy and light chains or a transport incompetent conformation that forbids secretion of one or both chains. It is generally accepted that the L-chain confers the ability of secretion of the assembled protein. In some instances multiple or even single substitutions can result in the increased producibility of antibodies.

Because of the clinical importance of specific immunological targeting in vitro and in vivo of specific disease-related antigens for diagnosis and therapy in humans, there is a growing need for antibodies that combine the features of antigen specificity, low immunogenicity and high producibility.

Therefore, the problem underlying the present invention was to provide antibody proteins that combine the properties of specific binding to FAP, low immunogenicity in humans, and high producibility in recombinant systems.

SUMMARY OF THE INVENTION

The technical problem is solved by the embodiments characterized in the claims.

The present invention provides new antibody proteins having the complementary determining regions of the monoclonal antibody F19 (ATCC Accession No. HB 8269), said new antibody proteins specifically binding to fibroblast activation protein (FAP), characterized in that they have framework modifications resulting in the improved producibility in host cells as compared to a chimeric antibody having the variable regions of F19 and foreign constant regions.

As used herein, an "antibody protein" is a protein with the antigen binding specificity of a monoclonal antibody.

"Complementarity determining regions of a monoclonal antibody" are understood to be those amino acid sequences involved in specific antigen binding according to Kabat (Kabat, E. A., et al., Sequences of Proteins of Immunological Interest, 5th Ed., NIH Publication No. 91-3242. U.S. Department of Health and Human Services, Public Health Service, National Institutes of Health, Bethesda, Md. (1991)) in connection with Chothia and Lesk (Chothia and Lesk, J. Mol. Biol., 196:901–917 (1987)).

As used herein, the term "framework modifications" refers to the exchange, deletion or addition of single or multiple amino acids in the variable regions surrounding the individual complementarity determining regions. Framework modifications may have an impact on the immunogenicity, producibility or binding specificity of an antibody protein. "Fibroblast activation protein (FAP)", also designated fibroblast activation protein alpha (FAPα), is a membrane-bound glycoprotein belonging to the serine protease gene family (WO 97/34927). No shed or secreted form of FAP is known. FAP can be characterized by its binding to the monoclonal antibody F19 (F19 is obtainable from the hybridoma cell line with the accession No. HB 8269 deposited at the ATCC).

The term "fibroblast activation protein specific binding" of an antibody protein is defined herein by its ability to specifically recognize and bind FAP-expressing human cells. The binding specificity of the proteins of the invention can be determined by standard methods for the evaluation of binding specificity such as described in an exemplary fashion in examples 6, 8 and 12.

The term "chimeric antibody" refers to an antibody protein having the light and heavy chain variable regions as described in FIGS. 17 and 18 and foreign constant regions. "Foreign constant regions" as defined herein are constant regions which are different from the constant regions of F19. For comparing an antibody protein of the invention to a chimeric antibody it is to be understood that such a chimeric antibody must contain the same constant regions as said antibody protein. For the purpose of demonstration and comparison alone the human constant heavy and light chains as described in FIGS. 19 to 22 are used in an exemplary fashion.

To provide the antibody proteins of the present invention, the nucleic acid sequences of the heavy and light chain genes of the murine antibody designated F19 were determined from RNA extracted from F19 hybridoma cells (ATCC Accession No. HB 8269).

In one embodiment the present invention relates to antibody proteins having the complementary determining regions of the monoclonal antibody F19 (ATCC Accession No. HB 8269), said new antibody proteins specifically binding to fibroblast activation protein (FAP), characterized in that they have framework modifications resulting in the improved producibility in host cells as compared to a chimeric antibody having the variable regions of F19 and foreign constant regions, wherein said antibody protein is derived from the murine antibody designated F19 (ATCC Accession No. HB 8269).

To generate humanized FAP-specific antibody proteins a chimeric antibody was constructed, having variable regions of the light and heavy chains of F19 and human light and heavy constant regions, respectively. The construction and production of chimeric mouse/human antibodies is well known (Boulianne et al. (1984), referenced above) and demonstrated in an exemplary fashion in examples 1 and 2.

The variable regions of the antibody proteins of the present invention are typically linked to at least a portion of the immunoglobulin constant region ($F_C$), typically that of a human immunoglobulin. Human constant region DNA sequences can be isolated in accordance with well-known procedures from a variety of human cells, but preferably immortalized B cells (see Kabat et al., supra, and WO 87/02671). Hence the antibody proteins of the invention may contain all or only a portion of the constant region as long as they exhibit specific binding to the FAP antigen. The choice of the type and extent of the constant region depends on whether effector functions like complement fixation or antibody dependent cellular toxicity are desired, and on the desired pharmacological properties of the antibody protein. The antibody protein of the invention will typically be a tetramer consisting of two light chain/heavy chain pairs, but may also be dimeric, i.e., consisting of a light chain/heavy chain pair, e.g., a Fab or Fv fragment.

Therefore, in a further embodiment the invention relates to antibody proteins according to the invention, characterized in that they have a variable light chain region and a variable heavy chain region, each joined to a human constant region.

In particular, the variable region of the light chain was joined to a human kappa constant region and the variable region of the heavy chain was joined to a human gamma-1 constant region. Other human constant regions for humanizing light and heavy chains are also available to the expert.

Therefore, in one particular embodiment the antibody proteins of the invention contain a human kappa constant region.

Also, in another particular embodiment the antibody proteins of the invention contain a human gamma-1 constant region.

One particular "chimeric F19 antibody" protein (cF19) consists of the light and heavy chain variable and constant regions described in FIGS. 17 to 22. cF19 demonstrates specific binding and high avidity to the FAP antigen. As demonstrated in example 2, the expression of cF19 in COS cells (cells derived from the kidney of an African green monkey) is poor, ranging from about 10 to 60 ng/ml, which is at least 10 fold less than most antibodies.

In an attempt to increase expression levels of cF19, the leader sequence of the F19 $V_L$ region was changed by substitution of proline to leucine at position 9. This single change in amino acid in the leader sequence resulted in at least doubling the amount of chimeric antibody produced in COS cells. For the expression of this particular chimeric antibody in COS cells the following mutated leader sequence of the light chain: MDSQAQVLMLLLLWVS-GTCG (SEQ ID NO:60, and the following leader sequence of the heavy chain: MGWSWVFLFLLSGTAGVLS (SEQ ID NO:61were used.

According to the invention the term "improved producibility" in host cells refers to the substantial improvement of expression levels and/or purified antibody yields when compared with the expression levels and/or antibody yields of a chimeric antibody without framework modifications as defined above. Two particular but not limiting examples for demonstrating improved producibility are exemplified for the COS cell expression system (in examples 2 and 5) and for the CHO cell expression system (in examples 10 and 11).

While the mutation of the leader sequence only leads to a doubling of the expression yield of the chimeric F19 antibody, a substantial improvement as defined herein refers to an improvement in expression level and/or purification yield of at least a factor of 10.

In a preferred embodiment, the invention refers to antibody proteins, characterized in that their expression levels in crude media samples as determined by ELISA and/or purified antibody yields exceed the expression levels and/or purification yields of the chimeric antibodies without framework modifications by at least a factor of 10.

In more preferred embodiment, the invention refers to antibody proteins, characterized in that their expression levels in crude media samples as determined by ELISA and/or purified antibody yields exceed the expression levels and/or purification yields of the chimeric antibodies without framework modifications by at least a factor of 20.

In a most preferred embodiment, antibody proteins, characterized in that their expression levels in crude media samples as determined by ELISA and/or purified antibody yields exceed the expression levels and/or purification yields of the chimeric antibodies without framework modifications by at least a factor of 100.

Improved producibility of the recombinant antibody proteins of the invention can be demonstrated for eukaryotic cells in general as shown for COS and CHO (Chinese hamster ovary derived cells) eukaryotic cells (see examples 5 and 11). In a further embodiment, the present invention relates to recombinant antibody proteins characterized in that they display improved producibility in eukaryotic cells.

In a preferred embodiment the present invention relates to antibody proteins, wherein said eukaryotic cell is a Chinese hamster ovary cell (CHO cell).

It was unexpectedly found that certain framework modifications of the light chain variable regions determine the improved producibility of the antibody proteins of the invention. Three versions of reshaped light chain variable regions, designated version A, B and C, as described in FIGS. 1 to 6, were prepared.

Light chain variable region versions A, B, and C demonstrate substantially improved producibility in CHO cells (see example 11). While light chain variable region versions A and C differ from light chain variable region version B by only two common amino acid residues they display an even further substantial improvement in producibility. There is at least another 10 fold difference in antibody secretion levels between the human reshaped F19 light chain version B and versions A or C. Reshaped human F19 light chain version A and B only differ in their amino acid sequences by two residues at positions 36 (Tyr to Phe mutation) and 87 (Tyr to Asp mutation) (nomenclature according to Kabat). This negative effect on the secretory capability of antibodies containing the light chain variable region version B could have been indirect if the Tyr to Asp and Tyr to Phe mutations, considered individually or together, merely caused improper folding of the protein. But this is unlikely to be the case since antigen binding assays show that immunoglobulins containing F19 light chain version B have similar avidities to those paired with F19 light chain version A or C, suggesting that they were not grossly misfolded.

Residue 87 in reshaped human F19 light chain version B seems particularly responsible for the reduction of secretion when compared to versions A and C.

In a preferred embodiment, the present invention relates to antibody proteins according to the invention, wherein the amino acid in Kabat position 87 of the light chain region is not asparagine.

In a more preferred embodiment, the invention relates to antibody proteins according to the invention, wherein the amino acid in Kabat position 87 of the light chain region is selected from aromatic or aliphatic amino acids.

In a most preferred embodiment, the present invention relates to antibody proteins according to the invention, wherein the aromatic amino acid in Kabat position 87 of the light chain region is a tyrosine or phenylalanine.

In a further embodiment, the present invention also pertains to antibody proteins according to the invention, wherein the amino acid in Kabat position 36 of the light chain region is selected from aromatic amino acids.

In a particular embodiment the invention relates to the specific antibody proteins that may be prepared from the individually disclosed reshaped variable regions of the light and heavy chains.

Especially light chain variable region versions A and C are particularly suitable to practice the invention because of their exceptionally high producibility, while retaining full FAP-binding specificity and achieving low immunogenicity. This holds especially true when compared to the chimeric antibody having the variable regions of F19 and the same constant regions but also when compared to light chain version B.

Therefore, in one embodiment the present invention relates to antibody proteins that contain the variable region of the light chain as set forth in SEQ ID NO:2.

In a further embodiment the invention also relates to antibody proteins, characterized in that the variable region of the light chain is encoded by a nucleotide sequence as set forth in SEQ ID NO:1.

In one embodiment the present invention relates to antibody proteins that contain the variable region of the light chain as set forth in SEQ ID NO:6.

In a further embodiment the invention also relates to antibody proteins characterized in that the variable region of the light chain is encoded by a nucleotide sequence as set forth in SEQ ID NO:5.

The present invention also discloses several different variable regions of the heavy chain that work particularly well with the variable regions of the light chain versions A and C in terms of improved producibility.

In one embodiment the invention relates to antibody proteins containing a variable region of the heavy chain as set forth in any one of SEQ ID NOS:8, 10, 12 and 14.

In another embodiment the invention relates to antibody proteins characterized in that the variable region of the heavy chain is encoded by a nucleotide sequence as set forth in any one of SEQ ID NOS:7, 9, 11 and 13.

In a very particular embodiment the invention relates to antibody proteins containing the variable region of the light chain as set forth in SEQ ID NO:2 and the variable region of the heavy chain as set forth in SEQ ID NO:12. Most preferably, this antibody protein additionally contains the constant region of the light chain as set forth in SEQ ID NO:20 and the constant region of the heavy chain as set forth in SEQ ID NO:22.

Thus a further aspect of the present invention is an antibody protein containing an amino acid sequence as set forth in SEQ ID NO:2. More preferably, such an antibody protein further contains an amino acid sequence as set forth in SEQ ID NO:12. More preferably, said antibody protein further contains an amino acid sequence as set forth in SEQ ID NO:20 and an amino acid sequence as set forth in SEQ ID NO:22. A further aspect of the invention is an antibody protein as described in this paragraph which is conjugated to a radioisotope, preferably $^{131}$I, $^{125}$I, $^{186}$Re, $^{188}$Re, or $^{90}$Y. An additional aspect of the present invention is a DNA molecule coding for an antibody protein as described in this paragraph. A further aspect of the invention is a host cell carrying such a DNA molecule. Accordingly, a further aspect of the invention is a method of producing an antibody protein as described in this paragraph, said method comprising the steps of cultivating such a host cell under conditions where said antibody protein is expressed by said host cell, and isolating said protein. A further aspect of the invention is a pharmaceutical composition comprising an antibody protein of the present invention and a pharmaceutically acceptable carrier.

In a further particular embodiment the invention relates to antibody proteins characterized in that the variable region of the light chain is encoded by a nucleotide sequence as set forth in SEQ ID NO:1 and the variable region of the heavy chain is encoded by a nucleotide sequence as set forth in SEQ ID NO:11.

In a further particular embodiment the invention relates to antibody proteins containing the variable region of the light chain as set forth in SEQ ID NO:2 and the variable region of the heavy chain as set forth in SEQ ID NO:8.

In a further particular embodiment the invention relates to antibody proteins characterized in that the variable region of the light chain is encoded by a nucleotide sequence as set forth in SEQ ID NO:1 and the variable region of the heavy chain is encoded by a nucleotide sequence as set forth in SEQ ID NO:7.

Humanization of the variable region of a murine antibody may be achieved employing methods known in the art. EP 0230400 discloses grafting of the CDRs of a murine variable region into the framework of a human variable region. WO 90/07861 discloses methods of reshaping a CDR-grafted variable region by introducing additional framework modifications. WO 92/11018 discloses methods of producing humanized Ig combining donor CDRs with an acceptor framework that has a high homology to the donor framework. WO 92/05274 discloses the preparation of framework mutated antibodies starting from a murine antibody. Further prior art references related to humanization of murine monoclonal antibodies are EP 0368684; EP 0438310; WO 92/07075 or WO 92/22653. Thus, the expert can produce the antibodies of the present invention starting from the publicly available murine monoclonal antibody F19 and employing techniques known in the art, e.g., from WO 92/05274; DNA molecules coding for the antibody proteins of the present invention may of course also be obtained by state-of-the-art synthetic procedures, e.g., by chemical synthesis of appropriate oligonucleotides and subsequent ligation and amplification procedures (see e.g., Frank et al., *Methods Enzymol.* 154:221–249 (1987)).

In a further aspect, the present invention relates to nucleic acid molecules containing the coding information for the antibody proteins according to the invention as disclosed above. Preferably, a nucleic acid molecule according to the present invention is a nucleic acid molecule containing a nucleotide sequence selected from SEQ ID NOS:1, 3, 5, 7, 9, 11, 13 or 15.

A further aspect of the present invention is a recombinant DNA vector containing the nucleotide sequence of any one of the above-mentioned nucleic acids, especially when said nucleotide sequence is operationally linked to an expression control sequence as in expression vectors. Preferred is a recombinant DNA vector, said vector being an expression vector.

A further aspect of the present invention is a host cell carrying a vector as described, especially an expression vector. Such a host cell can be a prokaryotic or eukaryotic cell. Preferably, such a host cell is a eukaryotic cell, a yeast cell, or a mammalian cell. More preferably, said host cell is a CHO (Chinese hamster ovary) cell or a COS cell.

Accordingly, a still further aspect of the present invention is a method of producing antibody proteins according to the invention. Such a method comprises the steps of:

(a) cultivating a host cell as described above under conditions where said antibody protein is expressed by said host cell, and (b) isolating said antibody protein.

Mammalian host cells, preferably CHO or COS cells are preferred. Host cells for producing the antibody proteins of the invention may be transfected with a single vector containing the expression units for both, the light and the heavy chain (see, e.g., WO 94/11523). In one particular embodiment the method of producing antibody proteins according to the invention pertains to host cells, wherein said host cells are cotransfected with two plasmids carrying the expression units for the light and heavy chains respectively (see, e.g., EP 0481790).

The antibody proteins of the invention provide a highly specific tool for targeting therapeutic agents to the FAP antigen. Therefore, in a further aspect, the invention relates to antibody proteins according to the invention, wherein said antibody protein is conjugated to a therapeutic agent. Of the many therapeutic agents known in the art, therapeutic agents selected from the group consisting of radioisotopes, toxins, toxoids, inflammatogenic agents, enzymes, antisense molecules, peptides, cytokines, and chemotherapeutic agents are preferred. Among the radioisotopes, gamma, beta and alpha-emitting radioisotopes may be used as a therapeutic agent. β-emitting radioisotopes are preferred as therapeutic radioisotopes. $^{186}$Rhenium, $^{188}$Rhenium, $^{131}$Iodine and $^{90}$Yttrium have been proven to be particularly useful β-emitting isotopes to achieve localized irradiation and destruction of malignant tumor cells. Therefore, radioisotopes selected from the group consisting of $^{186}$Rhenium, $^{188}$Rhenium, $^{131}$Iodine and $^{90}$Yttrium are particularly preferred as therapeutic agents conjugated to the antibody proteins of the invention. For example, for the radioiodination of an antibody of the invention, a method as disclosed in WO 93/05804, may be employed.

A further aspect of the present invention pertains to antibody proteins according to the invention, characterized in that they are labelled. Such an FAP-specific labelled antibody allows for the localization and/or detection of the FAP antigen in vitro and/or in vivo. A label is defined as a marker that may be directly or indirectly detectable. An indirect marker is defined as a marker that cannot be detected by itself but needs a further directly detectable marker specific for the indirect marker. Preferred labels for practicing the invention are detectable markers. From the large variety of detectable markers, a detectable marker selected from the group consisting of enzymes, dyes, radioisotopes, digoxygenin, and biotin is most preferred.

A further aspect of the present invention relates to antibody proteins according to the invention, characterized in that they are conjugated to an imageable agent. A large variety of imageable agents, especially radioisotopes, are available from the state of the art. For practicing the invention gamma-emitting isotopes are more preferred. Most preferred is $^{125}$Iodine.

One aspect of the present invention relates to pharmaceutical compositions containing an antibody protein according to the present invention as described above and a pharmaceutically acceptable carrier. Such pharmaceutical compositions are useful for treating tumors, wherein said tumors are associated with activated stromal fibroblasts. There are two possible effector principles for an anti-tumor stroma immunotherapy that may act synergistically: (a) an unmodified (unconjugated, "naked") antibody according to the invention may induce immune destruction or inflammatory reactions in the tumor stroma while (b) an antibody conjugated to a therapeutic agent, such as for example, a radioisotope or other toxic substance, may achieve localized irradiation and destruction of the malignant tumor cells. Accordingly, a further aspect of the present invention is the use of an antibody protein as described for the manufacture of a pharmaceutical composition, especially for the treatment of tumors.

One further embodiment are pharmaceutical compositions containing an antibody protein according to the invention conjugated to a therapeutic agent as described above and a pharmaceutically acceptable carrier useful for treating tumors, wherein said tumors are associated with activated stromal fibroblasts. Another embodiment pertains to pharmaceutical compositions containing an antibody protein according to the present invention conjugated to an imageable agent as described above and a pharmaceutically acceptable carrier useful for imaging the presence of activated stromal fibroblasts in a healing wound, inflamed skin or a tumor, in a human patient. A most preferred embodiment relates to the pharmaceutical compositions mentioned above, wherein said tumors are tumors selected from the cancer group consisting of colorectal cancers, non-small cell lung cancers, breast cancers, head and neck cancer, ovarian cancers, lung cancers, invasive bladder cancers, pancreatic cancers and cancers metastatic of the brain.

In an animal or human body, it can prove advantageous to apply the pharmaceutical compositions as described above via an intravenous or other route, e.g., systemically, locally or topically to the tissue or organ of interest, depending on the type and origin of the disease or problem treated, e.g., a tumor. For example, a systemic mode of action is desired when different organs or organ systems are in need of treatment as in e.g., systemic autoimmune diseases, or allergies, or transplantations of foreign organs or tissues, or tumors that are diffuse or difficult to localize. A local mode of action would be considered when only local manifestations of neoplastic or immunologic action are expected, such as, for example local tumors.

The antibody proteins of the present invention may be applied by different routes of application known to the expert, notably intravenous injection or direct injection into target tissues. For systemic application, the intravenous, intravascular, intramuscular, intraarterial, intraperitoneal, oral, or intrathecal routes are preferred. A more local application can be effected subcutaneously, intracutaneously, intracardially, intralobally, intramedullarly, intrapulmonarily or directly in or near the tissue to be treated (connective-, bone-, muscle-, nerve-, epithelial tissue). Depending on the desired duration and effectiveness of the treatment, pharmaceutical antibody compositions may be administered once or several times, also intermittently, for instance on a daily basis for several days, weeks or months and in different dosages.

For preparing suitable antibody preparations for the applications described above, the expert may use known injectable, physiologically acceptable sterile solutions. For preparing a ready-to-use solution for parenteral injection or infusion, aqueous isotonic solutions, such as, e.g., saline or corresponding plasma protein solutions are readily available. The pharmaceutical compositions may be present as lyophylisates or dry preparations, which can be reconstituted with a known injectable solution directly before use under sterile conditions, e.g., as a kit of parts. The final preparation of the antibody compositions of the present invention are prepared for injection, infusion or perfusion by mixing purified antibodies according to the invention with a sterile physiologically acceptable solution, that may be supplemented with known carrier substances or/and additives (e.g., serum albumin, dextrose, sodium bisulfite and EDTA).

The amount of the antibody applied depends on the nature of the disease. In cancer patients, the applied dose of a 'naked' antibody may be between 0.1 and 100 mg/m$^2$, preferably between 5 and 50 mg/m$^2$ per application. For radiolabeled antibodies, e.g., with iodine-131, the maximally tolerated dose (MTD) has to be determined which must not be exceeded in therapeutic settings. Application of radiolabeled antibody to cancer patients may then be carried out by repeated (monthly or weekly) intravenous infusion of a dose which is below the MTD (see, e.g., Welt et al., *J. Clin. Oncol.* 12:1193–1203 (1994)).

Furthermore, one aspect of the present invention relates to the use of the antibody proteins according to the invention for the treatment of cancer. In a preferred embodiment the present invention relates to the use of antibody proteins according to the invention conjugated to a therapeutic agent as described above for the treatment of cancer. In another preferred embodiment the present invention relates to the use of antibody proteins according to the invention conjugated to an imageable agent for imaging activated stromal fibroblasts. In a further preferred embodiment the present invention relates to the use of labelled antibody proteins according to the invention for detecting the presence of activated stromal fibroblasts in a sample.

One aspect of the invention relates to a method of treating tumors, wherein the tumor is associated with activated stromal fibroblasts capable of specifically forming a complex with antibody proteins according to the invention, present as naked/unmodified antibodies, modified antibody proteins, such as, e.g., fusion proteins, or antibody proteins conjugated to a therapeutic agent, which comprises contacting the tumor with an effective amount of said antibodies. In a preferred embodiment the present invention relates to a method of treating tumors as mentioned above, wherein the tumor is a tumor having cancer cells selected from the cancer group consisting of colorectal cancers, non-small cell lung cancers, breast cancers, head and neck cancer, ovarian cancers, lung cancers, invasive bladder cancers, pancreatic cancers and metastatic cancers of the brain. The method of treating tumors as described above may be effected in vitro or in vivo.

A further aspect of the invention relates to a method of detecting the presence of activated stromal fibroblasts in wound healing, inflammation or in tumors, characterized in that (a) a sample, possibly containing activated stromal fibroblasts, is contacted with an antibody protein according to the invention under conditions suitable for the formation of a complex between said antibody and antigen, (b) detecting the presence of said complex, thereby detecting the presence of activated stromal fibroblasts in wound healing, inflammation or a tumor.

In a preferred embodiment, the present invention relates to a method of detecting the presence of activated stromal fibroblasts in a tumor, wherein the tumor is a tumor having cancer cells selected from the cancer group consisting of colorectal cancers, non-small cell lung cancers, breast cancers, head and neck cancer, ovarian cancers, lung cancers, bladder cancers, pancreatic cancers and metastatic cancers of the brain. Most preferred antibody proteins of the invention are those which are characterized in that they are labelled as mentioned above.

A further aspect of the invention relates to a method of imaging the presence of activated stromal fibroblasts in a healing wound, inflamed tissue (rheumatoid arthritis and cirrhosis are also positive) or a tumor, in a human patient, characterized in that (a) an antibody protein according to the present invention conjugated to an imageable agent is administered to a human patient under conditions suitable for the formation of an antibody-antigen complex, (b) imaging any complex formed in this manner, (c) thereby imaging the presence of activated stromal fibroblasts in a human patient.

In a preferred embodiment the present invention relates to a method of imaging the presence of activated stromal fibroblasts as described above in tumors, wherein the tumor is a tumor having cancer cells selected from the cancer group consisting of colorectal cancers, non-small cell lung cancers, breast cancers, head and neck cancer, ovarian cancers, lung cancers, bladder cancers, pancreatic cancers and metastatic cancers of the brain.

In a further aspect the present invention relates to a method of detecting tumor-stroma, characterized in that (a) a suitable sample is contacted with an antibody protein according to the present invention, under conditions suitable for the formation of an antibody-antigen complex, (b) detecting the presence of any complex so formed, (c) relating the presence of said complex to the presence of tumor-stroma.

Antibody proteins for practicing the invention are preferably labeled with a detectable marker.

In a further aspect the present invention relates to a method of imaging tumor-stroma in a human patient, which comprises
(a) administering to the patient an antibody according to the invention conjugated to an imageable agent as described above under conditions suitable for the formation of an antibody-antigen complex,
(b) imaging any complex so formed, and thereby imaging the presence of tumor-stroma in a human patient.

BRIEF DESCRIPTION OF THE FIGURES

FIG. 1. DNA sequence of F19 human reshaped light chain variable region version A (hF19L$_A$) SEQ ID NO:1.

FIG. 2. Amino acid sequence of F19 human reshaped light chain variable region version A (hF19L$_A$) SEQ ID NO:2.

FIG. 3. DNA sequence of F19 human reshaped light chain variable region version B (hF19L$_B$) SEQ ID NO:3. Nucleotides differing from version A are underlined and in bold type.

FIG. 4. Amino acid sequence of F19 human reshaped light chain variable region version B (hF19L$_B$) SEQ ID NO:4. Amino acids differing from version A are underlined and in bold type.

FIG. 5. DNA sequence of F19 human reshaped light chain variable region version C (hF19L$_C$) SEQ ID NO:5. Nucleotides differing from version A are underlined and in bold type.

FIG. 6. Amino acid sequence of F19 human reshaped light chain variable region version C (hF19L$_C$) SEQ ID NO:6. Amino acids differing from version A are underlined and in bold type.

FIG. 7. DNA sequence of F19 human reshaped variable region heavy chain version A (hF19H$_A$) SEQ ID NO:7.

FIG. 8. Amino acid sequence of F19 human reshaped heavy chain variable region version A (hF19H$_A$) SEQ ID NO:8

FIG. 9. DNA sequence of F19 human reshaped heavy chain variable region version B (hF19H$_B$) SEQ ID NO:9. Nucleotides differing from version A are underlined and in bold type.

FIG. 10. Amino acid sequence of F19 human reshaped heavy chain variable region version B (hF19H$_B$) SEQ ID NO:10. Amino acids differing from version A are underlined and in bold type.

FIG. 11. DNA sequence of F19 human reshaped heavy chain variable region version C (hF19H$_C$) SEQ ID NO:11. Nucleotides differing from version A are underlined and in bold type.

FIG. 12. Amino acid sequence of F19 human reshaped heavy chain variable region version C (hF19H$_C$) SEQ ID NO:12. Amino acids differing from version A are underlined and in bold type.

FIG. 13. DNA sequence of F19 human reshaped heavy chain variable region version D (hF19H$_D$) SEQ ID NO:13. Nucleotides differing from version A are underlined and in bold type.

FIG. 14. Amino acid sequence of F19 human reshaped heavy chain variable region version D (hF19H$_D$) SEQ ID NO:14. Amino acids differing from version A are underlined and in bold type.

FIG. 15. DNA sequence of F19 human reshaped heavy chain variable region version E (hF19H$_E$) SEQ ID NO:15. Nucleotides differing from version A are underlined and in bold type.

FIG. 16. Amino acid sequence of F19 human reshaped heavy chain variable region version E (hF19H$_E$) SEQ ID NO:16. Amino acids differing from version A are underlined and in bold type.

FIG. 17. Amino acid sequence of F19 chimeric light chain variable region (chF19LC) SEQ ID NO:17.

FIG. 18. Amino acid sequence of F19 chimeric heavy chain variable region (chF19HC) SEQ ID NO:18.

FIG. 19. DNA sequence of human kappa light constant chain SEQ ID NO:19.

FIG. 20. Amino acid sequence of human light constant chain SEQ ID NO:20.

FIGS. 21A and 21B. DNA sequence of human heavy constant chain SEQ ID NO:21.

FIG. 22. Amino acid sequence of human heavy constant chain SEQ ID NO:22.

Figure 23A:
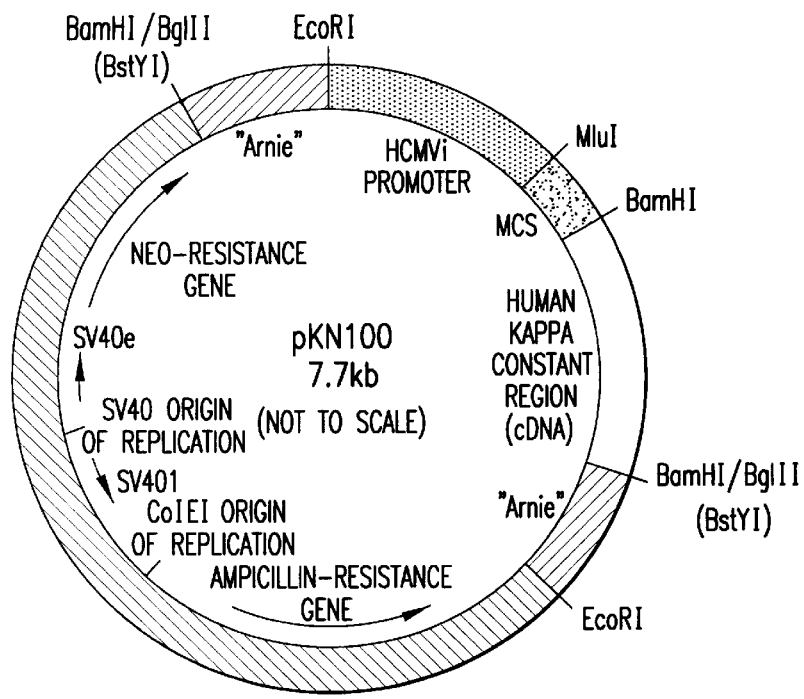
FIGS. 23A and 23B. Mammalian cell expression vectors used to produce chimeric and reshaped human antibodies with human kappa light chains and human gamma-1 heavy chains.

A. Light chain expression vector: pKN100
B. Heavy chain expression vector: pG1D105

FIG. 24. DNA and amino acid sequences of mouse F19 light chain variable region (SEQ ID NOS:23 and 24, respectively) as modified for use in the construction of chimeric F19 light chain. Restriction sites are indicated by bold letters. The Kozak sequence, CDRs 1 to 3 and the splice donor site are underlined.

FIGS. 25A and 25B. DNA and amino acid sequences of mouse F19 heavy chain variable region (SEQ ID NOS:25 and 26, respectively) as modified for use in the construction of chimeric F19 heavy chain. Restriction sites are indicated by bold letters. The Kozak sequence and the splice donor site are underlined.

FIG. 26A–26H. DNA sequence of F19 chimeric antibody (SEQ ID NO:27); amino acid sequence (SEQ ID NO:28) cloned into pKN100 mammalian expression vector. Restriction sites are indicated by bold letters and underlined. CDRs 1 to 3 and the splice donor site are underlined. This is the DNA sequence of the mouse F19 light chain inside the pKN100 eukaryotic expression vector. This vector has a cDNA version of the human kappa constant region gene (allotype Km(3)) terminated by a strong artificial termination sequence. In addition, the Neo selection gene is also terminated by this artificial sequence and is also in the same orientation as the kappa light chain expression cassette.

The essential components of the pKN100 eukaryotic expression vector are:

| | | |
|---|---|---|
| 1–6 | = | EcoRI site |
| 7–1571 | = | HCMVi promoter/enhancer |
| 583–587 | = | TATAA box |
| 610 | = | Start of transcription |
| 728–736 | = | Splice donor site |
| 731 | = | Beginning of intron |
| 1557 | = | End of intron |
| 1544–1558 | = | Splice acceptor site |
| 1590–1598 | = | Kozak sequence |
| 1599–1658 | = | peptide leader sequence |
| 1659–1997 | = | mouse F19 light chain |

-continued

| | | |
|---|---|---|
| 1996–2004 | = | splice donor site |
| 2011–2657 | = | cDNA copy of human Kappa constant region (Km(3)) gene |
| 2664–2880 | = | Artificial spaC2 termination sequence |
| 2887–7845 | = | This is the pSV2neo vector DNA fragment comprising of the Amp-resistance gene (in the opposite orientation), the ColEI and SV40 origins of replication and the Neo-resistance gene (in the same orientation as the HCMVi-KCT cassette) |
| 7852–8068 | = | Artificial spaC2 termination signal |

This sequence ends immediately upstream of the EcoRI site (position 1–6) at the beginning of the sequence. As a vector this DNA sequence would be circular.

FIGS. 27A–27G. DNA sequence of F19 chimeric antibody (SEQ ID NO:29); amino acid sequence (SEQ ID NO:30) cloned into pg1d105 mammalian expression vector. Restriction sites are indicated by bold letters and underlined. CDRs 1 to 3 and the splice donor site are underlined. This is the DNA sequence of the eukaryotic expression vector pG1D105 containing the mouse F19 heavy chain variable region. This vector contains a cDNA version of the human gamma-1 constant region (allotype G1m (non-a, -z, -x) also known as Gm1(17) allotype).

The essential components of the construct are:

| | | |
|---|---|---|
| 1–2501 | = | pBR322 based sequence including Ampicillin resistance gene and ColEI origin plus the SV40 origin and the crippled SV40 early promoter |
| 2502–3226 | = | dhfr gene |
| 3233–4073 | = | SV40 poly A sequence etc. |
| 4074–4079 | = | ligated BamHI and BglII site (BstYI) |
| 4080–4302 | = | SPA site plus C2 termination signal |
| 4303–5867 | = | HCMVi promoter |
| 5879–5885 | = | unique HindIII restriction site for cloning of immunoglobulin variable genes |
| 5886–5894 | = | Kozak sequence |
| 5895–5951 | = | signal peptide |
| 5952–6323 | = | mouse F19 heavy chain |
| 6323–6330 | = | splice donor site |
| 6331–6336 | = | unique BamHI restriction site for cloning of immunoglobulin variable genes |
| 6337–7388 | = | cDNA copy of human gamma-1 constant regions preceded by a 62 bp intron |
| 7389–7709 | = | Arnie termination sequence |

The human gamma-1 constant region used in this construct has a G1m (non-a, -z, -x) also known as Gm1 (17) allotype which is defined by a glutamic acid (E) residue at position 356 (according to Eu numbering), and a methionine (M) residue at position 358 (according to Eu numbering) and a lysine (K) residue at position 214 (according to Eu numbering). These three residues are underlined in the sequence above.

Figure 28:
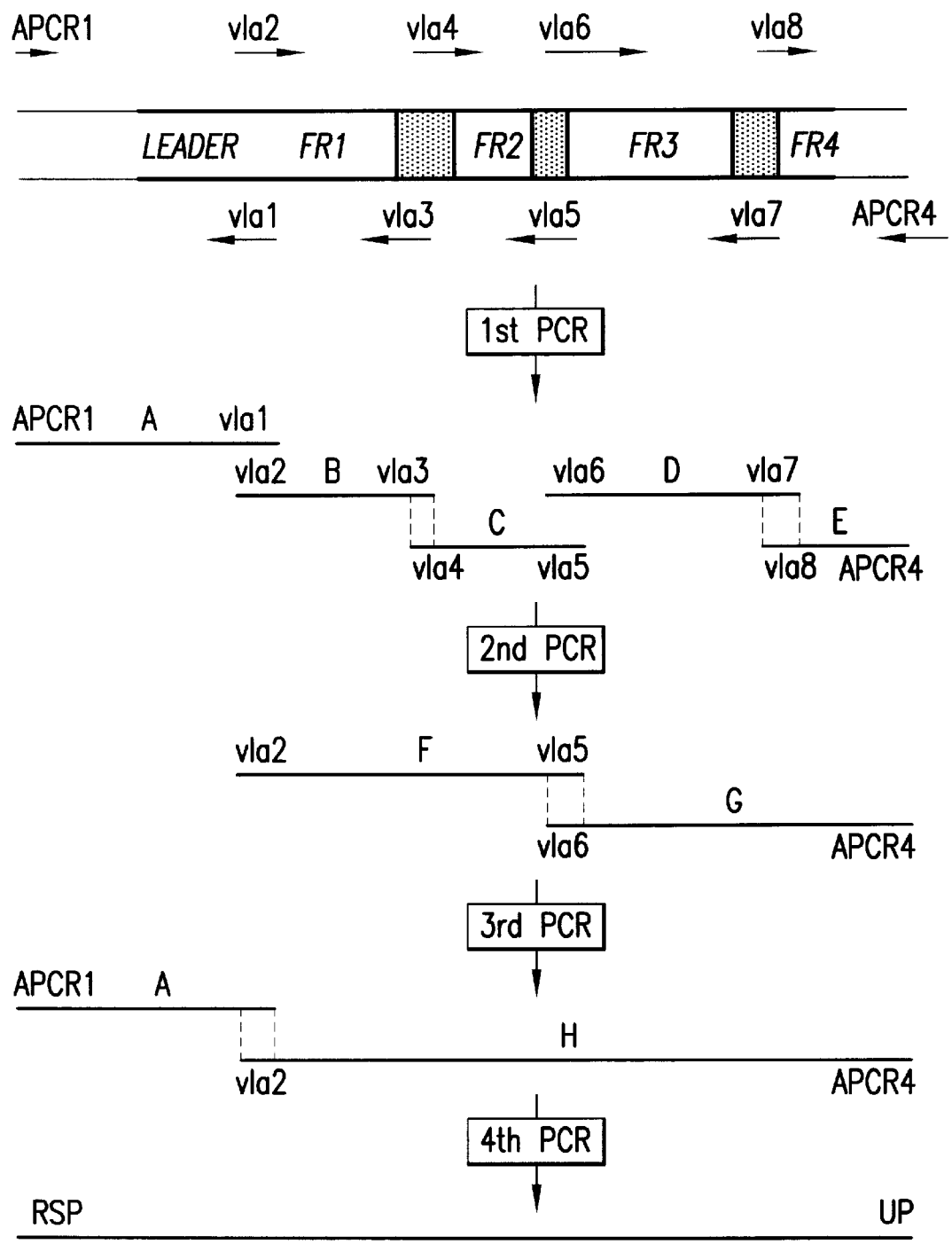

FIG. 28. PCR-based method for the construction of human reshaped F19 light chain. This figure provides a schematic overview of the strategy of construction. The dotted lines indicate a complementary sequence of at least 21 bases between the primers.

FIGS. 29A and 29B. Nucleotide and deduced amino acid sequences of reshaped human F19 light chain variable regions version A (SEQ ID NOS:31 and 32), B (SEQ ID NOS:33 and 102) and C (SEQ ID NOS:34 and 103). Nucleotide and deduced amino acid sequences are aligned and compared with that of version A, dashes indicate nucleotide identity, dots indicate amino acid identity with this sequence. Amino acids are numbered according to Kabat et al. (1991). The locations of CDRs are indicated in boxes.

FIGS. 30A–30G. DNA sequence of F19 LA (human reshaped light chain version A) (SEQ ID NO:35); amino acid sequence (SEQ ID NO:36) cloned into pKN100 mammalian expression vector. Restriction sites are indicated by bold letters and underlined. CDRs 1 to 3 and the splice donor site are underlined. This is the DNA sequence of the reshaped F19 light chain version. A cloned into pKN100 eukaryotic expression vector. This vector has a cDNA version of the human kappa constant region gene (allotype Km(3)) terminated by a strong artificial termination sequence. In addition, the Neo selection gene is also terminated by this artificial sequence and is also in the same orientation as the kappa light chain expression cassette.

The components of the vector are:

| | | |
|---|---|---|
| 7–1571 | = | HCMVi promoter/enhancer |
| 583–587 | = | TATAA box. |
| 610 | = | Start of transcription. |
| 728–736 | = | Splice donor site. |
| 731 | = | Beginning of intron. |
| 1557 | = | End of intron. |
| 1544–1558 | = | Splice acceptor site. |
| 1590–1598 | = | Kozak sequence |
| 1599–1658 | = | peptide leader sequence |
| 1659–1997 | = | reshaped F19 light chain version A |
| 1996–2004 | = | splice donor site |
| 2011–2657 | = | cDNA copy of human kappa constant region (Km(3)) gene. |
| 2664–2880 | = | Artificial spaC2 termination sequence. |
| 2887–7845 | = | This is the pSV2neo vector DNA fragment comprising of the Amp-resistance gene (in the opposite orientation), the ColEI and SV40 origins of replication and the Neo-resistance gene (in the same orientation as the HCMVi-KCT cassette). |
| 7852–8068 | = | Artificial spaC2 termination signal. |

This sequence ends immediately upstream of the EcoRI site (position 1–6) at the beginning of the sequence below. As a vector this DNA sequence would be circular.

Figure 31:
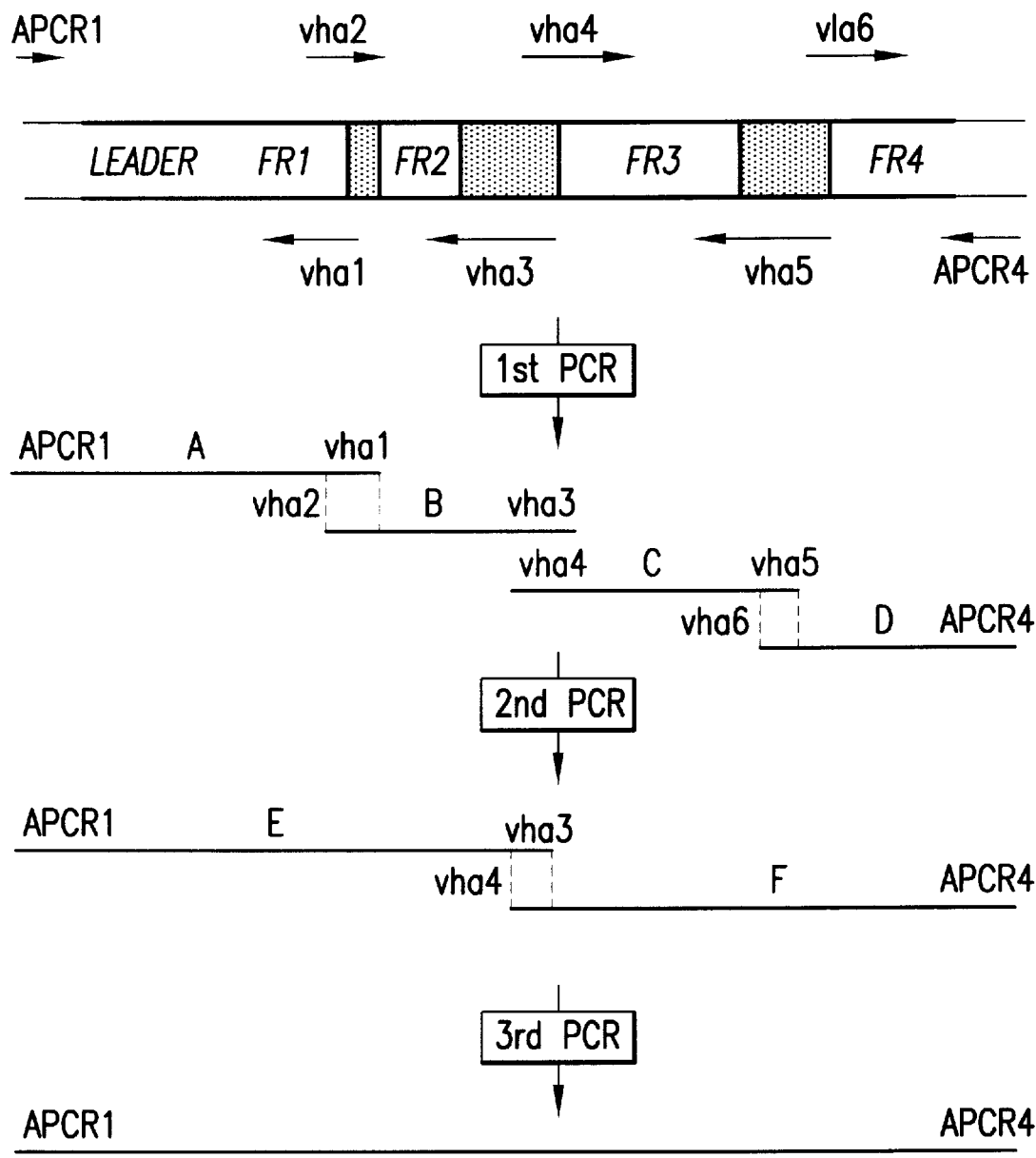

FIG. 31. PCR-based method for the construction of human reshaped F19 heavy chain. This figure provides a schematic overview of the strategy of construction. The dotted lines indicate a complementary sequence of at least 21 bases between the primers.

Figure 32A:
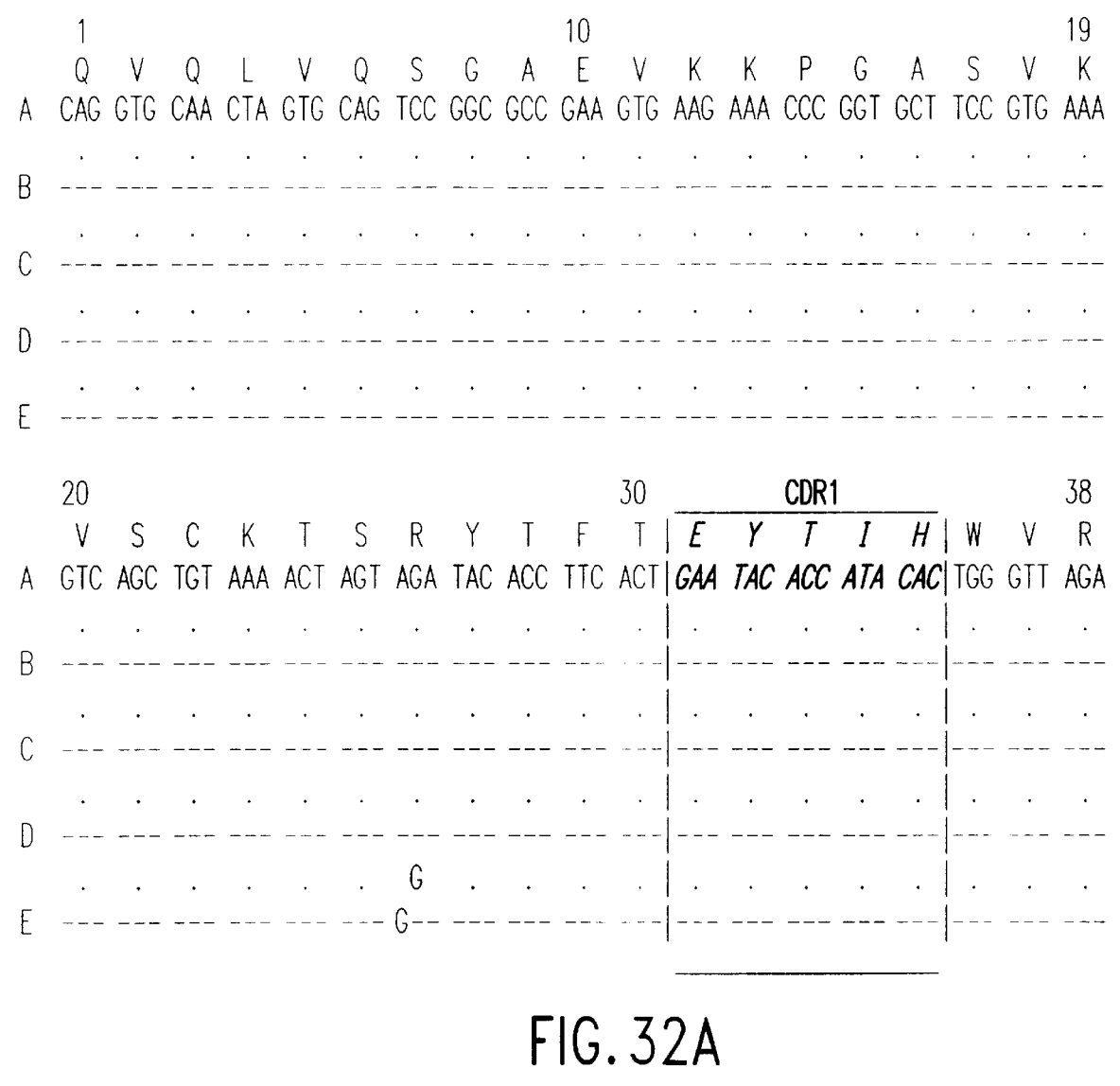
Figure 32B:
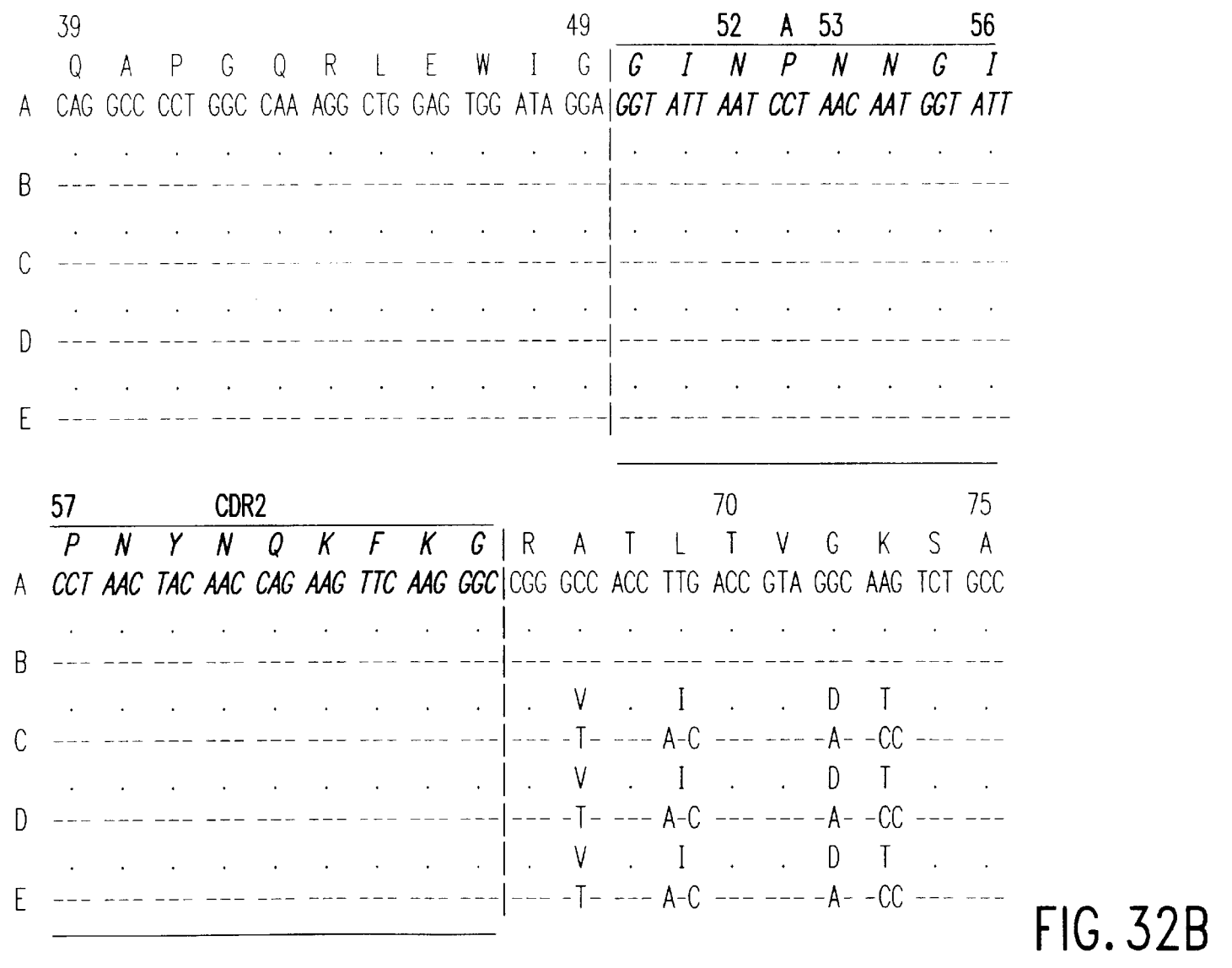
Figure 32C:
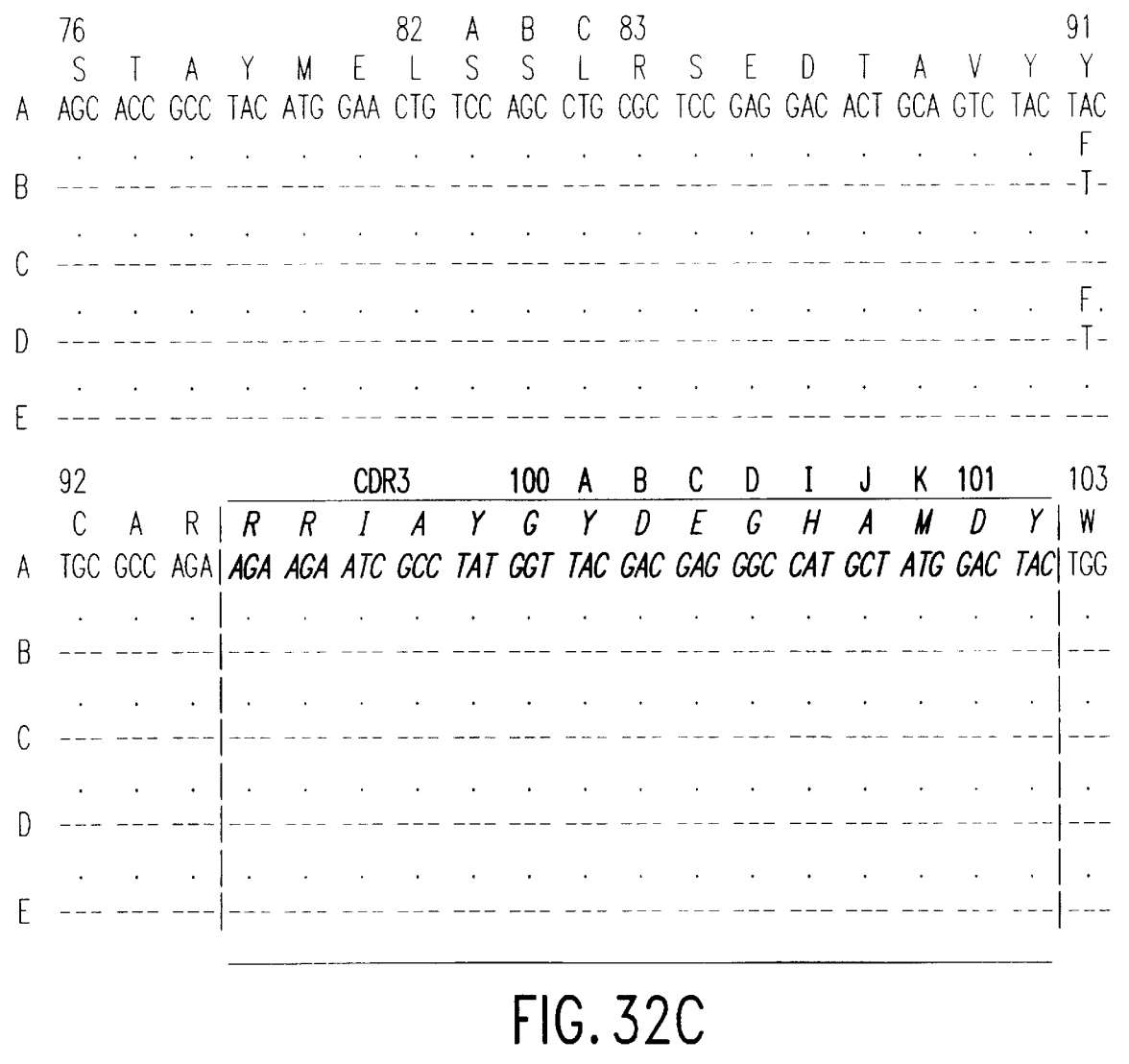

FIGS. 32A–32D. Nucleotide and deduced amino acid sequences of reshaped human F19 heavy chain variable region versions a to e (SEQ ID NOS:37, 104, 105, 106, 107, respectively); amino acid sequences (SEQ ID NOS:38, 39, 40, 108, 41, respectively). Nucleotide and deduced amino acid sequences are aligned and compared with that of version A, dashes indicate nucleotide identity, dots indicate amino acid identity with this sequence. Amino acids are numbered according to Kabat et al. (1991). The location of CDRs is indicated by boxes.

FIGS. 33A–33F. DNA sequence of F19Ha (human reshaped heavy chain version a) (SEQ ID NO:42); amino acid sequence (SEQ ID NO:43) cloned into pg1d105 mammalian expression vector. Restriction sites are indicated by bold letters and underlined. CDRs 1 to 3 and the splice donor site are underlined. This is the DNA sequence of the eukaryotic expression vector pG1D105 containing the reshaped version A of F19 heavy chain variable region. This vector contains a cDNA version of the human gamma-1 constant region (allotype G1m (non-a,- z, -x) also known as Gm1(17) allotype).

The essential components of the construct are:

| | | |
|---|---|---|
| 1–2501 | = | pBR322 based sequence including Ampicillin resistance gene ColEI origin plus the SV40 origin and the crippled SV40 early promoter |
| 2502–3226 | = | dhfr gene |
| 3233–4073 | = | SV40 poly A sequence etc. |
| 4080–4302 | = | SPA site plus C2 termination signal |
| 4303–5867 | = | HCMVi promoter/enhancer |
| 5879–5885 | = | unique HindIII restriction site for cloning of immunoglobulin variable genes |
| 5886–5894 | = | Kozak sequence |
| 5895–5951 | = | signal peptide |
| 5952–6323 | = | reshaped F19 heavy chain version A |
| 6323–6330 | = | splice donor site |
| 6331–6336 | = | unique BamHI restriction site for cloning of immunoglobulin variable genes |
| 6337–7388 | = | cDNA copy of human gamma-1 constant regions preceded by a 62 bp intron |
| 7389–7709 | = | Arnie termination sequence |

The human gamma-1 constant region used in this construct has a G1m (non-a, -z, -x) also known as Gm1(17) allotype which is defined by a glutamic acid (E) residue at position 356 (according to Eu numbering), a methionine (M) residue at position 358 (according to Eu numbering) and a lysine (K) residue at position 214 (according to Eu numbering). These three residues are underlined in the sequence above.

FIGS. 34A and 34B. Heavy (panel A) (SEQ ID NOS:44, 45, 46, 47, 48, 49, 50, 51, 52) and light (panel B) (SEQ ID NOS: 53, 54, 55, 56, 57, 58, 59) chains RNA splicing events taking place during antibody F19 expression in mammalian cells—schematic overview.

A. Heavy chain RNA splicing

B. Kappa light chain RNA splicing

Figure 35:
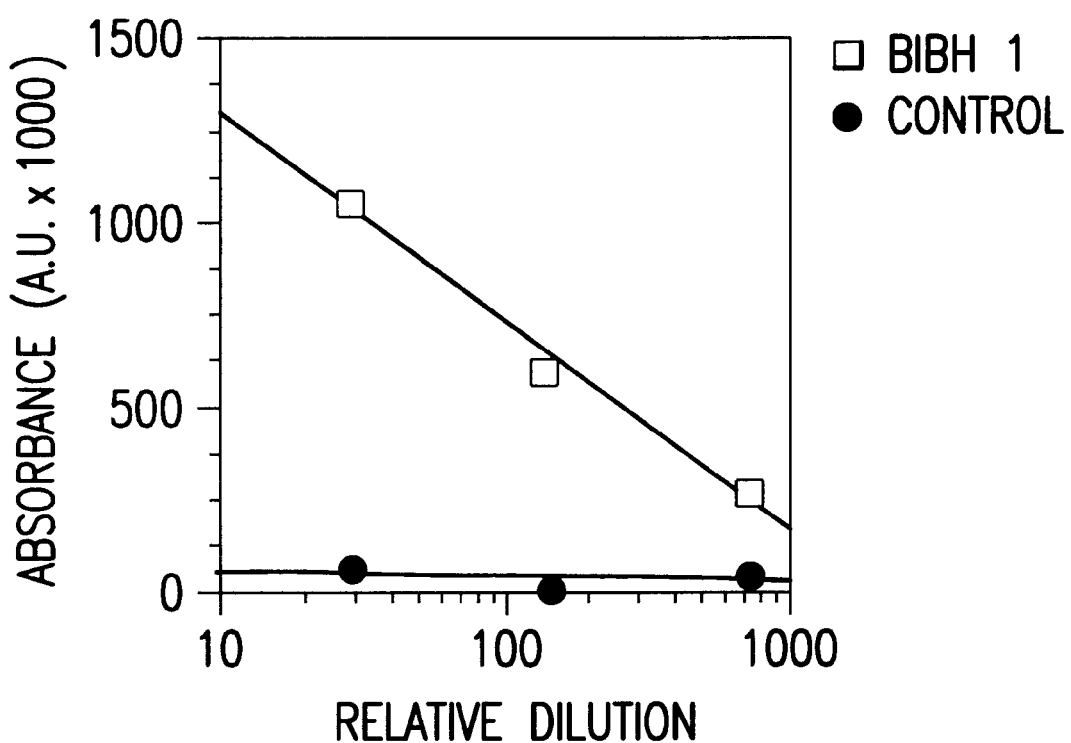

FIG. 35. Concentration dependence of $L_A H_C$ supernatant binding to CD8-FAP.

Figure 36:
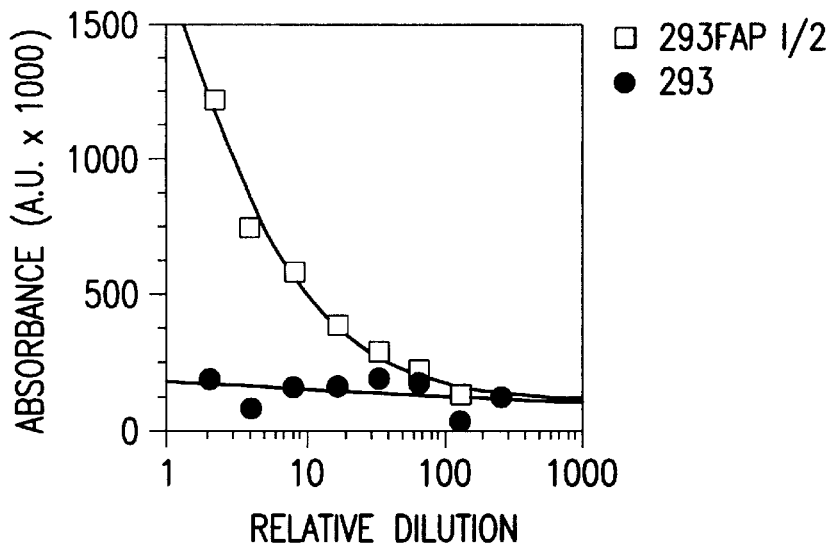

FIG. 36. Binding of biotinylated $L_A H_C$ to human FAP.

Figure 37:
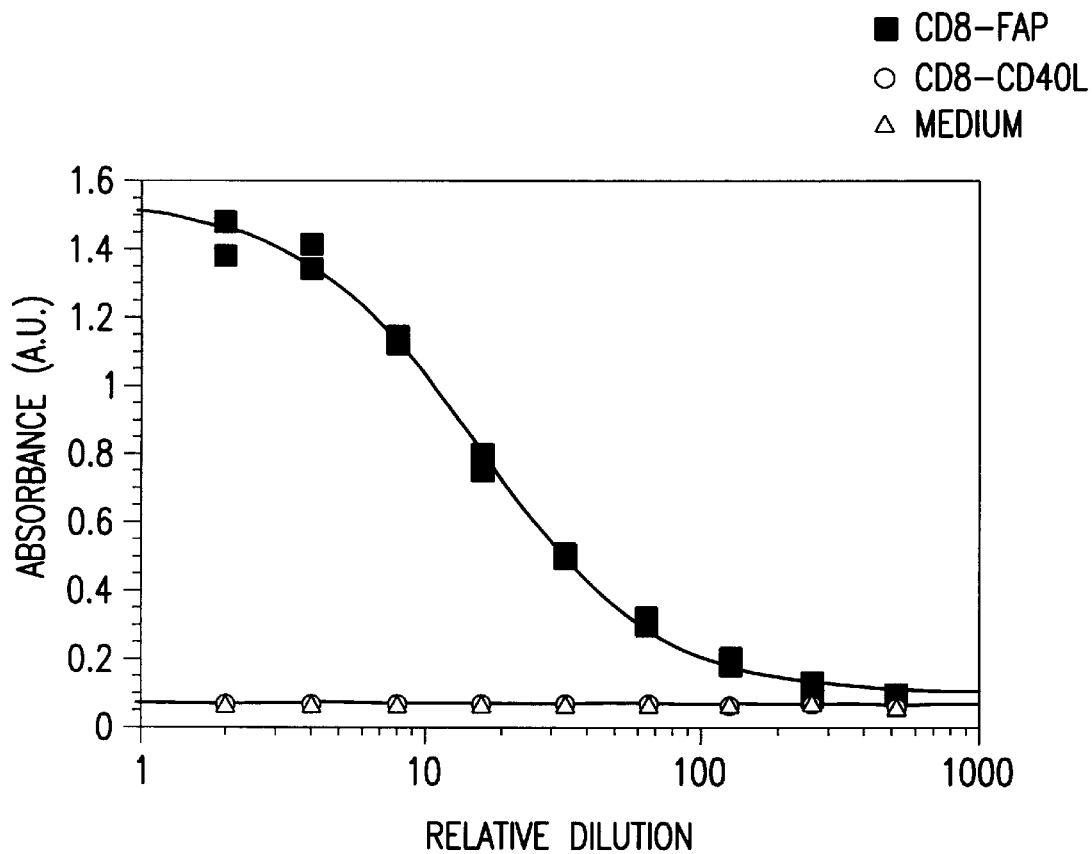

FIG. 37. CD8-FAP carries the F19 epitope as detected with cF19.

DETAILED DESCRIPTION OF THE PREFERRED EMBODIMENTS

EXAMPLES

Example 1

Construction of Mouse—Human Chimeric Genes

Figure 23B:
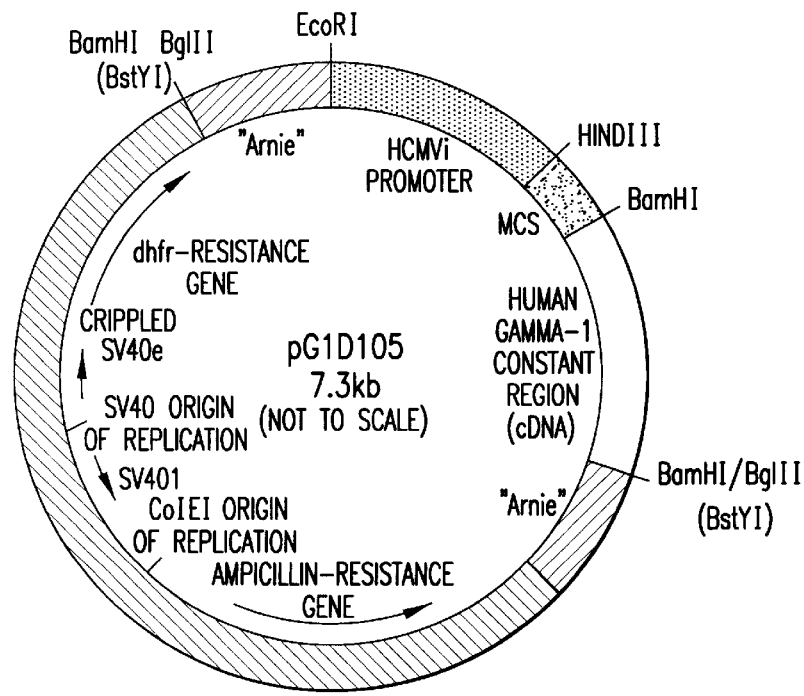

The chimeric F19 (cF19) antibody was designed to have the mouse F19 $V_L$ and $V_H$ regions linked to human kappa and gamma-1 constant regions, respectively. PCR primers were used to modify the 5'- and 3'-sequences flanking the cDNA sequences coding for the mouse F19 $V_L$ and $V_H$ regions (Table 1). PCR primers specific for F19 light chain V-region were designed. These adapted mouse F19 variable regions were then subcloned into mammalian cell expression vectors already containing the human kappa (pKN100 vector) or gamma-1 (pG1D105 vector) constant regions (FIGS. 23A and 23B). These vectors employ the human cytomegalovirus (HCMV) promoter/enhancer to efficiently transcribe the light and heavy chains. The vectors also contain the SV40 origin of replication to permit efficient DNA replication and subsequent protein expression in COS cells. The expression vectors were designed to have the variable regions inserted as HindIII-BamHI DNA fragments. PCR primers were designed to introduce these restrictions sites at the 5'-(HindIII) and 3'-(BamHI) ends of the cDNAs coding for the V-regions. In addition the PCR primers were designed to introduce the Kozak sequence (GCCGCCACC) (SEQ ID NO:62) at the 5'-ends of both the light and heavy chain cDNAs to allow efficient translation (Kozak, M., "At least six nucleotides preceding the AUG initiator codon enhance translation in mammalian cells," *J. Mol. Biol.* 196:947 (1987)), and to introduce splice donor sites at the 3'-ends of both the light and heavy chain cDNAs for the variable regions to be spliced to the constant regions. The PCR primers used in the construction of the chimeric F19 light and heavy chains are shown in Table 1. The DNA and amino acid sequences of the mouse F19 $V_L$ and $V_H$ regions as adapted for use in the construction of chimeric F19 light and heavy chains are shown in FIGS. 24, 25A and 25B. The DNA sequences of mouse F19 light and heavy chains cloned into the eukaryotic expression vectors pKN 100 and pG1D105, respectively, are shown in FIGS. 26A–26H and 27A–27G.

TABLE 1

PCR primers for the construction of chimeric F19 antibody

A. Light chain variable region
1. Primer for the construction of the 5'-end (37mer)
5'CAGA AAGCTT GCCGCCACC ATG GAT TCA CAG GCC CAG 3' (SEQ ID NO:63)
     HindIII Kozaksequence  M   D   S   Q   A   Q (SEQ ID NO:64)

2. Primer for the construction of the 3'-end (35mer)
5'CCGA GGATCC ACTCACG TTT CAG CTC CAG CTT GGT 3' (SEQ ID NO:65)
     BamHI Splicedonorsite B. Heavy chain variable region
1. Primer for the construction of the 5'-end (37mer)
5'CAGA AAGCTT GCCGCCACC ATG GGA TGG AGC TGG GTC 3' (SEQ ID NO:66)
     HindIII Kozaksequence M   G    W    S    W    V (SEQ ID NO:67)

2. Primer for the construction of the 3' (SEQ ID NO:68)-end (35mer)
5'CCGA GGATCC ACTCACC TGA GGA GAC GGT GAC TGA 3'
     BamHI Splicedonorsite

Example 2

Expression and Binding Activity of Chimeric F19 Antibody

The two plasmid DNAs coding for the chimeric F19 light and heavy chains (see example 1) were co-transfected into COS cells to look for transient expression of chimeric F19 antibody as described below. After incubation for 72 hours, the medium was collected, centrifuged to remove cellular debris, and analyzed by ELISA for the production of a human IgG1-like antibody. The COS cell supernatant containing the chimeric F19 antibody was analyzed for its ability to bind to HT 1080 cells (see example 13) expressing the FAP antigen on their surface.

Transfection of COS Cells Using Electroporation

The mammalian expression vectors pg1d105 and pKN100 containing the chimeric or reshaped human heavy and light chains versions, respectively, were tested in COS cells to look for transient expression of F19 antibodies. COS-7 cells were passaged routinely in DMEM (Gibco BRL cat. #41966) containing penicillin (50 IU/ml), streptomycin (50 mg/ml), L-glutamine and 10% heat-inactivated gamma globulin-free foetal calf serum (FCS, Harlan Sera-Lab cat. #D0001). The DNA was introduced into the COS cells by electroporation using the Gene Pulsar apparatus (BioRad). DNA (10 mg of each vector) was added to a 0.8 ml aliquot of $1\times10^7$ cells/ml in Phosphate-buffered saline (PBS, $Ca^{2+}$ and $Mg^{2+}$ free). A pulse was delivered at 1,900 volts, 25 mF capacitance. After a 10 minutes recovery period at ambient temperature the electroporated cells were added to 8 ml of DMEM containing 5% FCS. After incubation at 37° C. for 72 hours, the medium was collected, centrifuged to remove cellular debris, and stored under sterile conditions at 4° C. for short periods of time, or at −20° C. for longer periods.

ELISA Method for Measuring Assembled IgG1/Kappa Antibody Concentrations in COS Cell Supernatants Samples of antibodies produced in transfected COS cells were assayed by ELISA to determine how much chimeric or reshaped human antibody had been produced. For the detection of antibody, plates were coated with goat anti-human IgG (Fcg fragment specific) antibody (Jackson ImmunoResearch Laboratories Inc., #109-005-098). The samples from COS cells were serially diluted and added to each well. After incubation for 1 h at 37° C. and washing, horseradish peroxidase conjugated goat anti-human kappa light chain (Sigma, A-7164) was added. After incubation for 30 minutes at 37° C. and washing, K-blue substrate (a mixture of 3,3',5,5' tetramethylbenzidine and hydrogen peroxide, Bionostics Limited, #KB175) was added for 30 minutes at room temperature. The reaction was stopped using Red Stop solution (Bionostics Limited, #RS20) and the optical density read on a microplate reader at 650 nm. Purified human IgG1/Kappa antibody (Sigma, I-3889) of known concentration was used as a standard.

The expression of chimeric F19 antibody in COS cells was poor (Table 2), between 10 and 60 ng/ml, which is at least 10 fold less than most antibodies.

In an attempt to increase expression levels of the chimeric F19 antibody, the leader sequence of F19 $V_L$ region was changed by substitution of leucine to proline at position −9. This single change in amino acid in the leader sequence resulted in at least doubling the amount of chimeric antibody produced in COS cells.

Cell binding results show that chimeric F19 binds specifically and with the expected avidity to the FAP target.

TABLE 2

Chimeric F19 antibody concentrations in COS cell supernatants
(These are the results of three independent transfections)

| Transfected Antibody components | | Human γl/K |
|---|---|---|
| Heavy chain | Kappa light chain | [in µg/ml] |
| cF19 | cF19 (F19 leader sequence) | 0.060 |
| cF19 | cF19 (mutated leader sequence) | 0.212 |
| cF19 | cF19 (F19 leader sequence) | 0.056 |
| cF19 | cF19 (mutated leader sequence) | 0.108 |
| cF19 | cF19 (F19 leader sequence) | 0.011 |
| cF19 | cF19 (mutated leader sequence) | 0.087 |

Example 3

Construction of the Reshaped Human F19 Light Chain Versions A to C ($L_A$–$L_B$)

The construction of the first version of reshaped human F19 $V_L$ region ($L_A$) was carried out using overlapping PCR fragments in a method similar to that described by Daugherty B. L., et al., "Polymerase chain reaction (PCR) facilitates the cloning, CDR-grafting, and rapid expression of a murine monoclonal antibody directed against the CD18 component of leukocyte integrins," Nucl. Acids Res. 19:2471 (1991). Ten oligonucleotides were synthesized that consisted of five primer pairs, APCR1-vla1, vla2-vla3, vla4-vla5, vla6-vla7, and vla8-APCR4 (Table 3 and FIG. 28). There was an overlapping sequence of at least 21 bases between adjacent pairs (FIG. 28). APCR1 and APCR4 hybridized to the flanking pUC19 vector sequences. The mutagenic primers were designed such that their 5' end immediately followed the wobble position of a codon. This strategy was used to counteract the gratuitous addition of one nucleotide to the 3' end of the strand complementary to the mutagenic primer by the DNA polymerase during PCR (Sharrocks ,A. D., and Shaw, P. E., "Improved primer design for PCR-based, site-directed mutagenesis," Nucl. Acids Res. 20:1147 (1992)). The appropriate primer pairs (0.2 µM of each) were combined with 10 ng of version "B" of reshaped human L25VL region cDNA, and 1 unit of AmpliTaq (Perkin Elmer Cetus) DNA polymerase in 50 µl of PCR buffer containing 10 mM Tris-HCl (pH 8.3), 50 mM KCl, 200 µM dNTPs, and 1.5 mM $MgCl_2$. This was overlaid with mineral oil and PCR was performed for 25 cycles, each cycle consisting of a denaturation step at 94° C. for 1 minute, a primer annealing step at 55° C. for 1 minute, and an extension step at 72° C. for 2 minutes. This was followed by a single cycle consisting of a further elongation step at 72° C. for 10 minutes followed by cooling to 4° C. The ramp time between the primer-annealing and extension steps was 2.5 minutes. The PCR products of the five reactions (A, B, C, D and E) were then purified by gel electrophoresis followed by DNA elution using Wizard PCR preps (Promega). PCR products A, B, C, D, and E were assembled by their complementarity to one another. In the second set of PCR reactions, PCR products B and C, and D and E, (50 ng of each) were added to 50 ml PCR reactions (as described above) each containing 1 unit of AmpliTaq (Perkin Elmer Cetus) DNA polymerase. The reactions were cycled for 20 cycles as described above with the exception that the annealing temperature was raised to 60° C. In the third set of PCR reactions, PCR products F and G were PCR-amplified using 1 ml of each prior PCR reaction and the appropriate pair of PCR primers (vla2-vla5 or vla6-APCR4). The PCR reactions contained 1 unit of AmpliTaq DNA polymerase in 50 ml PCR reaction (as described above) and were amplified for 25 cycles as in the first stage. In the fourth set of PCR reactions, the PCR product H was PCR-amplified using 1 ml of each prior PCR reaction and the vla2-APCR4 pair of PCR primers. Finally, PCR products A and H were assembled by their own complementarity in a two step-PCR reaction similar to that described above using RSP and UP as the terminal primers. The fully assembled fragment representing the entire reshaped human F19 $V_L$ region including a leader sequence was digested with HindIII and BamHI and cloned into pUC19 for sequencing. A clone having the correct DNA sequence was designated reshF19La (FIGS. 29A and 29B) and was then subcloned into the eukaryotic expression vector pKN100. The DNA sequence of reshF19La cloned into pKN100 is shown in FIGS. 30A–30G.

The second version of reshaped human F19 $V_L$ region ($L_B$) was constructed using the same scheme as that described for La but where vla4 and vla7 primers were substituted by vlb4 and vlb7 respectively (Table 3). The DNA sequence of $L_B$ is shown in FIGS. 29A and 29B.

The third version of reshaped human F19 $V_L$ region ($L_C$) was constructed using the QuikChange™ site-directed mutagenesis kit from Stratagene. The QuikChange site-directed mutagenesis method was performed according to the manufacturer's instructions, using reshF19La in pKN100 vector as double stranded DNA template. The mutagenic oligonucleotide primers F19Lc-sense and F19Lc-antisense (Table 3) for use in this protocol were designed according to the manufacturer's instructions. Briefly, both the mutagenic primers contained the desired point mutation (codon TTT at Kabat residue position 49 (Phe) changed to TAT coding for Tyr) and annealed to the same sequence on opposite strands of LA in pKN100 vector. The point mutation was verified by DNA sequencing the entire $V_L$ region. The DNA sequence of $L_C$ is shown in FIGS. 29A and 29B. To eliminate the possibility that random mutations occurred in the pKN100 during the PCR reaction, the $V_L$ region was cut out of the pKN100 vector as an HindIII/BamHI fragment and re-subcloned into an unmodified pKN100 vector cut with the same two restriction enzymes beforehand.

TABLE 3

PCR primers for the construction of reshaped human F19 light chain variable regions 1. Primers for the synthesis of version "A"
F19vla1(36 mer):
5' GTCATCACAATGTCTCCGGAGGAACCTGGAACCCAG 3' (SEQ ID NO:69)

F19vla2 (29 mer):
5' CTCCGGAGACATTGTGATGACCCAATCTC 3' (SEQ ID NO:70)

F19vla3 (45 mer):
5' GAATATAAAAGGCTCTGACTGGACTTGCAGTTGATGGTGGCCCTC 3' (SEQ ID NO:71)

F19vla4 (72 mer):
5' CAGTCAGAGCCTTTTATATTCTAGAAATCAAAAGAACTACTTGGCCTG
    GTATCAGCAGAAACCAGGACAGCC 3' (SEQ ID NO:72)

F19vla5 (44 mer):
5' ACCCCAGATTCCCTAGTGCTAGCCCAAAAGATGAGGAGTTTGGG 3' (SEQ ID NO:73)

F19vla6 (67 mer):
5' TAGCACTAGGGAATCTGGGGJACCTGATAGGTTCAGTGGCAGTGGGTT
    TGGGACAGACTTCACCCTC 3' (SEQ ID NO:74)

F19vla7 (53 mer):
5' GTCCCTTGTCCGAACGTGAGCGGATAGCTAAAATATTGCTGACAGTAA
    TAAAC3' (SEQ ID NO:75)

F19vla8 (33 mer):
5' GCTCACGTTCGGACAAGGGACCAAGGTGGAAAT 3' (SEQ ID NO:76)

2. Primers for the synthesis of version "B"
F19vlb4 (72 mer):
5' CAGTCAGAGCCTTTTATATTCTAGAAATCAAAAGAACTACTTGGCCTG
    GTTCCAGCAGAAACCAGGACAGCC 3' (SEQ ID NO:77)

F19vlb7 (56 mer):
5' TCCCTTGTCCGAACGTGAGCGGATAGCTAAAATATTGCTGACAGTCAT
    AAACTGCC 3' (SEQ ID NO:78)

3. Primers for the synthesis of version "C"
F19Lc-sense (34 mer):
5' CCCAAACTCCTCATCTATTGGGCTAGCACTAGGG 3' (SEQ ID NO:79)

F19Lc-antisense (34 mer):
5' CCCTAGTGCTAGCCCAATAGATGAGGAGTTTGGG 3' (SEQ ID NO:80)

TABLE 3-continued

PCR primers for the construction of reshaped human F19 light chain variable regions 4. Primers hybridizing to the flanking PUC19 vector sequences
    APCR1 (17 mer, sense primer): 5' TACGCAAACCGCCTCTC 3' (SEQ ID NO:81)
  APCR4 (18 mer, anti-sense primer): 5' GAGTGCACCATATGCGGT 3' (SEQ ID NO:82)
   RSP (-24) (16 mer, sense primer): 5' AACAGCTATGACCATG 3' (SEQ ID NO:83)
  UP (-40) (17 mer, anti-sense primer): 5' GTTTTCCCAGTCACGAC 3' (SEQ ID NO:84)

Example 4

Construction of the Reshaped Human F19 Heavy Chain Versions A to E ($H_A$–$H_E$)

Version "A" of reshaped human F19 $V_H$ regions ($H_A$) was constructed using the same PCR methods as described for the construction of version "A" of reshaped human F19 $V_L$ region ($L_A$) (FIG. 31). The template DNA was version "A" of reshaped human 226 $V_H$ (Léger, O. J. P., et al., "Humanization of a mouse antibody against human alpha-4 integrin: a potential therapeutic for the treatment of multiple sclerosis," Hum. Antibod. 8:3 (1997)). Six PCR primers were designed and synthesized for the construction of version "A" of reshaped human F19 $V_H$ region (Table 4). PCR products A, B, C, and D were obtained using APCR1-Vha1, Vha2-Vha3, Vha4-Vha5 and Vha6-APCR4 as PCR primer pairs, respectively. The PCR conditions were essentially as described for the construction of reshaped human F19 $V_L$ region. A clone having the correct DNA sequence was designated reshF19Ha (FIGS. 32A–32D) and was then subcloned into the eukaryotic expression vector pG1D105. The DNA sequence of reshF19Ha cloned into pG1D105 is shown in FIGS. 33A–33F.

The third version of reshaped human F19 $V_H$ region ($H_C$) was constructed using the same scheme as that described for $H_A$ but where Vha4 primer was substituted by Vhc4 (Table 4). The DNA sequence of $H_C$ is shown in FIGS. 32A–32D. The second ($H_B$) and fourth ($H_D$) version of reshaped human F19 $V_H$ region were constructed based on the PCR-mutagenesis methods of Kamman et al. (Kamman, M., et al., "Rapid insertional mutagenesis of DNA by polymerase chain reaction (PCR)," Nucl. Acids Res. 17:5404 (1989)). For $H_B$ and $H_D$, a mutagenic primer F19VHbd6 (Tyr-91 to Phe-91, Table 4) was used paired with APCR4 in PCR reactions with $H_A$ and $H_C$ as the template DNA, respectively. The PCR products VHb and VHd were restriction enzyme digested with PstI and BamHI and subcloned into reshF19Ha and reshF19Hc, respectively, previously digested with the same two restriction enzymes. The DNA sequences of $H_B$ and $H_D$ are shown in FIGS. 32A–32D.

Version "E" of reshaped human F19 $V_H$ region ($H_E$) was constructed based on the PCR-mutagenesis methods of Kamman et al. (1989) already mentioned above:

For reshF19He mutagenic primer F19MscIHe (Table 5) was used paired with primer F19$_H$HindIII (Table 5) in PCR reactions with $H_C$ cloned in pg1d105 mammalian expression vector as the template DNA. The appropriate primer pairs (0.2 mM of each) were combined with 10 ng of cDNA of version "A" of reshaped human 226 $V_H$ region in 100 ml of PCR buffer containing 10 mM KCl, 10 mM (NH$_4$)2SO$_4$, 20 mM Tris-HCl (pH 8.8) 2 mM MgSO$_4$, 0.1% Triton X-100 and 200 mM dNTPs. Reaction mixtures were overlaid with mineral oil and kept at 94° C. for 5 minutes. Then 1 unit of Deep Vent DNA polymerase (New England Biolabs) was added ("Hot Start" PCR; Chou Q., Russell, M., et al., "Prevention of pre-PCR mis-priming and primer dimerization improves low-copy-number amplifications," Nucl. Acids Res. 20:1717 (1992)) and PCR was performed for 25 cycles on a TRIO-Thermoblock Thermal Cycler (Biometra, Göittingen, Germany). Each cycle consisting of a denaturation step at 94° C. for 1 minute, a primer-annealing step at 70 ° C. for 1 minute, and an extension step at 72 ° C. for 2 minutes. This was followed by a single cycle consisting of a further elongation step at 72° C. for 10 minutes followed by cooling at 4° C. The PCR products were then extracted and purified from a TAE 1.4% standard agarose gel using a QIAquick™ gel extraction kit, following the protocol supplied by the manufacturer (QIAGEN Ltd., UK). The PCR product $V_H$e was then restriction enzyme digested with MscI and HindIII and ligated into reshF19Hc cloned in pg1d105 previously digested with the same two restriction enzymes. The MscI restriction recognition site is unique to all the reshaped human F19 $V_H$ region versions and is not present in the pg1d105 expression vector. The HindIII restriction recognition site is a unique site in pg1d105 for cloning of $V_H$ immunoglobulin genes. Electroporation-competent XL-1 Blue E. coli cells were transformed with 1 µl of the ligated DNA and plated on agarose plates containing Ampicillin. Colonies were then screened for the presence and correct size of inserts by direct PCR on colonies (Güssow, D., and Clackson, T., "Direct clone characterization from plaques and colonies by the polymerase chain reaction," Nucl. Acids Res. 17:4000 (1989)) with primers HCMi and Hucg1 hybridizing to the flanking pg1d105 vector sequences (Table 5). DNA from positive colonies was prepared using a Plasmid Midi kit, following the protocol supplied by the manufacturer (QIAGEN Ltd., UK). DNA sequencing was performed by the dideoxy chain termination method (Sanger, F., et al., "DNA sequencing with chain-terminating inhibitors," Proc.

Natl. Acad. Sci. U.S.A. 74:5463 (1977)) directly from circular vector DNA using conventional heat denaturation (Andersen, A., et al., "A fast and simple technique for sequencing plasmid DNA with sequenase using heat denaturation," Biotechniques 13:678 (1992)) and Sequenase 2.0 (USB, Cleveland, Ohio). The DNA sequences of reshF19He is shown in FIGS. 32A–32D.

TABLE 4

PCR primers for the construction of reshaped human F19 heavy chain variable regions versions A to D 1. Primers for the synthesis of version "A"
F19vha1 (47 mer):
5' GTGTATTCAGTGAAGGTGTATCTACTAGTTTTACAGCTGACTTTCACA 3' (SEQ ID NO:85)

F19vha2 (53 mer):
5' TAGTAGATACACACCTTCACTGAATACACCATACACTGGGTTAGACAGGC
   CCTG 3' (SEQ ID NO:86)

F19vha3 (71 mer):
5' CCCTTGAACTTCTGGTTGTAGTTAGGAATACCATTGTTAGGATTAATA
   CCTCCTATCCACTCCAGCCTTTG 3' (SEQ ID NO:87)

F19vha4 (71 mer):
5' TAACTACAACCAGAAGTTCAAGGGCCGGGGCCACCTTGACCGTAGGCAA
   GTCTGCCAGCACCGCCTACATGG 3' (SEQ ID NO:88)

F19vha5 (63 mer):
5' GCATGGCCCTCGTCGTAACCATAGGCGATTCTTCTTCTGGCGCAGTAG
   TAGACTGCAGTGTCC 3' (SEQ ID NO:89)

F19vha6 (48 mer):
5' CTATGGTTACGACGAGGGCCATGCTATGGACTACTGGGGTCAAGGAAC
   3' (SEQ ID NO:90)

2. Primers for the synthesis of version "C"
F19vhc4 (71 mer):
5' TAACTACAACCAGAAGTTCAAGGGCCGGGTCACCATCACCGTAGACAC
   CTCTGCCAGCACCGCCTACATGG 3' (SEQ ID NO:91)

3. Primers for the synthesis of version "B" and "D"
F19vhbd6 (27 mer):
5' GGACACTGCAGTCTACTTCTGCGCCAG 3' (SEQ ID NO:92)

4. Primers hybridizing to the flanking PUC19 vector sequences
APCR (17 mer, sense primer):
5' TACGCAAACCGCCTCTC 3' (SEQ ID NO:93)

APCR4 (18 mer, anti-sense primer):
5' GAGTGCACCATATGCGGT 3' (SEQ ID NO 94)

TABLE 5

PCR primer for the construction of reshaped human F19 heavy chain variabie regions version E 1. Primer for the synthesis of version "E"
F19MscIHe (75 mer, anti-sense):
5' CCTTT*TGGCCA*GGGGCCTGTCTAACCCAGTGTAT(3GTGTATTCAGTGAAGGTG
        MscI
   TATCCACTAGTTTCCACTAGTTT 3'(SEQ ID NO:95)

2. Primers hybridizing to the flanking pgld105 mammalian expression vector sequences
HCMi (28 mer, sense):
5' GTCACCGTCCTTGACACGCGTCTCGGGA 3'(SEQ ID NO:96)

Hucg1 (17 mer, anti-sense):
5' TTGGAGGAGGGTGCCAG 3'(SEQ ID NO:97)

Example 5

Reshaped Human F19 Antibody Concentrations in COS Cell Supernatants

COS cells were transfected with one pair of a series of reshaped human F19 antibody constructs and the human antibody concentration was measured using the IgG1/Kappa ELISA as described in example 2.

TABLE 6

Reshaped human F19 antibody concentrations in COS cell supernatants

| Transfected Antibody components | | Human γl/K |
|---|---|---|
| Heavy chain | Kappa light chain | Concentration [μg/ml] |
| $H_A$ | $L_A$ | 2.50 |
| $H_A$ | $L_B$ | 0.18 |

TABLE 6-continued

Reshaped human F19 antibody concentrations in COS cell supernatants

| Transfected Antibody components | | Human γl/K |
|---|---|---|
| Heavy chain | Kappa light chain | Concentration [μg/ml] |
| $H_B$ | $L_A$ | 1.25 |
| $H_B$ | $L_B$ | 0.10 |
| $H_D$ | $L_A$ | 1.15 |
| $H_D$ | $L_B$ | 0.18 |
| $H_A$ | $L_A$ | 1.50 |
| $H_A$ | $L_C$ | 1.56 |
| $H_C$ | $L_A$ | 1.47 |
| $H_C$ | $L_C$ | 1.97 |
| cF19 | $L_A$ | 1.54 |
| cF19 | $L_B$ | 0.07 |
| cF19 | $L_C$ | 2.14 |

TABLE 7

Reshaped human F19 antibody concentrations in COS cell supernatants

| Transfected Antibody components | | Human γl/K |
|---|---|---|
| Heavy chain | Kappa light chain | concentration [μg/ml] |
| $H_A$ | $L_A$ | 2.00 |
| $H_A$ | $L_C$ | 2.50 |
| $H_C$ | $L_A$ | 2.90 |
| $H_C$ | $L_C$ | 3.00 |
| $H_E$ | $L_A$ | 2.80 |
| $H_E$ | $L_C$ | 3.50 |

RNA Splicing Events Required for the Expression of Immunoglobulin Genes in Mammalian Cells Both mammalian expression vectors pKN100 and pg1d105 have an intron between the variable and the constant regions which is removed during the process of gene expression to give rise to an messenger RNA. The splicing event which consists of a DNA recombination between the heavy or light chain splice donor sites and the immunoglobulin splice acceptor site is described in FIGS. 34A and 34B.

Example 6

Flow Cytometric Analysis of the Binding of cF19 and $L_A H_C$ to FAP-expressing Human Cells The ability of $L_A H_C$ to bind to both recombinant and endogenously expressed FAP on cell surface was tested.

The example was conducted to determine the binding of $L_A H_C$ to cellular FAP. Both naturally FAP expressing MF-SH human tumor cells (Shirasuma, K., et al., *Cancer* 55:2521–2532 (1985)) and FAP-transfected human tumor cell lines were used as cellular targets. $L_A H_C$ was studied in cytofluorometric assays evaluating direct binding to target cells as well as by the inhibitory effect on the binding of either murine F19 or chimeric cF19 anti-FAP antibodies.

Antibodies and cell lines used were F19 (murine monoclonal anti-human FAP antibody, IgG1 subclass), mIgG (murine immunoglobulin, IgG class), cF19 (chimeric monoclonal anti-human FAP antibody, IgG1 subclass), $L_A H_C$ (reshaped monoclonal anti-human FAP antibody, IgG1 subclass), hIgG1 (human immunoglobulin, IgG1 subclass), MF-SH (human malignant fibrous histiocytoma cell line), HT-1080 (human fibrosarcoma cell line), HT-1080FAP clone 33 (HT-1080 cell line transfected with cDNA encoding human FAP). Antibodies were biotinylated as described in examples 8 and 12.

Direct Binding of $L_A H_C$ to FAP on the Surface of Human Tumor Cell Lines $5 \times 10^5$ cells of the tumor cell line under investigation were incubated with the indicated concentration of test or control antibody in a total volume of 0.2 ml phosphate-buffered saline (PBS) supplemented with 1% bovine serum albumin (BSA) for 30 minutes on ice. Subsequently, cells were washed twice with 2 ml of PBS, resuspended in 0.2 ml of PBS supplemented with 1% BSA, a 1:20 dilution of mouse anti-human IgG FITC-labelled (Dianova) as secondary reagent was added and incubated for another 30 minutes on ice.

Alternatively, $5 \times 10^5$ cells of the tumor cell line under investigation were incubated with the indicated concentration of biotin-labelled cF19 in a total volume of 0.2 ml PBS supplemented with 1% BSA for 30 minutes on ice. Subsequently, cells were washed twice with 2 ml of PBS, resuspended in 0.2 ml of PBS supplemented with 1% BSA, and incubated for another 30 minutes on ice with 1:40 dilution of streptavidin-FITC (Dianova) as secondary reagent.

Cells were again washed twice with 2 ml of PBS, resuspended in a total volume of 0.5 ml of PBS supplemented with 1% paraformaldehyde (PFA) and kept on ice. Single cell fluorescence was determined cytofluorometrically by analysing the cellular green fluorescence at 488 nm in an EPICS XL (Coulter) fluorescence-activated cell analyzer. cl Competition of $L_A H_C$ for Binding of Biotinylated cF19 to Cell-surface FAP on FAP-expressing Human Cell Lines $5 \times 10^5$ cells of the tumor cell line under investigation were incubated with the indicated amounts of unlabeled test or control antibody added together with 1 μg/ml biotin-labelled cF19 antibody. Subsequently, cells were washed twice with 2 ml of PBS, resuspended in 0.2 ml of PBS supplemented with 1% BSA, 1:40 diluted streptavidin-FITC (Dianova) as secondary reagent and incubated for another 30 minutes on ice.

Cells were then washed twice with 2 ml of PBS, resuspended in a total volume of 0.5 ml PBS supplemented with 1% PFA and kept on ice. Single cell fluorescence was determined cytofluorometrically by analysing the cellular green fluorescence at 488 nm in an EPICS XL (Coulter) fluorescence-activated cell analyzer.

Both, cF19 and $L_A H_C$ bind in a concentration dependent manner specifically to to FAP-transfected HT-1080FAP clone33 human tumor cells (Table 8). No binding to FAP-negative HT-1080 cells was detectable (Table 9). Both cF19 and $L_A H_C$ bound in a concentration dependent manner to human MF-SH cells endogenously expressing FAP (Table 10).

Biotinylated cF19 bound to human HT-1080FAP clone 33 (Table 11) in a concentration dependent manner. No binding was detectable to FAP-negative HT-1080 cells (Table 12).

Binding of biotinylated cF19 to HT-1080FAP clone 33 cells was inhibited by both unlabelled cF19 and unlabelled $L_A H_C$ (Table 13).

Chimeric anti-human FAP monoclonal antibody cF19 as well as reshaped human anti-human FAP monoclonal antibody $L_A H_C$ (example 10) were shown to bind directly to FAP expressed on human cell lines either endogenously expressing this protein or transfected with cDNA encoding for it. This binding was shown to be concentration dependent. Binding of biotinylated cF19 could be inhibited by both unlabelled cF19 and unlabelled $L_A H_C$.

Using cytofluorometric technology, direct binding as well as inhibition of specifically binding reagents showed specificity of chimeric cF19 and reshaped $L_A H_C$ human monoclonal antibodies to cell surface expressed FAP.

TABLE 8

Binding of anti-FAP antibodies to HT-1080FAP clone 33 cells

| Concentration of antibody | Mean fluorescence intensity | | |
|---|---|---|---|
| [ng/ml] | hIgG1 | cF19 | $L_A H_C$ |
| 500 | 0.12 | 6.65 | 2.76 |
| 100 | 0.12 | 1.63 | 0.66 |
| 20 | 0.12 | 0.43 | 0.22 |
| 4.0 | 0.12 | 0.17 | 0.15 |
| 0.8 | 0.12 | 0.14 | 0.13 |

TABLE 9

Binding of anti-FAP antibodies to non-transfected HT-1080 cells

| Concentration of antibody | Mean fluorescence intensity | | |
|---|---|---|---|
| [ng/ml] | hIgG1 | cF19 | $L_A H_C$ |
| 500 | 0.11 | 0.11 | 0.12 |
| 100.0 | 0.11 | 0.11 | 0.11 |
| 20.0 | 0.11 | 0.11 | 0.12 |
| 4.0 | 0.11 | 0.11 | 0.12 |
| 0.8 | 0.11 | 0.11 | 0.11 |

TABLE 10

Binding of anti-FAP antibodies to MF-SH cells

| Concentration of antibody | Mean fluorescence intensity | | |
|---|---|---|---|
| [ng/ml] | hIgG1 | cF19 | $L_A H_C$ |
| 4,000 | 0.6 | 3.6 | 2.8 |
| 2,000 | n.d. | 3.3 | 2.5 |
| 1,000 | n.d. | 2.4 | 1.9 |
| 500 | n.d. | 1.8 | 1.3 | n.d.: not done

TABLE 11

Binding of biotinylated cF19 antibody to HT-1080FAP clone 33 cells

| Concentration of antibody | Mean fluorescence intensity | |
|---|---|---|
| [ng/ml] | Biotinylated hIgG1 | Biotinylated cF19 |
| 5,000.0 | 0.2 | 36.5 |
| 1,000.0 | 0.2 | 18.1 |
| 200.0 | 0.2 | 4.5 |
| 40.0 | 0.2 | 1.3 |
| 8.0 | 0.2 | 0.5 |
| 1.6 | 0.3 | 0.3 |

TABLE 12

Binding of biotinylated cF19 antibody to non-transfected HT-1080 cells

| Concentration of antibody | Mean fluorescence intensity | |
|---|---|---|
| [ng/ml] | Biotinylated hIgG1 | Biotinylated cF19 |
| 5,000.0 | 0.1 | 0.1 |
| 1,000.0 | 0.1 | 0.1 |
| 200.0 | 0.1 | 0.1 |
| 40.0 | 0.1 | 0.1 |
| 8.0 | 0.1 | 0.1 |
| 1.6 | 0.1 | 0.1 |

TABLE 13

Competition of anti-FAP antibodies with the binding of biotinylated cF19 to HT-1080FAP clone 33 cells

| Competitor antibody | Concentration of competitor antibody [µg/ml] | Mean fluorescence concentration |
|---|---|---|
| No | 0.00 | 11.2 |
| hIgG1 | 1.00 | 9.0 |
| hIgG1 | 3.16 | 11.3 |
| hIgG1 | 10.00 | 9.8 |
| hIgG1 | 31.66 | 10.3 |
| cF19 | 1.00 | 7.5 |
| cF19 | 3.16 | 4.8 |
| cF19 | 10.00 | 1.3 |
| cF19 | 31.66 | 1.2 |
| $L_A H_C$ | 1.00 | 8.0 |
| $L_A H_C$ | 3.16 | 5.5 |
| $L_A H_C$ | 10.00 | 2.9 |
| $L_A H_C$ | 31.66 | 1.7 |

Biotinylated cF19 was used at a concentration of 1 µg/ml in all tests shown in Table 13.

Example 7

In Vitro Immune Effector Functions of Monoclonal Antibody $L_A H_C$

This experiment was conducted to determine the potential of the monoclonal antibody (mAb) $L_A H_C$ with specificity for fibroblast activation antigen (FAP) to lyse FAP-expressing targets in the presence of human complement or human mononuclear leukocytes, respectively.

In particular, the ability of $L_A H_C$ to mediate cytotoxic effects against HT-1080FAP clone 33 cells, which expressed human FAP on the surface, was studied. Cytotoxicity was determined in vitro using the following approach: $^{51}$Cr-labelled target cells were incubated in the presence of $L_A H_C$ with human serum as source of complement or human MNC (peripheral blood mononuclear cells) as effectors. Release of $^{51}$Cr was measured as measure of target-cell lysis.

Antibodies and cell lines used were $L_A H_C$ (reshaped human anti-human FAP IgG1 antibody), hIgG1 (human IgG1 isotype control), 3S193 (murine monoclonal anti-Lewis$^y$ IgG3 antibody), mIgG (murine IgG control), HT-1080 (human fibrosarcoma), HT-1080FAP clone 33, (HT1080 transfected with cDNA encoding human FAP), MCF-7 (human breast adenocarcinoma cell line).

Complement-mediated Lysis of Target Cells by $L_A H_C$

Tumor cells were radiolabelled by incubation in RPMI1640 medium with 100 µl-Ci $^{51}$Cr (NEN) at 37° C. for one hour. Subsequently, cells were washed twice in $^{51}$Cr-free medium and resuspended at a concentration of 2×10$^5$ cells per ml.

Human serum as source of complement was freshly prepared from blood of different volunteers. Blood was taken by puncturing the arm vein, remained at room temperature for one hour to allow clotting to occur, and was kept at 4° C. over night. Serum was separated by centrifugation and taken off from the sediment.

The antibody under study was diluted from the stock solution to the appropriate concentration in RPMI1640 cell culture medium.

1×10$^5$ radiolabelled tumor cells of the indicated cell line were incubated for 2 h at 37° C. in an incubator (95% air and 5% CO$_2$) in the presence of different concentrations of test or control antibody and 25% (v/v) human serum as the source of human complement. Incubations were performed in U-shaped 96-well plates in a total volume of 200 µl RPMI1640 and done in triplicate. After the incubation period, plates were centrifuged, 100 µl of the supernatant was removed and radioactivity was counted in a gamma-counter. The total amount of incorporated radioactivity was determined by measuring 10$^4$ target cells. Spontaneous release was defined as activity released from the target cells in the absence of both antibody and complement during the described incubation period.

Specific lysis was calculated as follows:

$$\text{Specific lysis (in \%)} = \frac{[\text{activity sample}] - [\text{activity spontaneous release}]}{[\text{maximum activity}] - [\text{activity spontaneous release}]} \times 100$$

Antibody-dependent Cellular Cytotoxicity (ADCC) of $L_A H_C$

Tumor cells were radiolabelled by incubation in RPMI1640 medium with 100 µl-Ci $^{51}$Cr at 37° C. for one hour. Subsequently, cells were washed twice in $^{51}$Cr-free medium and resuspended at a concentration of 2×10$^5$ cells per ml.

MNC (peripheral blood mononuclear cells) were prepared from peripheral blood taken by puncturing the arm vein of different healthy human volunteers. Clotting was prevented by the addition of 20% citrate buffer. MNC from 4 ml of this blood preparation were purified by centrifugation (30 minutes at 400 G and room temperature) on 3 ml of lymphocyte preparation medium (Boehringer Mannheim, Germany). MNC (peripheral blood mononuclear cells) were taken off from the gradient, washed three times and diluted with RPMI1640 to the appropriate concentration. Lymphocyte activated killer (LAK) cells were derived from MNC (peripheral blood mononuclear cells) by incubation for 5 days at 37° C. in an 95% air and 5% CO$_2$ incubator at an initial density of 1.3×10$^6$ cells per ml in the presence of 100 U recombinant human Interleukin-2 (IL-2). The antibody under study was diluted from the stock solution to the appropriate concentration in RPMI1640 cell culture medium.

1×10$^4$ radiolabelled tumor cells of the indicated cell line were incubated for 5 h at 37° C. and 5% CO$_2$ in the presence of different concentrations of test or control antibody and MNC. MNC were added in amounts to reach the indicated effector:target cell ratio. Incubation was performed in U-shaped 96-well plates in a total volume of 200 µL RPM 1640 and done in duplicate.

After the incubation period, plates were centrifuged, 100 µl of the supernatant were taken off and radioactivity was determined in a gamma-counter. The total amount of incorporated radioactivity was determined by measuring 10$^4$ target cells. Spontaneous release was defined as activity released from the target cells in the absence of both antibody and effector cells during the described incubation period.

Specific lysis was calculated as follows:

$$\text{Specific lysis (in \%)} = \frac{[\text{activity sample}] - [\text{activity spontaneous release}]}{[\text{maximum activity}] - [\text{activity spontaneous release}]} \times 100$$

Antibody-mediated Complement Lysis of Tumor Cells

No $L_A H_C$-specific complement-mediated lysis (above that seen with an isotype control) was observed in HT-1080FAP clone 33 cells treated with $L_A H_C$ at concentrations up to 50 µg/ml (Table 14, Table 15a).

Lytic activity of human serum used as source of complement was shown by lysis of MCF-7 human breast carcinoma cells in the presence of 12.5 µg/ml 3S193, a murine monoclonal anti-Lewis$^y$ antibody with known complement activating ability (Table 15b).

Antibody-mediated Cellular Lysis of Tumor Cells

In the presence of $L_A H_C$ at concentrations up to 10 µg/ml, no ADCC (antibody-dependent cellular toxicity) mediated by human MNC (Table 16) or human LAK cells (lymphokine activated killer cells, Table 17) of $L_A H_C$ on HT-1080FAP clone 33 as measured by lysis was detectable above that seen with an isotype control at an effector:target ratio of 50:1.

In appropriate in vitro assays with either human complement or with human MNC as effector mechanisms, human anti-FAP monoclonal antibody $L_A H_C$ revealed no detectable cytotoxic effects above isotype controls on FAP-expressing tumor cell line HT-1080FAP clone 33.

TABLE 14

| Specific complement lysis (in %) of HT-1080FAP clone 33 tumor cell targets mediated by $L_A H_C$ | | |
|---|---|---|
| Source of human serum: | HT-1080 clone 33: | |
| Concentration of antibody | hIgG1 isotype control | $L_A H_C$ |
| A 50 µg/ml | 5 | 4 |
| A 10 µg/ml | 5 | 3 |
| B 50 µg/ml | 7 | 5 |
| B 10 µg/ml | 6 | 5 |
| 0 µg/ml | 0 | 0 |

Incubation: 2 hours at 37° C., 25% serum from human volunteers A or B, respectively, as source of complement.

Incubation: 2 hours at 37° C., 25% serum from human volunteers A or B, respectively, as source of complement.

TABLE 15a

Specific complement lysis (in %) of HT-1080FAP clone 33 tumor cell targets mediated by human anti-FAP monoclonal antibody $L_AH_C$

| Source of human serum: | HT-1080 clone 33: | |
|---|---|---|
| Concentration of antibody | hIgG1 | $L_AH_C$ |
| A 10.00 µg/ml | 2 | 1 |
| A 2.50 µg/ml | 2 | 2 |
| A 0.60 µg/ml | 1 | 1 |
| A 0.15 µg/ml | 1 | 2 |
| A 0.00 µg/ml | 2 | 2 |
| B 10.00 µg/ml | 2 | 2 |
| B 2.50 µg/ml | 2 | 2 |
| B 0.60 µg/ml | 2 | 2 |
| B 0.15 µg/ml | 2 | 2 |
| B 0.00 µg/ml | 2 | 2 |
| C 10.00 µg/ml | 2 | 2 |
| C 2.50 µg/ml | 1 | 1 |
| C 0.60 µg/ml | 1 | 1 |
| C 0.15 µg/ml | 2 | 1 |
| C 0.00 µg/ml | 3 | 3 |

Incubation: 2 hours at 37° C., 25% serum from human volunteers A, B or C, respectively, as source of complement.

TABLE 15b

Specific complement lysis (in %) of MCF-7 tumor cell targets mediated by murine anti-Lewis$^y$ monoclonal antibody 3S193

| Source of human serum: | MCF-7: | |
|---|---|---|
| Concentration of antibody | mIgG | 3S193 |
| A 10.00 µg/ml | 0 | 21 |
| A 2.50 µg/ml | 1 | 21 |
| A 0.60 µg/ml | 0 | 21 |
| A 0.15 µg/ml | 1 | 18 |
| A 0.00 µg/ml | 0 | 0 |
| B 10.00 µg/ml | 1 | 13 |
| B 2.50 µg/ml | 0 | 17 |
| B 0.60 µg/ml | 1 | 18 |
| B 0.15 µg/ml | 1 | 15 |
| B 0.00 µg/ml | 0 | 0 |
| C 10.00 µg/ml | 1 | 22 |
| C 2.50 µg/ml | 0 | 23 |
| C 0.60 µg/ml | 1 | 26 |
| C 0.15 µg/ml | 1 | 20 |
| C 0.00 µg/ml | 1 | 1 |

Incubation: 2 hours at 37° C., 25% serum from human volunteers A, B or C, as source of complement.

TABLE 16

ADCC (antibody-dependant cellular cytotoxicity) (specific lysis in %) of HT-1080FAP clone 33 target cells by human MNC (peripheral blood mononuclear cells) mediated by $L_AH_C$

| Concentration of antibody: | HT-1080FAP clone 33: | |
|---|---|---|
| [in µg/ml] | hIgG1 | $L_AH_C$ |
| 10 | 2 | 2 |
| 2.5 | 2 | 2 |
| 0.625 | 2 | 2 |
| 0.156 | 3 | 3 |
| 0 | 3 | 3 |

Incubation: 5 hours at 37° C., $10^4$ target cells and an effector:target cell ratio of 50:1.

Incubation: 5 hours at 37° C., $10^4$ target cells and an effector:target cell ration of 50:1.

TABLE 17

ADCC (antibody-dependent cellular cytotoxicity, specific lysis in %) of HT-1080FAP clone 33 target cells by LAK cells (lymphokine activated killer cells) mediated by $L_AH_C$

| Concentration of antibody: | HT-1080FAP clone 33: | |
|---|---|---|
| [in µg/ml] | hIgG1 | $L_AH_C$ |
| 10 | 12 | 14 |
| 2.5 | 14 | 17 |
| 0.625 | 14 | 21 |
| 0.156 | 15 | 21 |
| 0 | 14 | 14 |

Incubation: 5 hours at 37° C., $10^4$ target cells and an effector:target cell ration of 50:1.

Incubation: 5 hours at 37° C., $10^4$ target cells and an effector:target cell ration of 50:1.

Example 8

Immunohistochemical Analysis of Monoclonal Antibody $L_AH_C$ Binding to Normal and Neoplastic Human Tissues This experiment was performed to determine the binding characteristics of the humanized mAb $L_AH_C$ to normal and neoplastic human tissues.

The following antibodies were used: $L_AH_C$, cF19, and the negative control hIgG1 were directly biotinylated according to methods of the state of the art and used at concentrations of 2.5 to 0.25 mg/ml in 2% BSA/PBS (bovine serum albumin in phosphate-buffered saline). Murine mAb F19 was used as tissue culture supernatant of the F19 hybridoma, at dilutions of 1:5 to 1:10 in 2% BSA/PBS.

The following reagents were used for immunochemical assays: Streptavidin peroxidase complex (Vector Labs., Burlingame, Calif., USA), Avidin-biotin peroxidase complex (Vector Labs.), Biotinylated horse anti-mouse (Vector Labs.), DAB (diaminobenzidine, Sigma Chemical Co., St. Louis, Mo., USA), Harris' hematoxylin.

Fresh frozen tissue samples examined included the following: Normal colon, breast, lung, stomach, pancreas, skin, larynx, urinary bladder, smooth and skeletal muscle. Among the tumors tested were carcinomas from breast, colon, lung, esophagus, uterus, ovary, pancreas, stomach, and head and neck.

An indirect immunoperoxidase method was carried out according to state of the art methods (Garin-Chesa, P., et al., "Cell surface glycoprotein of reactive stromal fibroblasts as a potential antibody target in human epithelial cancers," Proc. Natl. Acad. Sci. USA 87:7235–7239 (1990)) on five micrometer thickness fresh frozen sections. DAB was used as a substrate for the final reaction product. The sections were counterstained with Harris' hematoxylin and examined for antigen expression.

$L_AH_C$ Expression in Normal Human Tissues

The normal tissues tested were negative for $L_AH_C$ expression, except for the normal pancreas in which a subset of positive endocrine cells in the islets of Langerhans (A cells) were identified with $L_AH_C$, cF19 and F19. (Table 18). No immunoreactivity was observed with the hIgG1 (human immunoglobulin IgG1 subclass) used as a negative control.

$L_AH_C$ Expression in Tumors

In the tumor samples, $L_AH_C$, cF19 and F19 showed an indistinguishable pattern of expression in the tumor stromal fibroblasts. A strong and homogeneous expression was found in the majority of the cases examined, especially in the cancer samples derived from breast, colon, lung, pancreas and in the squamous cell carcinomas (SQCC) of the head and neck tested (Table 18). No immunoreactivity was observed with the hIgG1 used as negative control.

$L_AH_C$, cF19 and F19 showed immunoreactivity with the tumor stromal fibroblasts in the epithelial cancer samples tested. No $L_AH_C$ or F19 immuno-reactivity was seen with either the fibrocytes of the normal organ mesenchyme or the parenchymal cells of normal adult organs. Anti-FAP immunoreactivity was only observed in a subset of endocrine cells in the pancreatic islets, presumably glucagon-producing A cells, and in four of nine uterine samples tested, representing subsets of stromal fibroblasts in these tissues.

Immunohistochemical analysis of $L_AH_C$ in normal human tissues and FAP-expressing human carcinomas showed indistinguishable patterns of binding for $L_AH_C$, cF19 and murine mAb F19.

TABLE 18

Immunoreactivity of mAbs $L_AH_C$, cF19 and F19 with normal human tumor samples

| Tissue type | No. | $L_AH_C$ | cF19 | F19 |
|---|---|---|---|---|
| Breast | 4 | | | |
| Epithelial cell ducts/acini | | – | – | – |
| Myoepithelial cells | | – | – | – |
| Connective tissue | | – | – | – |
| Blood vessels | | – | – | – |
| Colon | 6 | | | |
| Crypts of Lieberkühn | | – | – | – |
| Connective tissue | | – | – | – |
| Lymphoid tissue | | – | – | – |
| Smooth muscle | | – | – | – |
| Blood vessels | | – | – | – |
| Myenteric plexus | | – | – | – |
| Lung | 4 | | | |
| Bronchus: | | | | |
| Bronchial epithelium | | – | – | – |
| Hyaline cartilage | | – | – | – |
| Connective tissue | | – | – | – |
| Mucous glands | | – | – | – |
| Alveolus: | | | | |
| Pneumocytes (type I/II) | | – | – | – |
| Alveolar phagocytes | | – | – | – |
| Alveolar capillaries | | – | – | – |
| Stomach | 3 | | | |
| Surface epithelium | | – | – | – |
| Gastric glands | | – | – | – |
| Chief cells | | – | – | – |
| Parietal (oxyntic) cells | | – | – | – |
| Mucous cells | | – | – | – |
| Neuroendocrine cells | | – | – | – |
| Connective tissue | | – | – | – |
| Blood vessels | | – | – | – |
| Smooth muscle | | – | – | – |
| Esophagus | 1 | | | |
| Surface epithelium | | – | – | – |
| Connective tissue | | – | – | – |
| Small intestine | 1 | | | |
| Epithelium of villi & crypts | | – | – | – |
| Connective tissue | | – | – | – |
| Smooth muscle | | – | – | – |
| Blood vessels | | – | – | – |
| Lymphoid tissue | | – | – | – |
| Urinary bladder | 2 | | | |
| Urothelium | | – | – | – |
| Connective tissue | | – | – | – |
| Smooth muscle | | – | – | – |
| Blood vessels | | – | – | – |
| Pancreas | 3 | | | |
| Duct epithelium | | – | – | – |
| Acinar epithelium | | – | – | – |
| Islets of Langerhans: | | | | |
| B-cells | | – | – | – |
| A-cells | | +* | +* | +* |
| D-cells | | – | – | – |
| Connective tissue | | – | – | – |
| Blood vessels | | – | – | – |
| Nerves | | – | – | – |
| Larynx | 1 | | | |
| Squamous epithelium | | – | – | – |
| Mucous glands | | – | – | – |
| Connective tissue | | – | – | – |
| Hyaline cartilage | | – | – | – |
| Blood vessels | | – | – | – |
| Skeletal muscle | | – | – | – |
| Lymph node | 1 | | | |
| Lymphoid cells | | – | – | – |
| Lymph sinuses | | – | – | – |
| Connective tissue | | – | – | – |
| Blood vessels | | – | – | – |
| Spleen | 1 | | | |
| Red & white pulp | | – | – | – |
| Sinuses | | – | – | – |
| Connective tissue | | – | – | – |
| Liver | 1 | | | |
| Hepatocytes | | – | – | – |
| Bile ducts | | – | – | – |
| Portal triad | | – | – | – |
| Thyroid gland | 2 | | | |
| Follicular epithelium | | – | – | – |
| Parafollicular cells | | – | – | – |
| Connective tissue | | – | – | – |
| Prostate gland | 1 | | | |
| Glandular epithelium | | – | – | – |
| Stroma | | – | – | – |
| Testicle | 1 | | | |
| Seminiferous tubules | | – | – | – |
| Stroma | | – | – | – |
| Ovary | 3 | | | |
| Follicles | | – | – | – |
| Stroma | | – | – | – |
| Uterine cervix | 1 | | | |
| Epithelium | | – | – | – |
| Stroma | | – | – | – |
| Uterus | 9 | | | |
| Endometrium: | | | | |
| glands | | – | – | – |
| stroma | | +** | +** | +** |
| blood vessels | | – | – | – |
| Myometrium | | – | – | – |
| Cerebral cortex | 1 | | | |
| Neurons | | – | – | – |
| Neurological cells | | – | – | – |
| Blood vessels | | – | – | – |
| Cerebellum | 1 | | | |
| Molecular layer | | – | – | – |
| Granular cell layer | | – | – | – |
| Purkinje cells | | – | – | – |
| Blood vessels | | – | – | – |
| Skin | 3 | | | |
| Squamous epithelium | | – | – | – |
| Melanocytes | | – | – | – |

TABLE 18-continued

Immunoreactivity of mAbs $L_AH_C$, cF19 and F19 with normal human tumor samples

| Tissue type | No. | $L_AH_C$ | cF19 | F19 |
|---|---|---|---|---|
| Skin appendages | | – | – | – |
| Connective tissue | | – | – | – |
| Blood vessels | | – | – | – |

Acetone-fixed frozen sections were tested by the avidin-biotin complex immunoperoxidase procedure.
No number of tissue samples derived from different individuals tested.
*Identification of A-cells, based on morphology and location within the islets.
**Positive immunoreactivity in the stroma in 4 out of 9 samples tested. The positive samples represent early (x2) and intermediate (x2) phase proliferative endometrium.

Example 9

Species Specificity of $L_AH_C$ Binding in Tissue Sections

This experiment was conducted to assess the reactivity of $L_AH_C$ with tissues from mouse, rat, rabbit and cynomolgus monkeys by immunohistochemical methods.

Also used in these tests were cF19 and human IgG1 (hIgG1) as negative controls. The reagents used for immunohistochemistry were Streptavidin peroxidase complex (Vector Labs., Burlingame, Calif., USA), DAB (Sigma Chemical Co., St. Louis, Mo., USA) and Harris' hematoxylin.

The following fresh frozen tissue samples from mouse, rat, rabbit and cynomolgus were tested: Brain, liver, lung, kidney, stomach, pancreas, intestine, thymus, skin, muscle, heart, spleen, ovary, uterus and testes. As positive control, sections from normal human pancreas and a breast carcinoma sample were included in every assay.

Immunohistochemistry

An indirect immunoperoxidase method was carried out as described in the state of the art (Garin-Chesa, P., et al., "Cell surface glycoprotein of reactive stromal fibroblasts as a potential antibody target in human epithelial cancers," *Proc. Natl. Acad. Sci. USA* 87:7235–7239 (1990)) on five micrometer thickness fresh frozen sections. The antibodies $L_AH_C$, cF19 and hIgG1 (at 1 µg/ml) were biotinylated according to the state of the art and were detected with streptavidin peroxidase complex. DAB was used as a substrate for the final reaction product. The sections were counterstained with Harris' hematoxylin and examined for antigen expression.

The normal tissues tested did not react with either $L_AH_C$ or cF19 in the experiments (Table 1).

The normal human pancreas used as positive control showed $L_AH_C$ and cF19 binding in a subset of endocrine cells in the islets of Langerhans as previously described for F19. In addition, binding of $L_AH_C$ and cF19 was seen in the tumor stromal fibroblasts in the breast carcinoma sample.

Immunohistochemical analysis of normal tissues from mouse, rat, rabbit and cynomolgus failed to detect any binding of either $L_AH_C$ or cF19, in the experiments performed.

TABLE 19

Binding Of $L_AH_C$ to tissue sections of non-human species, as determined by immunohistochemistry

| Organ/Tissue type | | Mouse | Rat | Rabbit | Cynomigus |
|---|---|---|---|---|---|
| Brain | Cerebral cortex | – | – | – | |
| | Cerebellum | | | | – |
| Liver | Hepatocytes | – | – | – | – |
| | Portal triad | – | – | – | – |
| Lung | Bronchi | – | – | – | – |
| | Alveoli | – | – | – | – |
| Kidney | Glomeruli | – | – | – | – |
| | Tubular epithelium | – | – | – | – |
| Stomach | Glandular epithelium | – | – | – | – |
| | Smooth muscle | – | – | – | – |
| Pancreas | Exocrine acini | – | – | – | – |
| | Endocrine islets | – | – | – | – |
| Intestine | Glandular epithelium | – | – | – | – |
| | Smooth muscle | – | – | – | – |
| Thymus | Lymphocytes | – | – | – | – |
| Skin | Keratinocytes | – | – | – | – |
| | Sweat glands | – | – | – | – |
| | Hair follicles | – | – | – | – |
| Skeletal muscle | | | | | |
| Heart | | – | – | – | – |
| Spleen | Lymphocytes | – | – | – | – |
| Ovary | Follicular epithelium | – | – | – | – |
| | Stroma | – | – | – | – |
| Uterus | Myometrium | – | – | – | – |
| | Cervix uteri | – | – | – | – |
| Testis | Tubular epithelium | nt | nt | nt | – |
| Connective tissue | | – | – | – | – | nt = not tested

Example 10

Construction of Cell Lines Producing Chimeric and Reshaped Anti-FAP Monoclonal Antibodies The objective of this experiment was to demonstrate stable cell lines according to the invention expressing $L_AH_C$, $L_AH_A$, $L_BH_B$, $L_BH_D$, and cF19 in CHO DG44 cells. Stable cell lines transfected with humanized or chimeric F19 antibodies were produced and their identity was confirmed by PCR amplification of heavy and light variable regions using genomic DNA derived from each transfectant as template.

CHO DG44 cells maintained under serum-free conditions in SFM-II medium. Lipofectin and SFM-II serum-free medium were obtained from Gibco/BRL. Geneticin and all restriction enzymes were obtained from Boehringer Mannheim. Pfu polymerase was obtained from Stratagene.

DNA for transfections was purified from *E. Coli* cells using QiaFilter Maxi Cartridges (Qiagen) as directed by the manufacturer. All DNA preparations were examined by restriction enzyme digestion. Sequences of $L_AH_C$ variable regions in their respective vectors were confirmed using an ABI PRISM 310 Sequencer (Perkin-Elmer).

Further information regarding the vectors and DNA sequences employed is available in the prior examples.

Transfection of CHO DG44 Cells

Cells in logarithmic growth were plated into 6 well plates containing 1 ml fresh SFM-II medium. Plasmids encoding heavy and light chains of humanized or chimeric F19 versions were cotransfected into CHO DG44 cells using liposomal transfection. Liposomes were prepared using 6 µl lipofectin reagent and 0.5 µg of each vector (one for the desired heavy chain and one for the light) as described for LipofectAMINE transfections except that SFM-II medium was used to dilute all reagents. Twenty-four hours later, cells were diluted 1:10 into SFM-II medium containing 300 μg/ml Geneticin. After the initial phase of cell killing was over (10–14 days), the concentration of Geneticin was reduced to 200 mg/ml and methotrexate was added to a final concentration of 5 nM. Methotrexate concentrations were increased after 10–14 days to a final concentration of 20 nM.

PCR Amplification of Transfectant DNA $10^7$ CHO DG44 cells were centrifuged in an Eppendorf microcentrifuge briefly at full speed, washed once with PBS, and pelleted once again. Genomic DNA was prepared by ethanol precipitation after SDS lysis and Proteinase K treatment of the cell pellets.

A mixture containing one of the following primer pairs, dNTPs, buffer, and Pfu polymerase was used to amplify either the heavy or light chain variable region using genomic DNA as template. The resulting PCR products were digested with the appropriate restriction enzyme and analyzed by agarose gel electrophoresis to confirm their identity.

```
Light chain primer set;
5'-GAG ACA TTG TGA CCC      PKN 1690 (SEQ ID NO:98)
AAT CTC C-3'
5'-GAC AGT CAT AAA CTG      PKN.1930.R (SEQ ID NO:99)
CCA CAT CTT C-3'

Heavy chain primer set:
5'-TTG ACA CGC GTC TCG      PG 5863 (SEQ ID NO:100)
GGA AGC TT-3'
5'-GGC GCA GAG GAT CCA      PG 6332.R (SEQ ID NO:101)
CTC ACC T-3'
```

The undigested heavy chain PCR product has a predicted size of 469 bp while the light chain PCR product has a predicted size of 286 bp. Verification of identity was determined by restriction enzyme digest with BstEII (heavy chain) or NlaIV (light chain).

CHO cell lines were transfected with $L_AH_C$, $L_AH_A$, $L_BH_B$ and $L_BH_D$, as well as cF19. Geneticin-resistant cells were obtained and these cells were further selected for resistance to methotrexate. PCR amplification, followed by restriction enzyme cleavage of the light and heavy chain DNA produced the expected bands and confirmed the identity of $L_AH_C$, $L_BH_B$, $L_AH_A$ and $L_BH_D$ transfectants.

The cells described were maintained under serum-free conditions at all times and were not treated with animal-derived products such as trypsin.

Producer cell lines transfected with expressing monoclonal $L_AH_C$, $L_AH_A$, $L_BH_B$, $L_BH_D$ and cF19 antibodies were produced. Their identities were confirmed using PCR amplification and restriction enzyme cleavage of the resulting PCR products of both their heavy and light chain variable regions.

Example 11

Expression of Antibody Proteins in Chinese Hamster Ovary DG 44 Cells and Their Purification The objective of this experiment was to express and purify $L_AH_C$, $L_AH_A$, $L_BH_B$, and $L_BH_D$ mAbs to enable their characterization. Other goals included the establishment of a quantitative ELISA to permit measurement of antibody concentrations in both crude media samples as well as purified Ig samples and determination of relative expression levels of various humanized F19 constructs using this assay.

Serum-free CHO DG44 cells and USP-grade methotrexate were obtained from the Biotechnical Production Unit of the Dr. Karl Thomae GmbH, Biberach, Germany; both products are also commercially available. Cells were maintained under serum-free conditions at all times. SFM-II serum-free medium was obtained from Gibco/BRL. Protein A agarose was from Pierce Chemical (Indianapolis, Ind., USA). Human IgG1 standards (Cat. No. I3889), p-Nitrophenyl phosphate tablets (N 2640), bovine serum albumin (BSA) (A 7906), and goat anti-human kappa chain specific alkaline phosphatase-conjugated antibody (A 3813) were obtained from Sigma Chemical (St. Louis, Mo., USA). Goat anti-human gamma-chain specific alkaline phosphatase-conjugated antibody was obtained from Jackson Immunoresearch Laboratories (through Stratech Scientific). Tris-buffered saline (TBS) consisted of 150 mM NaCl, 50 mM Tris, pH 7.5.

Cell Culture Conditions for Antibody Expression

Cells were cultured and maintained-in T-175 flasks in SFM-II serum-free medium without agitation. The medium contained 200 μg/ml Geneticin and 20 nM methotrexate without antibiotics. Cells were passaged by dilution, were not adherent, and grew in small clusters. When the cells reached stationary phase, the medium was collected and centrifuged to remove cells and frozen at −20° C. until needed.

Purification of $L_AH_C$

All purification steps were carried out at 4° C. A C10/10 column (Pharmacia Fine Chemicals) was packed with Protein A agarose (3 ml bed volume). The column was washed with TBS and preeluted once with 0.1 M Na citrate, pH 3.0 to insure that no loosely bound material remained on the column. The column was then immediately reequilibrated with TBS and stored at 4° C. Spent culture supernatants were thawed and centrifuged at 10,000×g for 30 minutes prior to Protein A chromatography to remove debris and diluted with an equal volume of TBS. This material was loaded onto the Protein A column at 0.5 ml/minute using a P-1 peristaltic pump (Pharmacia) and washed with TBS until the absorbance at 280 nm was undetectable. Elution of the antibody was initiated with 0.1 M Na citrate pH 3.0 at approximately 0.2 ml/minute. The elution was monitored at 280 nm and one ml fractions of the eluted material were collected into tubes containing sufficient Tris base pH 9 to neutralize the citrate buffer. Protein-containing fractions were pooled and concentrated using an Amicon filtration apparatus with a YM-30 filter and dialyzed against PBS. The column was immediately regenerated with TBS. Protein dye-binding assays were performed with the BioRad (Hercules, Calif.) protein determination kit, according to the manufacturer's instructions, using bovine serum albumin as a standard.

Human IgG (Gamma Immunoglobulin) ELISA

ELISA plates were coated overnight with 100 μl of goat anti-human gamma-chain specific alkaline phosphatase-conjugated antibody at 0.4 mg/ml in coating buffer at 4° C. Coating antibody was removed and plates were blocked with 2% BSA in PBS for 2 hours. All subsequent steps were performed at 37° C. Blocking buffer was replaced with antibody samples or human IgG1 standard diluted in dilution buffer, serially diluted in a 200 ml volume, and incubated for one hour. Negative controls included dilution buffer and/or culture medium of nontransfected cells. Wells were washed and 100 μl of goat anti-human kappa chain specific alkaline phosphatase-conjugated antibody diluted 1:5000 was added and incubated for one hour. Wells were washed and 100 µl reaction buffer was added and incubated for 30 minutes. The reaction was stopped by addition of 1 M NaOH and absorbance read at 405 nm in an ELISA plate reader. Results were analyzed by four-parameter iterative curve fitting.

Amino acid analysis was performed according to methods available in the state of the art.

Monoclonal antibody $L_A H_C$ was produced and purified to homogeneity using Protein A affinity chromatography. ELISA assays using human IgG1 as standard indicated $L_A H_C$ recoveries exceeding 70%. The purity of the material was estimated to be >90% by SDS-polyacrylamide gel electrophoresis. Representative expression data and typical purification yields are shown in Table 20.

TABLE 20

Expression data and purification yields FAP antibody proteins in CHO cells

| Antibody | Expression levels in crude media samples (ELISA) | Purified antibody yields | Yield improvement [purified antibody] |
|---|---|---|---|
| $L_A H_C$ | 7–10 mg/l | ~5–7 mg/l | 500–700 |
| $L_A H_A$ | 5–7 mg/l | ~3–4 mg/l | 300–400 |
| $L_B H_B$ | 0.5–1 mg/l | ~0.2–0.5 mg/l | 20–50 |
| $L_B H_D$ | 0.8–1.5 mg/l | ~0.3–0.8 mg/l | 30–60 |
| Chimeric F19 | ~0.02 mg/l | <0.01 mg/l | 1 |

Representative expression data for each of the anti-FAP antibodies produced in this study are shown. Recoveries after Protein A agarose affinity chromatography were based on protein dye-binding measurements of the purified Ig using BSA as a standard.

Example 12

Binding of Monoclonal Antibody $L_A H_C$ to Isolated Recombinant Human FAP

The objective of this study was to characterize binding of $L_A H_C$ to isolated recombinant human FAP.

CD8-FAP ELISA

ELISA plates were coated overnight with 100 µl of mouse anti-rat antibody (Sigma Chemical R0761) at 1:2000 in coating buffer at 4° C. Coating antibody was removed and plates were blocked with 2% BSA in PBS for one hour. All subsequent steps were performed at room temperature. Blocking buffer was replaced with 100 ml of 1 µg/ml rat anti-CD8 antibody (Pharmingen 01041D) and incubated for one hour. Plates were washed and 100 µl CD8-FAP culture supemnatant (see example 14) (1:2 in PBS) was added and allowed to bind for one hour. Plates were washed and antibody samples were added (two-fold serial dilutions) in a 100 µl volume and incubated for one hour. Negative controls included human IgG and/or culture medium of nontransfected cells. Wells were washed and 100 µl of horse radish peroxidase (HRP) conjugated mouse anti-human IgG1 antibody (Zymed 05-3320) diluted 1:500 in dilution buffer were added and incubated for one hour. Wells were washed and 100 µl HRP substrate, (azino-bis(3-ethylbenzthiazoline 6-sulfonic) acid, Sigma Chemical A9941), were added and incubated for 60 minutes. The reaction was stopped by addition of 1 M NaOH and absorbance read at 405/490 nm in an ELISA plate reader. Results were analyzed by four-parameter curve iterative curve fitting.

Alternatively, plates were coated directly with cF19. FAP (recombinant human FAP, see example 13) was allowed to bind to these plates as above and biotinylated $L_A H_C$ (~1 µg/ml) was then added. Antibody binding was detected with HRP-streptavidin conjugate as above.

Solubilization of Membrane-bound Human FAP

FAP-expressing 293FAP I/2 cells or control 293 cells were washed with PBS and lysed with 1% Triton X-114 in Tris-buffered saline. Nuclei and debris were removed by centrifugation at 10,000×g. The supernatant was phase-partitioned (Estreicher, A., et al., "Characterization of the cellular binding site for the urokinase-type plasminogen activator," *J. Biol. Chem.* 264:1180–1189 (1989)) to enrich membrane proteins. The detergent phase was collected and diluted in buffer containing 1% Empigen BB (Calbiochem) to prevent reaggregation of the Triton X-114. This material was subjected to Concanavalin A agarose chromatography (Rettig, W. J., et al., "Regulation and heteromeric structure of the fibroblast activation protein in normal and transformed cells of mesenchymal and neuroectodermal origin," *Cancer Res* 53:3327–3335 (1993)).

Biotinylation of $L_A H_C$ $L_A H_C$ (1–2 mg) was dialyzed against 50 mM bicarbonate buffer and biotinylated with a ten-fold molar excess of sulfosuccinimidyl-6-biotinamido hexanoate (NHS-LC biotin, Pierce Chemical, Rockford, Ill., USA) for 2 hours at room temperature. Unreacted product was removed by repeated microdialysis in a microconcentrator.

Transient Transfections

COS-7 cells (American Type Tissue Culture Collection, reference number CRL 1651) were cotransfected by electroporation with the heavy and light chain vectors encoding $L_A H_C$.

Anti-CD8 monoclonal antibody was immobilized onto microtiter plates. CD8-FAP from medium of insect cells infected with CD8-FAP baculovirus was allowed to bind to these plates. Spent medium from COS-7 cell cultures transiently transfected with two separate vectors encoding $L_A H_C$ was serially diluted and added to the wells containing the immobilized CD8-FAP. $L_A H_C$ bound to isolated immobilized CD8-FAP protein (FIG. 35). Culture supernatants from mock-transfected COS-7 cells failed to demonstrate binding.

Recombinant membrane-bound FAP from detergent extracts of 293FAP I/2 cells or control extracts was serially diluted and immobilized via chimeric F19 monoclonal antibody bound to microtiter plates. Biotinylated $L_A H_C$ bound recombinant human FAP immobilized with cF19 (FIG. 36) in a concentration-dependent manner.

$L_A H_C$ recognized isolated immobilized recombinant human FAP carrying the epitope for murine F19. $L_A H_C$ bound to both CD8-FAP produced in insect cells, as well as FAP protein produced in 293FAP I/2 cells.

Culture supernatants from COS-7 cells transfected with either heavy and light chain vectors encoding $L_A H_C$ or without DNA (Control) were collected three days posttransfection. CD8-FAP was immobilized via an anti-CD8 antibody as described in the text. Serial dilutions of the COS-7 supernatants were allowed to bind to the immobilized CD8-FAP and subsequently detected with an HRP-conjugated anti-human IgG1 antibody.

Detergent extracts of FAP-expressing 293FAP I/2 cells or control 293 cells were serially diluted and added to cF19-coated microtiter plates. Biotinylated $L_A H_C$ was added and binding of biotinylated $L_A H_C$ was detected with HRP-conjugated streptavidin.

Example 13

Characterization of HT-1080 Fibrosarcoma Cells and 293 Human Embryonic Kidney Cells Transfected with cDNA for Human FAP Fibroblast activation protein (FAP) is a cell-surface, membrane-bound protein which carries the F19 epitope and is expressed on tumor stromal fibroblasts. Cell lines expressing recombinant FAP protein and matched controls lacking FAP were generated for the characterization of anti-FAP monoclonal antibodies.

Cells used were HT-1080 cells (reference number CCL 121) and 293 human embryonic kidney cells (reference number CRL 1573) were obtained from the American Type Culture Collection (Maryland, USA). Transfectam was obtained from Promega (Madison, Wis.). Geneticin and all restriction enzymes were obtained from Boehringer Mannheim. DNA for transfections was purified from *E. coli* cells using QiaFilter Maxi Cartridges (Qiagen) as directed by the manufacturer. All DNA preparations were examined by restriction enzyme digestion. Vector sequences were confirmed using an ABI PRISM 310 Sequencer.

Further information regarding the vectors and DNA sequences employed has been described in Scanlan, M. J., et al., "Molecular cloning of fibroblast activation protein alpha, a member of the serine protease family selectively expressed in stromal fibroblasts of epithelial cancers," *Proc. Natl. Acad. Sci. USA* 89:10832–10836 (1992). The FAP cDNA sequence has been deposited in Genbank (accession number HS09287). cl Cell Culture and Immunoassays HT-1080 cells were transfected with 1 mg DNA using Transfectam according to the manufacturer's instructions. Human embryonic kidney 293 cells were transfected by calcium phosphate transfection (Brann, M. R., et al., "Expression of cloned muscarinic receptor in A9 L cells," *Mol. Pharmacol.* 32:450–455 (1987)) with 10 mg DNA. Twenty-four hours later, cells were diluted 1:10 into fresh medium containing 200 mg/ml Geneticin. Colonies were picked and examined by immunofluorescence for FAP expression as described in Rettig, W. J., et al., "Cell-surface glycoproteins of human sarcomas: differential expression in normal and malignant tissues and cultured cells," *Proc. Natl. Acad. Sci. USA* 85:3110–3114 (1988).

Immunoprecipitations with cF19 were performed with metabolically labelled cells as described in Rettig, W. J., et al., "Regulation and heteromeric structure of the fibroblast activation protein in normal and transformed cells of mesenchymal and neuroectodermal origin," *Cancer Res.* 53:3327–3335 (1993).

HT-1080 and 293 cells were tested for FAP antigen expression in immunofluorescence assays with anti-FAP antibodies and were found to be antigen-negative. Transfection of these cells with FAP.38 vector resulted in the generation of Geneticin-resistant colonies. Isolated colonies were picked and analyzed by immunofluorescence for FAP expression. Two cell clones were identified, designated HT-1080FAP clone 33 and 293FAP I/2, which express cell surface-bound FAP protein, as recognized by cF19 antibody. Staining of nonpermeabilized HT-1080FAP clone 33 cells and 293FAP I/2 with cF19 antibody confirmed the cell surface localization of the FAP protein.

Immunoprecipitation of radiolabelled FAP protein with cF19 from extracts of 35S-methionine labelled HT-1080FAP clone 33 cells or 293FAP I/2 cells resulted in the appearance of a 93 kilodalton band after autoradiography. This band is not detectable in immunoprecipitates of parental HT-1080 or 293 cell extracts.

Two stably transfected cell lines, HT-1080FAP clone 33 and 293FAP I/2, express FAP on the cell surface as determined in immunological assays with anti-FAP mAbs. Neither parental HT-1080 cells nor parental 293 cells express detectable levels of FAP.

Example 14

Generation and Characterization of CD8-FAP Fusion Protein

A soluble form of human FAP (fibroblast activation protein) in the form of a CD8-FAP fusion protein was produced in insect cells for the characterization of $L_A H_C$ containing the binding site for anti-FAP mAbs. Murine CD8 was chosen to permit secretion of the protein and to provide an additional epitope tag.

The cDNA encoding the extracellular domain of CD8, consisting of the first 189 amino acids of murine CD8α (Genbank M12825), was linked to that of the extracellular domain of FAP (amino acids 27 to 760), essentially as described by Lane, et al. (Lane, P., et al., "Soluble CD40 ligand can replace the normal T cell-derived CD40 ligand signal to B cells in T cell-dependent activation," *J. Exp. Med.* 177:1209–1213 (1993)) using standard PCR protocols. The authenticity of all clones was verified by DNA sequencing. The resulting DNA was inserted into the pVL1393 vector (Invitrogen) and transfection of Sf9 cells (Invitrogen) with this vector and amplification of the resulting recombinant baculovirus were performed as described (*Baculovirus Expression Vectors. A Laboratory Manual*, O'Reilly, D. R., et al., eds., Oxford University Press:, New York (1994)). The spent medium of High Five™ cells (Invitrogen) infected with recombinant CD8-FAP baculovirus for four days was collected and cleared by ultracentrifugation.

The CD8-FAP ELISA (enzyme-linked immunosorbent assay) has been described above (example 12).

Insect cell cultures infected with CD8-FAP virus secreted a fusion protein into the medium which carries the F19 epitope and is recognized by an anti-FAP antibody (FIG. 1). Neither the cell culture medium alone nor medium from insect cells infected with CD8-CD40L fusion protein bound anti-FAP antibody.

Soluble CD8-FAP protein carrying the F19 epitope was secreted into the medium of infected insect cell cultures. Culture supernatant from cells infected with a control construct did not contain antigen bearing the F19 epitope.

A soluble form of FAP, CD8-FAP, was produced in insect cells and CD8-FAP was shown to carry the epitope recognized by cF19.

Supernatants from insect cells infected with recombinant baculovirus encoding either CD8-FAP or CD8-CD40L fusion protein were collected four days postinfection. Cell culture medium without cells was used as an additional control (medium). Serial dilutions of these materials were added to anti-CD8 antibody-coated microtiter plates and allowed to bind. cF19 (1 mg/ml) was subsequently added and allowed to bind. Bound cF19 was detected with horseradish peroxidase-conjugated anti-human antibody.

What is claimed is:

1. An antibody protein having the six complementary determining regions of the monoclonal antibody F19 (ATCC Accession No. HB 8269) and containing a variable region of the light chain as set forth in SEQ ID NO:2 or SEQ ID NO:6, said antibody protein specifically binding to fibroblast activation protein, and having framework modifications resulting in improved producibility in COS or CHO cells as compared to a chimeric antibody having the variable regions of F19 and foreign constant regions.

2. The antibody protein of claim 1, containing a variable light chain as set forth in SEQ ID NO:2.

3. The antibody protein of claim 2, wherein the variable region of the light chain is encoded by a nucleotide sequence as set forth in SEQ ID NO:1.

4. The antibody protein of claim 1, containing the variable region of the light chain as set forth in SEQ ID NO:6.

5. The antibody protein of claim 4, wherein the variable region of the light chain is encoded by a nucleotide sequence as set forth in SEQ ID NO:5.

6. The antibody protein of claim 1 containing a variable region of the heavy chain as set forth in SEQ ID NOS:8, 10, 12 or 14.

7. The antibody protein of claim 6, wherein the variable region of the heavy chain is encoded by a nucleotide sequence as set forth in SEQ ID NOS:7, 9, 11 or 13.

8. The antibody protein of claim 1 containing the variable region of the light chain as set forth in SEQ ID NO:2 and the variable region of the heavy chain as set forth in SEQ ID NO:12.

9. The antibody protein of claim 8, wherein the variable region of the light chain is encoded by a nucleotide sequence as set forth in SEQ ID NO:1 and the variable region of the heavy chain is encoded by a nucleotide sequence as set forth in SEQ ID NO:11.

10. The antibody protein of claim 8 containing the constant region of the light chain as set forth in SEQ ID NO: 20 and the constant region of the heavy chain as set forth in SEQ ID NO:22.

11. The antibody protein of claim 1 containing the variable region of the light chain as set forth in SEQ ID NO:2 and the variable region of the heavy chain as set forth in SEQ ID NO:8.

12. The antibody protein of claim 11, wherein the variable region of the light chain is encoded by a nucleotide sequence as set forth in SEQ ID NO:1 and the variable region of the heavy chain is encoded by a nucleotide sequence as set forth in SEQ ID NO:7.

13. An antibody protein comprising a light chain variable region having three complementary determining regions of monoclonal antibody F19, a heavy chain variable region having three complementary determining regions of monoclonal antibody F19, a light chain constant region and a heavy chain constant region;

wherein said light chain variable region has an amino acid sequence as set forth in SEQ ID NO:2.

14. The antibody protein of claim 13 wherein said heavy chain variable region has an amino acid sequence as set forth in SEQ ID NO:12.

15. The antibody protein of claim 13 wherein said light chain constant region has an amino acid sequence as set forth in SEQ ID NO:20 and wherein said heavy chain constant region has an amino acid sequence as set forth in SEQ ID NO:22.

16. The antibody protein of claim 13 which is conjugated to a radioisotope.

17. A composition comprising the antibody protein of claim 13, and a pharmaceutically acceptable carrier.

18. The antibody protein of claim 16, wherein the radioisotope is selected from the group consisting of $^{131}I$, $^{125}I$, $^{186}Re$, $^{188}Re$ and $^{90}Y$.

19. The antibody protein of claim 14 further containing an amino acid sequence as set forth in SEQ ID NO:20 and an amino acid sequence as set forth in SEQ ID NO:22.

* * * * *

SEQUENCE LISTING

<160> NUMBER OF SEQ ID NOS: 108

<210> SEQ ID NO 1
<211> LENGTH: 339
<212> TYPE: DNA
<213> ORGANISM: Homo sapiens

<400> SEQUENCE: 1

| gacattgtga | tgacccaatc | tccagactct | ttggctgtgt | ctctagggga | gagggccacc | 60 |
| atcaactgca | agtccagtca | gagccttta | tattctagaa | atcaaaagaa | ctacttggcc | 120 |
| tggtatcagc | agaaaccagg | acagccaccc | aaactcctca | tcttttgggc | tagcactagg | 180 |
| gaatctgggg | tacctgatag | gttcagtggc | agtgggtttg | ggacagactt | caccctcacc | 240 |
| attagcagcc | tgcaggctga | agatgtggca | gtttattact | gtcagcaata | ttttagctat | 300 |
| ccgctcacgt | tcggacaagg | gaccaaggtg | gaaataaaa | | | 339 |

<210> SEQ ID NO 2
<211> LENGTH: 113
<212> TYPE: PRT
<213> ORGANISM: Homo sapiens

<400> SEQUENCE: 2

Asp Ile Val Met Thr Gln Ser Pro Asp Ser Leu Ala Val Ser Leu Gly
 1               5                  10                  15
Glu Arg Ala Thr Ile Asn Cys Lys Ser Ser Gln Ser Leu Leu Tyr Ser
            20                  25                  30
Arg Asn Gln Lys Asn Tyr Leu Ala Trp Tyr Gln Gln Lys Pro Gly Gln
        35                  40                  45
Pro Pro Lys Leu Leu Ile Phe Trp Ala Ser Thr Arg Glu Ser Gly Val
    50                  55                  60
Pro Asp Arg Phe Ser Gly Ser Gly Phe Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Phe Ser Tyr Pro Leu Thr Phe Gly Gln Gly Thr Lys Val Glu Ile
            100                 105                 110
Lys

<210> SEQ ID NO 3
<211> LENGTH: 339
<212> TYPE: DNA
<213> ORGANISM: Homo sapiens

<400> SEQUENCE: 3

| gacattgtga | tgacccaatc | tccagactct | ttggctgtgt | ctctagggga | gagggccacc | 60 |
| atcaactgca | agtccagtca | gagccttta | tattctagaa | atcaaaagaa | ctacttggcc | 120 |
| tggttccagc | agaaaccagg | acagccaccc | aaactcctca | tcttttgggc | tagcactagg | 180 |
| gaatctgggg | tacctgatag | gttcagtggc | agtgggtttg | ggacagactt | caccctcacc | 240 |
| attagcagcc | tgcaggctga | agatgtggca | gtttatgact | gtcaacaata | ttttagctat | 300 |
| ccgctcacgt | tcggacaagg | gaccaaggtg | gaaataaaa | | | 339 |

<210> SEQ ID NO 4
<211> LENGTH: 113
<212> TYPE: PRT

<213> ORGANISM: Homo sapiens

<400> SEQUENCE: 4

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Phe Gln Gln Lys Pro Gly Gln
        35                  40                  45

Pro Pro Lys Leu Leu Ile Phe Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Asp Cys Gln Gln
                85                  90                  95

Tyr Phe Ser Tyr Pro Leu Thr Phe Gly Gln Gly Thr Lys Val Glu Ile
                100                 105                 110

Lys

<210> SEQ ID NO 5
<211> LENGTH: 339
<212> TYPE: DNA
<213> ORGANISM: Homo sapiens

<400> SEQUENCE: 5
gacattgtga tgacccaatc tccagactct ttggctgtgt ctctagggga gagggccacc      60
atcaactgca agtccagtca gagcctttta tattctagaa atcaaaagaa ctacttggcc     120
tggtatcagc agaaaccagg acagccaccc aaactcctca tctattgggc tagcactagg     180
gaatctgggg tacctgatag gttcagtggc agtgggtttg ggacagactt caccctcacc     240
attagcagcc tgcaggctga agatgtggca gtttattact gtcagcaata ttttagctat     300
ccgctcacgt tcggacaagg gaccaaggtg gaaataaaa                            339

<210> SEQ ID NO 6
<211> LENGTH: 113
<212> TYPE: PRT
<213> ORGANISM: Homo sapiens

<400> SEQUENCE: 6

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Arg Asn Gln Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Phe Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
                100                 105                 110

Lys

-continued

<210> SEQ ID NO 7
<211> LENGTH: 372
<212> TYPE: DNA
<213> ORGANISM: Homo sapiens

<400> SEQUENCE: 7

| caggtgcaac tagtgcagtc cggcgccgaa gtgaagaaac ccggtgcttc cgtgaaagtc | 60 |
| agctgtaaaa ctagtagata caccttcact gaatacacca tacactgggt tagacaggcc | 120 |
| cctggccaaa ggctggagtg gataggaggt attaatccta acaatggtat tcctaactac | 180 |
| aaccagaagt tcaagggccg ggccaccttg accgtaggca gtctgccag caccgcctac | 240 |
| atggaactgt ccagcctgcg ctccgaggac actgcagtct actactgcgc cagaagaaga | 300 |
| atcgcctatg gttacgacga gggccatgct atggactact ggggtcaagg aacccttgtc | 360 |
| accgtctcct ca | 372 |

<210> SEQ ID NO 8
<211> LENGTH: 124
<212> TYPE: PRT
<213> ORGANISM: Homo sapiens

<400> SEQUENCE: 8

Gln Val Gln Leu Val Gln Ser Gly Ala Glu Val Lys Lys Pro Gly Ala
1               5                   10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Ala Thr Leu Thr Val Gly Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser
        115                 120

<210> SEQ ID NO 9
<211> LENGTH: 372
<212> TYPE: DNA
<213> ORGANISM: Homo sapiens

<400> SEQUENCE: 9

| caggtgcaac tagtgcagtc cggcgccgaa gtgaagaaac ccggtgcttc cgtgaaagtc | 60 |
| agctgtaaaa ctagtagata caccttcact gaatacacca tacactgggt tagacaggcc | 120 |
| cctggccaaa ggctggagtg gataggaggt attaatccta acaatggtat tcctaactac | 180 |
| aaccagaagt tcaagggccg ggccaccttg accgtaggca gtctgccag caccgcctac | 240 |
| atggaactgt ccagcctgcg ctccgaggac actgcagtct acttctgcgc cagaagaaga | 300 |
| atcgcctatg gttacgacga gggccatgct atggactact ggggtcaagg aacccttgtc | 360 |
| accgtctcct ca | 372 |

<210> SEQ ID NO 10
<211> LENGTH: 124
<212> TYPE: PRT

<213> ORGANISM: Homo sapiens

<400> SEQUENCE: 10

```
Gln Val Gln Leu Val Gln Ser Gly Ala Glu Val Lys Lys Pro Gly Ala
  1               5                  10                  15
Ser Val Lys Val Ser Cys Lys Thr Ser Arg Tyr Thr Phe Thr Glu Tyr
             20                  25                  30
Thr Ile His Trp Val Arg Gln Ala Pro Gly Gln Arg Leu Glu Trp Ile
         35                  40                  45
Gly Gly Ile Asn Pro Asn Asn Gly Ile Pro Asn Tyr Asn Gln Lys Phe
     50                  55                  60
Lys Gly Arg Ala Thr Leu Thr Val Gly Lys Ser Ala Ser Thr Ala Tyr
 65                  70                  75                  80
Met Glu Leu Ser Ser Leu Arg Ser Glu Asp Thr Ala Val Tyr Phe Cys
                 85                  90                  95
Ala Arg Arg Arg Ile Ala Tyr Gly Tyr Asp Glu Gly His Ala Met Asp
            100                 105                 110
Tyr Trp Gly Gln Gly Thr Leu Val Thr Val Ser Ser
        115                 120
```

<210> SEQ ID NO 11
<211> LENGTH: 372
<212> TYPE: DNA
<213> ORGANISM: Homo sapiens

<400> SEQUENCE: 11

```
caggtgcaac tagtgcagtc cggcgccgaa gtgaagaaac ccggtgcttc cgtgaaagtc    60
agctgtaaaa ctagtagata caccttcact gaatacacca tacactgggt tagacaggcc   120
cctggccaaa ggctggagtg gataggaggt attaatccta caatggtat tcctaactac   180
aaccagaagt tcaagggccg ggtcaccatc accgtagaca cctctgccag caccgcctac   240
atggaactgt ccagcctgcg ctccgaggac actgcagtct actactgcgc cagaagaaga   300
atcgcctatg gttacgacga gggccatgct atggactact ggggtcaagg aacccttgtc   360
accgtctcct ca                                                       372
```

<210> SEQ ID NO 12
<211> LENGTH: 124
<212> TYPE: PRT
<213> ORGANISM: Homo sapiens

<400> SEQUENCE: 12

```
Gln Val Gln Leu Val Gln Ser Gly Ala Glu Val Lys Lys Pro Gly Ala
  1               5                  10                  15
Ser Val Lys Val Ser Cys Lys Thr Ser Arg Tyr Thr Phe Thr Glu Tyr
             20                  25                  30
Thr Ile His Trp Val Arg Gln Ala Pro Gly Gln Arg Leu Glu Trp Ile
         35                  40                  45
Gly Gly Ile Asn Pro Asn Asn Gly Ile Pro Asn Tyr Asn Gln Lys Phe
     50                  55                  60
Lys Gly Arg Val Thr Ile Thr Val Asp Thr Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Arg Arg Ile Ala Tyr Gly Tyr Asp Glu Gly His Ala Met Asp
            100                 105                 110
```

Tyr Trp Gly Gln Gly Thr Leu Val Thr Val Ser Ser
        115                 120

<210> SEQ ID NO 13
<211> LENGTH: 372
<212> TYPE: DNA
<213> ORGANISM: Homo sapiens

<400> SEQUENCE: 13

```
caggtgcaac tagtgcagtc cggcgccgaa gtgaagaaac ccggtgcttc cgtgaaagtc      60
agctgtaaaa ctagtagata caccttcact gaatacacca tacactgggt tagacaggcc     120
cctggccaaa ggctggagtg gataggaggt attaatccta acaatggtat tcctaactac     180
aaccagaagt tcaagggccg ggtcaccatc accgtagaca cctctgccag caccgcctac     240
atggaactgt ccagcctgcg ctccgaggac actgcagtct acttctgcgc cagaagaaga     300
atcgcctatg gttacgacga gggccatgct atggactact ggggtcaagg aacccttgtc     360
accgtctcct ca                                                         372
```

<210> SEQ ID NO 14
<211> LENGTH: 124
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
  1               5                  10                  15

Ser Val Lys Val Ser Cys Lys Thr Ser Arg Tyr Thr Phe Thr Glu Tyr
             20                  25                  30

Thr Ile His Trp Val Arg Gln Ala Pro Gly Gln Arg Leu Glu Trp Ile
         35                  40                  45

Gly Gly Ile Asn Pro Asn Asn Gly Ile Pro Asn Tyr Asn Gln Lys Phe
     50                  55                  60

Lys Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Phe Cys
                 85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser
        115                 120

<210> SEQ ID NO 15
<211> LENGTH: 372
<212> TYPE: DNA
<213> ORGANISM: Homo sapiens

<400> SEQUENCE: 15

```
caggtgcaac tagtgcagtc cggcgccgaa gtgaagaaac ccggtgcttc cgtgaaagtc      60
agctgtaaaa ctagtggata caccttcact gaatacacca tacactgggt tagacaggcc     120
cctggccaaa ggctggagtg gataggaggt attaatccta acaatggtat tcctaactac     180
aaccagaagt tcaagggccg ggtcaccatc accgtagaca cctctgccag caccgcctac     240
atggaactgt ccagcctgcg ctccgaggac actgcagtct actactgcgc cagaagaaga     300
atcgcctatg gttacgacga gggccatgct atggactact ggggtcaagg aacccttgtc     360
accgtctcct ca                                                         372
```

```
<210> SEQ ID NO 16
<211> LENGTH: 124
<212> TYPE: PRT
<213> ORGANISM: Homo sapiens

<400> SEQUENCE: 16

Gln Val Gln Leu Val Gln Ser Gly Ala Glu Val Lys Lys Pro Gly Ala
 1               5                  10                  15

Ser Val Lys Val Ser Cys Lys Thr Ser Gly Tyr Thr Phe Thr Glu Tyr
                20                  25                  30

Thr Ile His Trp Val Arg Gln Ala Pro Gly Gln Arg Leu Glu Trp Ile
            35                  40                  45

Gly Gly Ile Asn Pro Asn Asn Gly Ile Pro Asn Tyr Asn Gln Lys Phe
        50                  55                  60

Lys Gly Arg Val Thr Ile Thr Val Asp Thr Ser Ala Ser Thr Ala Tyr
 65                  70                  75                  80

Met Glu Leu Ser Ser Leu Arg Ser Glu Asp Thr Ala Val Tyr Tyr Cys
                85                  90                  95

Ala Arg Arg Ile Ala Tyr Gly Tyr Asp Glu Gly His Ala Met Asp
                100                 105                 110

Tyr Trp Gly Gln Gly Thr Leu Val Thr Val Ser Ser
            115                 120

<210> SEQ ID NO 17
<211> LENGTH: 220
<212> TYPE: PRT
<213> ORGANISM: Homo sapiens

<400> SEQUENCE: 17

Asp Ile Val Met Ser Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
                20                  25                  30

Arg Asn Gln Lys Asn Tyr Leu Ala Trp Phe Gln Gln Lys Pro Gly Gln
            35                  40                  45

Ser Pro Lys Leu Leu Ile Phe Trp Ala Ser Thr Arg Glu Ser Gly Val
        50                  55                  60

Pro Asp Arg Phe Thr Gly Ser Gly Phe Gly Thr Asp Phe Asn Leu Thr
 65                  70                  75                  80

Ile Ser Ser Val Gln Ala Glu Asp Leu Ala Val Tyr Asp Cys Gln Gln
                85                  90                  95

Tyr Phe Ser Tyr Pro Leu Thr Phe Gly Ala Gly Thr Lys Leu Glu Leu
                100                 105                 110

Lys Arg Thr Val Ala Ala Pro Ser Val Phe Ile Phe Pro Pro Ser Asp
            115                 120                 125

Glu Gln Leu Lys Ser Gly Thr Ala Ser Val Val Cys Leu Leu Asn Asn
        130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
            195                 200                 205
```

Ser Pro Val Thr Lys Ser Phe Asn Arg Gly Glu Cys
    210                 215                 220

<210> SEQ ID NO 18
<211> LENGTH: 453
<212> TYPE: PRT
<213> ORGANISM: Homo sapiens

<400> SEQUENCE: 18

Val Gln Leu Gln Gln Ser Gly Pro Glu Leu Val Lys Pro Gly Ala Ser
  1               5                  10                  15

Val Lys Met Ser Cys Lys Thr Ser Arg Tyr Thr Phe Thr Glu Tyr Thr
             20                  25                  30

Ile His Trp Val Arg Gln Ser His Gly Lys Ser Leu Glu Trp Ile Gly
         35                  40                  45

Gly Ile Asn Pro Asn Asn Gly Ile Pro Asn Tyr Asn Gln Lys Phe Lys
 50                  55                  60

Gly Arg Ala Thr Leu Thr Val Gly Lys Ser Ser Thr Ala Tyr Met
 65                  70                  75                  80

Glu Leu Arg Ser Leu Thr Ser Glu Asp Ser Ala Val Tyr Phe Cys Ala
                 85                  90                  95

Arg Arg Arg Ile Ala Tyr Gly Tyr Asp Glu Gly His Ala Met Asp Tyr
            100                 105                 110

Trp Gly Gln Gly Thr Ser Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly Lys
    450

<210> SEQ ID NO 19
<211> LENGTH: 321
<212> TYPE: DNA
<213> ORGANISM: Homo sapiens

<400> SEQUENCE: 19
cgtactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                               321

<210> SEQ ID NO 20
<211> LENGTH: 107
<212> TYPE: PRT
<213> ORGANISM: Homo sapiens

<400> SEQUENCE: 20

Arg Thr Val Ala Ala Pro Ser Val Phe Ile Phe Pro Pro Ser Asp Glu
  1               5                  10                  15

Gln Leu Lys Ser Gly Thr Ala Ser Val Val Cys Leu Leu Asn Asn Phe
             20                  25                  30

Tyr Pro Arg Glu Ala Lys Val Gln Trp Lys Val Asp Asn Ala Leu Gln
         35                  40                  45

Ser Gly Asn Ser Gln Glu Ser Val Thr Glu Gln Asp Ser Lys Asp Ser
     50                  55                  60

Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 21
<211> LENGTH: 990
<212> TYPE: DNA
<213> ORGANISM: Homo sapiens

<400> SEQUENCE: 21
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
```

-continued

```
tggaactcag gcgccctgac cagcggcgtg cacaccttcc cggctgtcct acagtcctca    180
ggactctact ccctcagcag cgtggtgacc gtgccctcca gcagcttggg cacccagacc    240
tacatctgca acgtgaatca caagcccagc aacaccaagg tggacaagaa agttgagccc    300
aaatcttgtg acaaaactca cacatgccca ccgtgcccag cacctgaact cctgggggga    360
ccgtcagtct tcctcttccc cccaaaaccc aaggacaccc tcatgatctc ccggacccct    420
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gggtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag gcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

<210> SEQ ID NO 22
<211> LENGTH: 330
<212> TYPE: PRT
<213> ORGANISM: Homo sapiens

<400> SEQUENCE: 22

```
Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
```

```
             210                 215                 220
Gln Pro Arg Glu Pro Gln Val Tyr Thr Leu Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 23
<211> LENGTH: 427
<212> TYPE: DNA
<213> ORGANISM: Homo sapiens

<400> SEQUENCE: 23
aagcttgccg ccaccatgga ttcacaggcc caggttctta tgttactgcc gctatgggta      60
tctggtacct gtggggacat tgtgatgtca cagtctccat cctccctagc tgtgtcagtt     120
ggagagaagg ttactatgag ctgcaagtcc agtcagagcc ttttatatag tcgtaatcaa     180
aagaactact ggcctggtt ccagcagaag ccagggcagt ctcctaaaact gctgattttc     240 tgggcatcca ctagggaatc tggggtccct gatcgcttca caggcagtgg atttgggacg     300
gatttcaatc tcaccatcag cagtgtgcag gctgaggacc tggcagttta tgactgtcag     360
caatatttta gctatccgct cacgttcggt gctgggacca agctggagct gaaacgtgag     420
tggatcc                                                              427

<210> SEQ ID NO 24
<211> LENGTH: 133
<212> TYPE: PRT
<213> ORGANISM: Homo sapiens

<400> SEQUENCE: 24

Met Asp Ser Gln Ala Gln Val Leu Met Leu Leu Pro Leu Trp Val Ser
  1               5                  10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Arg Asn Gln Lys Asn Tyr Leu Ala Trp Phe Gln Gln
        50                  55                  60

Lys Pro Gly Gln Ser Pro Lys Leu Leu Ile Phe Trp Ala Ser Thr Arg
 65                  70                  75                  80

Glu Ser Gly Val Pro Asp Arg Phe Thr Gly Ser Gly Phe Gly Thr Asp
                 85                  90                  95

Phe Asn Leu Thr Ile Ser Ser Val Gln Ala Glu Asp Leu Ala Val Tyr
                100                 105                 110

Asp Cys Gln Gln Tyr Phe Ser Tyr Pro Leu Thr Phe Gly Ala Gly Thr
            115                 120                 125
```

```
<210> SEQ ID NO 25
<211> LENGTH: 457
<212> TYPE: DNA
<213> ORGANISM: Homo sapiens

<400> SEQUENCE: 25
aagcttgccg ccaccatggg atggagctgg gtctttctct ttctcctgtc aggaactgca      60
ggtgtcctct ctgaggtcca gctgcaacag tctggacctg agctggtgaa gcctggggct     120
tcagtaaaga tgtcctgcaa gacttctaga tacacattca ctgaatacac catacactgg     180
gtgagacaga gccatggaaa gagccttgag tggattggag gtattaatcc taacaatggt     240
attcctaact acaaccagaa gttcaagggc agggccacat tgactgtagg caagtcctcc     300
agcaccgcct acatggagct ccgcagcctg acatctgagg attctgcggt ctatttctgt     360
gcaagaagaa gaatcgccta tggttacgac gagggccatg ctatggacta ctggggtcaa     420
ggaacctcag tcaccgtctc ctcaggtgag tggatcc                              457

<210> SEQ ID NO 26
<211> LENGTH: 143
<212> TYPE: PRT
<213> ORGANISM: Homo sapiens

<400> SEQUENCE: 26

Met Gly Trp Ser Trp Val Phe Leu Phe Leu Leu Ser Gly Thr Ala Gly
  1               5                  10                  15
Val Leu Ser Glu Val Gln Leu Gln Gln Ser Gly Pro Glu Leu Val Lys
             20                  25                  30
Pro Gly Ala Ser Val Lys Met Ser Cys Lys Thr Ser Arg Tyr Thr Phe
         35                  40                  45
Thr Glu Tyr Thr Ile His Trp Val Arg Gln Ser His Gly Lys Ser Leu
     50                  55                  60
Glu Trp Ile Gly Gly Ile Asn Pro Asn Asn Gly Ile Pro Asn Tyr Asn
 65                  70                  75                  80
Gln Lys Phe Lys Gly Arg Ala Thr Leu Thr Val Gly Lys Ser Ser
                 85                  90                  95
Thr Ala Tyr Met Glu Leu Arg Ser Leu Thr Ser Glu Asp Ser Ala Val
            100                 105                 110
Tyr Phe Cys Ala Arg Arg Arg Ile Ala Tyr Gly Tyr Asp Glu Gly His
        115                 120                 125
Ala Met Asp Tyr Trp Gly Gln Gly Thr Ser Val Thr Val Ser Ser
    130                 135                 140

<210> SEQ ID NO 27
<211> LENGTH: 8068
<212> TYPE: DNA
<213> ORGANISM: Homo sapiens

<400> SEQUENCE: 27
gaattccagc acactggcgg ccgttactag ttattaatag taatcaatta cggggtcatt      60
agttcatagc ccatatatgg agttccgcgt tacataactt acggtaaatg gcccgcctgg     120
ctgaccgccc aacgaccccc gcccattgac gtcaataatg acgtatgttc ccatagtaac     180
gccaataggg actttccatt gacgtcaatg ggtggagtat ttacgtaaa ctgcccactt      240
ggcagtacat caagtgtatc atatgccaag tacgccccct attgacgtca atgacggtaa     300
```

Lys Leu Glu Leu Lys
    130

```
atggcccgcc tggcattatg cccagtacat gaccttatgg gactttccta cttggcagta    360
catctacgta ttagtcatcg ctattaccat ggtgatgcgg ttttggcagt acatcaatgg    420
gcgtggatag cggtttgact cacggggatt ccaagtctc cacccattg acgtcaatgg      480 gagtttgttt tggcaccaaa atcaacggga ctttccaaaa tgtcgtaaca actccgcccc    540
attgacgcaa atgggcggta ggcgtgtacg gtgggaggtc tatataagca gagctcgttt    600
agtgaaccgt cagatcgcct ggagacgcca tccacgctgt tttgacctcc atagaagaca    660
ccgggaccga tccagcctcc gcggccggga acggtgcatt ggaacgcgga ttccccgtgc    720
caagagtgac gtaagtaccg cctatagagt ctataggccc accccttgg cttcttatgc     780 atgctatact gttttggct tggggtctat acaccccgc ttcctcatgt tataggtgat      840
ggtatagctt agcctatagg tgtgggttat tgaccattat tgaccactcc cctattggtg    900
acgatacttt ccattactaa tccataacat ggctctttgc cacaactctc tttattggct    960
atatgccaat acactgtcct tcagagactg acacggactc tgtattttta caggatgggg   1020
tctcatttat tatttacaaa ttcacatata caacaccacc gtccccagtg cccgcagttt   1080
ttattaaaca taacgtggga tctccacgcg aatctcgggt acgtgttccg gacatgggct   1140
cttctccggt agcggcggag cttctacatc cgagccctgc tcccatgcct ccagcgactc   1200
atggtcgctc ggcagctcct tgctcctaac agtggaggcc agacttaggc acagcacgat   1260
gcccaccacc accagtgtgc cgcacaaggc cgtggcggta gggtatgtgt ctgaaaatga   1320
gctcggggag cgggcttgca ccgctgacgc atttggaaga cttaaggcag cggcagaaga   1380
agatgcaggc agctgagttg ttgtgttctg ataagagtca gaggtaactc ccgttgcggt   1440
gctgttaacg gtggagggca gtgtagtctg agcagtactc gttgctgccg cgcgcgccac   1500
cagacataat agctgacaga ctaacagact gttccttttcc atgggtcttt tctgcagtca   1560
ccgtccttga cacgcgtctc gggaagcttg ccgccaccat ggattcacag gcccaggttc   1620
ttatgttact gccgctatgg gtatctggta cctgtgggga cattgtgatg tcacagtctc   1680
catcctccct agctgtgtca gttggagaga aggttactat gagctgcaag tccagtcaga   1740
gccttttata ttctagaaat caaaagaact acttggcctg gttccagcag aagccagggc   1800
agtctcctaa actgctgatt ttctgggcat ccactaggga atctggggtc cctgatcgct   1860
tcacaggcag tggatttggg acggatttca atctcaccat cagcagtgtg caggctgagg   1920
acctggcagt ttatgactgt cagcaatatt ttagctatcc gctcacgttc ggtgctggga   1980
ccaagctgga gctgaaacgt gagtggatcc atctgggata agcatgctgt tttctgtctg   2040
tccctaacat gccctgtgat tatgcgcaaa caacacaccc aagggcagaa ctttgttact   2100
taaacaccat cctgtttgct tctttcctca ggaactgtgg ctgcaccatc tgtcttcatc   2160
ttcccgccat ctgatgagca gttgaaatct ggaactgcct ctgttgtgtg cctgctgaat   2220
aacttctatc ccagagaggc caaagtacag tggaaggtgg ataacgccct ccaatcgggt   2280
aactcccagg agagtgtcac agagcaggac agcaaggaca gcacctacag cctcagcagc   2340
accctgacgc tgagcaaagc agactacgag aaacacaaag tctacgcctg cgaagtcacc   2400
catcagggcc tgagctcgcc cgtcacaaag agcttcaaca gggagagtg ttagagggag    2460 aagtgccccc acctgctcct cagttccagc ctgaccccct cccatccttt ggcctctgac   2520
cctttttcca caggggacct accccctattg cggtcctcca gctcatcttt cacctcaccc   2580
ccctcctcct ccttggcttt aattatgcta atgttggagg agaatgaata aataaagtga   2640
```

```
atctttgcac ctgtggtgga tctaataaaa gatatttatt ttcattagat atgtgtgttg   2700
gttttttgtg tgcagtgcct ctatctggag gccaggtagg gctggccttg ggggagggg    2760 aggccagaat gactccaaga gctacaggaa ggcaggtcag agaccccact ggacaaacag   2820
tggctggact ctgcaccata acacacaatc aacagggag tgagctggaa atttgctagc    2880
gaattcttga agacgaaagg gcctcgtgat acgcctattt ttataggtta atgtcatgat   2940
aataatggtt tcttagacgt caggtggcac ttttcgggga atgtgcgcg gaacccctat    3000 ttgtttattt ttctaaatac attcaaatat gtatccgctc atgagacaat aaccctgata   3060
aatgcttcaa taatattgaa aaaggaagag tatgagtatt caacatttcc gtgtcgccct   3120
tattcccttt tttgcggcat tttgccttcc tgttttgct cacccagaaa cgctggtgaa     3180
agtaaaagat gctgaagatc agttgggtgc acgagtgggt tacatcgaac tggatctcaa   3240
cagcggtaag atccttgaga gttttcgccc cgaagaacgt tttccaatga tgagcacttt   3300
taaagttctg ctatgtggcg cggtattatc ccgtgttgac gccgggcaag agcaactcgg   3360
tcgccgcata cactattctc agaatgactt ggttgagtac tcaccagtca cagaaaagca   3420
tcttacggat ggcatgacag taagagaatt atgcagtgct gccataacca tgagtgataa   3480
cactgcggcc aacttacttc tgacaacgat cggaggaccg aaggagctaa ccgcttttt    3540 gcacaacatg gggatcatg taactcgcct tgatcgttgg gaaccggagc tgaatgaagc    3600
cataccaaac gacgagcgtg acaccacgat gcctgcagca atggcaacaa cgttgcgcaa   3660
actattaact ggcgaactac ttactctagc ttcccgcaa caattaatag actggatgga   3720
ggcggataaa gttgcaggac cacttctgcg ctcggccctt ccggctggct ggtttattgc   3780
tgataaatct ggagccggtg agcgtgggtc tcgcggtatc attgcagcac tggggccaga   3840
tggtaagccc tcccgtatcg tagttatcta cacgacgggg agtcaggcaa ctatggatga   3900
acgaaataga cagatcgctg agataggtgc ctcactgatt aagcattggt aactgtcaga   3960
ccaagtttac tcatatatac tttagattga tttaaaactt cattttaat ttaaaaggat    4020 ctaggtgaag atcctttttg ataatctcat gaccaaaatc ccttaacgtg agttttcgtt   4080
ccactgagcg tcagaccccg tagaaaagat caaaggatct tcttgagatc ctttttttct   4140
gcgcgtaatc tgctgcttgc aaacaaaaaa accaccgcta ccagcggtgg tttgtttgcc   4200
ggatcaagag ctaccaactc tttttccgaa ggtaactggc ttcagcagag cgcagatacc   4260
aaatactgtc cttctagtgt agccgtagtt aggccaccac ttcaagaact ctgtagcacc   4320
gcctacatac ctcgctctgc taatcctgtt accagtggct gctgccagtg gcgataagtc   4380
gtgtcttacc gggttggact caagacgata gttaccggat aaggcgcagc ggtcgggctg   4440
aacggggggt tcgtgcacac agcccagctt ggagcgaacg acctacaccg aactgagata   4500
cctacagcgt gagctatgag aaagcgccac gcttcccgaa gggagaaagg cggacaggta   4560
tccggtaagc ggcagggtcg gaacaggaga gcgcacgagg gagcttccag ggggaaacgc   4620
ctggtatctt tatagtcctg tcgggtttcg ccacctctga cttgagcgtc gatttttgtg   4680
atgctcgtca ggggggcgga gcctatggaa aaacgccagc aacgcggcct ttttacggtt   4740
cctggccttt tgctggcctt tgctcacat gttctttcct gcgttatccc ctgattctgt     4800
ggataaccgt attaccgcct tgagtgagc tgataccgct cgccgcagcc gaacgaccga    4860
gcgcagcgag tcagtgagcg aggaagcgga agagcgcctg atgcggtatt ttctccttac   4920
gcatctgtgc ggtatttcac accgcatatg gtgcactctc agtacaatct gctctgatgc   4980
cgcatagtta agccagtata cactccgcta tcgctacgtg actgggtcat ggctgcgccc   5040
```

```
cgacacccgc aacacccgc tgacgcgccc tgacgggctt gtctgctccc ggcatccgct      5100
tacagacaag ctgtgaccgt ctccgggagc tgcatgtgtc agaggttttc accgtcatca      5160
ccgaaacgcg cgaggcagct gtggaatgtg tgtcagttag ggtgtggaaa gtccccaggc      5220
tccccagcag gcagaagtat gcaaagcatg catctcaatt agtcagcaac caggctcccc      5280
agcaggcaga agtatgcaaa gcatgcatct caattagtca gcaaccatag tcccgcccct      5340
aactccgccc atcccgcccc taactccgcc cagttccgcc cattctccgc cccatggctg      5400
actaattttt tttatttatg cagaggccga ggccgcctcg gcctctgagc tattccagaa      5460
gtagtgagga ggcttttttg gaggcctagg cttttgcaaa aagctagctt cacgctgccg      5520
caagcactca gggcgcaagg gctgctaaag gaagcggaac acgtagaaag ccagtccgca      5580
gaaacggtgc tgaccccgga tgaatgtcag ctactgggct atctggacaa gggaaaacgc      5640
aagcgcaaag agaaagcagg tagcttgcag tgggcttaca tggcgatagc tagactgggc      5700
ggttttatgg acagcaagcg aaccggaatt gccagctggg gcgccctctg gtaaggttgg      5760
gaagccctgc aaagtaaact ggatggcttt cttgccgcca aggatctgat ggcgcagggg      5820
atcaagatct gatcaagaga caggatgagg atcgtttcgc atgattgaac aagatggatt      5880
gcacgcaggt tctccggccg cttgggtgga gaggctattc ggctatgact gggcacaaca      5940
gacaatcggc tgctctgatg ccgccgtgtt ccggctgtca gcgcaggggc gcccggttct      6000
ttttgtcaag accgacctgt ccggtgccct gaatgaactg caggacgagg cagcgcggct      6060
atcgtggctg gccacgacgg gcgttccttg cgcagctgtg ctcgacgttg tcactgaagc      6120
gggaagggac tggctgctat tgggcgaagt gccggggcag gatctcctgt catctcacct      6180
tgctcctgcc gagaaagtat ccatcatggc tgatgcaatg cggcggctgc atacgcttga      6240
tccggctacc tgcccattcg accaccaagc gaaacatcgc atcgagcgag cacgtactcg      6300
gatggaagcc ggtcttgtcg atcaggatga tctggacgaa gagcatcagg ggctcgcgcc      6360
agccgaactg ttcgccaggc tcaaggcgcg catgcccgac ggcgaggatc tcgtcgtgac      6420
ccatggcgat gcctgcttgc cgaatatcat ggtggaaaat ggccgctttt ctggattcat      6480
cgactgtggc cggctgggtg tggcggaccg ctatcaggac atagcgttgg ctacccgtga      6540
tattgctgaa gagcttggcg gcgaatgggc tgaccgcttc ctcgtgcttt acggtatcgc      6600
cgctcccgat tcgcagcgca tcgccttcta tcgccttctt gacgagttct tctgagcggg      6660 actctgggt tcgaaatgac cgaccaagcg acgcccaacc tgccatcacg agatttcgat      6720
tccaccgccg ccttctatga aaggttgggc ttcggaatcg ttttccggga cgccggctgg      6780
atgatcctcc agcgcgggga tctcatgctg gagttcttcg cccacccccgg gctcgatccc      6840 ctcgcgagtt ggttcagctg ctgcctgagg ctggacgacc tcgcggagtt ctaccggcag      6900
tgcaaatccg tcggcatcca ggaaaccagc agcggctatc cgcgcatcca tgcccccgaa      6960
ctgcaggagt ggggaggcac gatggccgct ttggtcccgg atctttgtga aggaacctta      7020
cttctgtggt gtgacataat tggacaaact acctacagag atttaaagct ctaaggtaaa      7080
tataaaattt ttaagtgtat aatgtgttaa actactgatt ctaattgttt gtgtatttta      7140
gattccaacc tatggaactg atgaatggga gcagtggtgg aatgccttta atgaggaaaa      7200
cctgttttgc tcagaagaaa tgccatctag tgatgatgag gctactgctg actctcaaca      7260
ttctactcct ccaaaaaaga agagaaaggt agaagacccc aaggactttc cttcagaatt      7320
gctaagtttt ttgagtcatg ctgtgtttag taatagaact cttgcttgct ttgctatttta     7380
```

-continued

```
caccacaaag gaaaaagctg cactgctata caagaaaatt atggaaaaat attctgtaac    7440
ctttataagt aggcataaca gttataatca taacatactg ttttttctta ctccacacag    7500
gcatagagtg tctgctatta ataactatgc tcaaaaattg tgtaccttta gcttttaat     7560 ttgtaaaggg gttaataagg aatatttgat gtatagtgcc ttgactagag atcataatca    7620
gccataccac atttgtagag gttttacttg cttttaaaaaa cctcccacac ctcccctga    7680 acctgaaaca taaaatgaat gcaattgttg ttgttaactt gtttattgca gcttataatg    7740
gttacaaata aagcaatagc atcacaaatt tcacaaataa agcatttttt tcactgcatt    7800
ctagttgtgg tttgtccaaa ctcatcaatg tatcttatca tgtctggatc taataaaaga    7860
tatttatttt cattagatat gtgtgttggt ttttgtgtg cagtgcctct atctggaggc     7920
caggtagggc tggccttggg ggaggggag gccagaatga ctccaagagc tacaggaagg    7980
caggtcagag accccactgg acaaacagtg gctggactct gcaccataac acacaatcaa    8040 cagggagtg agctggaaat ttgctagc                                        8068
```

<210> SEQ ID NO 28
<211> LENGTH: 240
<212> TYPE: PRT
<213> ORGANISM: Homo sapiens

<400> SEQUENCE: 28

```
Met Asp Ser Gln Ala Gln Val Leu Met Leu Leu Pro Leu Trp Val Ser
 1               5                  10                  15

Gly Thr Cys Gly Asp Ile Val Met Ser Gln Ser Pro Ser Ser Leu Ala
                20                  25                  30

Val Ser Val Gly Glu Lys Val Thr Met Ser Cys Lys Ser Ser Gln Ser
            35                  40                  45

Leu Leu Tyr Ser Arg Asn Gln Lys Asn Tyr Leu Ala Trp Phe Gln Gln
        50                  55                  60

Lys Pro Gly Gln Ser Pro Lys Leu Leu Ile Phe Trp Ala Ser Thr Arg
 65                  70                  75                  80

Glu Ser Gly Val Pro Asp Arg Phe Thr Gly Ser Gly Phe Gly Thr Asp
                85                  90                  95

Phe Asn Leu Thr Ile Ser Ser Val Gln Ala Glu Asp Leu Ala Val Tyr
            100                 105                 110

Asp Cys Gln Gln Tyr Phe Ser Tyr Pro Leu Thr Phe Gly Ala Gly Thr
        115                 120                 125

Lys Leu Glu Leu Lys Arg Thr Val Ala Ala Pro Ser Val Phe Ile Phe
130                 135                 140

Pro Pro Ser Asp Glu Gln Leu Lys Ser Gly Thr Ala Ser Val Val Cys
145                 150                 155                 160

Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 29

```
<211> LENGTH: 7731
<212> TYPE: DNA
<213> ORGANISM: Homo sapiens

<400> SEQUENCE: 29
ttgaagacga aagggcctcg tgatacgcct atttttatag gttaatgtca tgataataat      60
ggtttcttag acgtcaggtg gcacttttcg gggaaatgtg cgcggaaccc ctatttgttt     120
atttttctaa atacattcaa atatgtatcc gctcatgaga caataaccct gataaatgct     180
tcaataatat tgaaaaagga agagtatgag tattcaacat ttccgtgtcg cccttattcc     240
cttttttgcg gcattttgcc ttcctgtttt tgctcaccca gaaacgctgg tgaaagtaaa     300
agatgctgaa gatcagttgg gtgcacgagt gggttacatc gaactggatc tcaacagcgg     360
taagatcctt gagagttttc gccccgaaga acgttttcca atgatgagca cttttaaagt     420
tctgctatgt ggcgcggtat tatcccgtgt tgacgccggg caagagcaac tcggtcgccg     480
catacactat tctcagaatg acttggttga gtactcacca gtcacagaaa agcatcttac     540
ggatggcatg acagtaagag aattatgcag tgctgccata accatgagtg ataacactgc     600
ggccaactta cttctgacaa cgatcggagg accgaaggag ctaaccgctt ttttgcacaa     660
catgggggat catgtaactc gccttgatcg ttgggaaccg gagctgaatg aagccatacc     720
aaacgacgag cgtgacacca cgatgcctgc agcaatggca acaacgttgc gcaaactatt     780
aactggcgaa ctacttactc tagcttcccg gcaacaatta atagactgga tggaggcgga     840
taaagttgca ggaccacttc tgcgctcggc ccttccggct ggctggttta ttgctgataa     900
atctggagcc ggtgagcgtg ggtctcgcgg tatcattgca gcactggggc cagatggtaa     960
gccctcccgt atcgtagtta tctacacgac ggggagtcag gcaactatgg atgaacgaaa    1020
tagacagatc gctgagatag gtgcctcact gattaagcat tggtaactgt cagaccaagt    1080
ttactcatat atactttaga ttgatttaaa acttcatttt taatttaaaa ggatctaggt    1140
gaagatcctt tttgataatc tcatgaccaa atcccttaa cgtgagtttt cgttccactg    1200
agcgtcagac cccgtagaaa agatcaaagg atccttttga tcctttttt ttctgcgcgt    1260
aatctgctgc ttgcaaacaa aaaaaccacc gctaccagcg tggtttgtt tgccggatca    1320
agagctacca actctttttc cgaaggtaac tggcttcagc agagcgcaga taccaaatac    1380
tgtccttcta gtgtagccgt agttaggcca ccacttcaag aactctgtag caccgcctac    1440
atacctcgct ctgctaatcc tgttaccagt ggctgctgcc agtggcgata gtcgtgtct     1500
taccggggttg gactcaagac gatagttacc ggataaggcg cagcggtcgg gctgaacggg    1560
gggttcgtgc acacagccca gcttggagcg aacgacctac accgaactga gatacctaca    1620
gcgtgagcta tgagaaagcg ccacgcttcc cgaagggaga aaggcggaca ggtatccggt    1680
aagcggcagg gtcggaacag gagagcgcac gagggagctt ccagggggaa acgcctggta    1740
tctttatagt cctgtcgggt ttcgccacct ctgacttgag cgtcgatttt tgtgatgctc    1800
gtcaggggggg cggagcctat ggaaaaacgc cagcaacgcg ccttttttac ggttcctggc    1860
cttttgctgg ccttttgctc acatgttctt tcctgcgtta tcccctgatt ctgtggataa    1920
ccgtattacc gcctttgagt gagctgatac cgctcgccgc agccgaacga ccgagcgcag    1980
cgagtcagtg agcgaggaag cggaagagcg cctgatgcgg tattttctcc ttacgcatct    2040
gtgcggtatt tcacaccgca tatggtgcac tctcagtaca atctgctctg atgccgcata    2100
gttaagccag tatacactcc gctatcgcta cgtgactggg tcatggctgc gccccgacac    2160
ccgccaacac ccgctgacgc gccctgacgg gcttgtctgc tcccggcatc cgcttacaga    2220
```

```
caagctgtga ccgtctccgg gagctgcatg tgtcagaggt tttcaccgtc atcaccgaaa    2280
cgcgcgaggc agcatgcatc tcaattagtc agcaaccata gtcccgcccc taactccgcc    2340
catcccgccc ctaactccgc ccagttccgc ccattctccg ccccatggct gactaatttt    2400
ttttatttat gcagaggccg aggccgcctc ggcctctgag ctattccaga gtagtgagg     2460 aggctttttt ggaggcctag cttttgcaa aaagctagct tacagctcag ggctgcgatt    2520
tcgcgccaaa cttgacggca atcctagcgt gaaggctggt aggattttat ccccgctgcc   2580
atcatggttc gaccattgaa ctgcatcgtc gccgtgtccc aaaatatggg gattggcaag   2640
aacggagacc taccctggcc tccgctcagg aacgagttca gtacttcca aagaatgacc    2700 acaacctctt cagtggaagg taaacagaat ctggtgatta tgggtaggaa aacctggttc   2760
tccattcctg agaagaatcg accttttaaag gacagaatta atatagttct cagtagagaa  2820
ctcaaagaac caccacgagg agctcatttt cttgccaaaa gtttggatga tgccttaaga   2880
cttattgaac aaccggaatt ggcaagtaaa gtagacatgg tttggatagt cggaggcagt   2940
tctgtttacc aggaagccat gaatcaacca ggccacctca gactctttgt gacaaggatc   3000
atgcaggaat ttgaaagtga cacgtttttc ccagaaattg atttggggaa atataaactt   3060
ctcccagaat acccaggcgt cctctctgag gtccaggagg aaaaaggcat caagtataag   3120
tttgaagtct acgagaagaa agactaacag gaagatgctt tcaagttctc tgctcccctc   3180
ctaaagctat gcatttttat aagaccatgg gacttttgct ggctttagat ctttgtgaag   3240
gaaccttact tctgtggtgt gacataattg gacaaactac ctacagagat ttaaagctct   3300
aaggtaaata taaattttt aagtgtataa tgtgttaaac tactgattct aattgtttgt    3360
gtattttaga ttccaaccta tggaactgat gaatgggagc agtggtggaa tgcctttaat   3420
gaggaaaacc tgttttgctc agaagaaatg ccatctagtg atgatgaggc tactgctgac   3480
tctcaacatt ctactcctcc aaaaaagaag agaaaggtag aagacccaa ggactttcct    3540 tcagaattgc taagttttttt gagtcatgct gtgtttagta atagaactct tgcttgcttt   3600
gctatttaca ccacaaagga aaaagctgca ctgctataca agaaaattat ggaaaaatat   3660
tctgtaaccT ttataagtag gcataacagt tataatcata atactgtt ttttcttact     3720 ccacacaggc atagagtgtc tgctattaat aactatgctc aaaaattgtg tacctttagc   3780
ttttaatttt gtaaagggt taataaggaa tatttgatgt atagtgcctt gactagagat    3840
cataatcagc cataccacat ttgtagaggt tttacttgct ttaaaaaacc tcccacacct   3900
ccccctgaac ctgaaacata aaatgaatgc aattgttgtt gttaacttgt ttattgcagc   3960
ttataatggt tacaaataaa gcaatagcat cacaaatttc acaaataaag cattttttc    4020 actgcattct agttgtggtt tgtccaaact catcaatgta tcttatcatg tctggatcta   4080 ataaagata tttattttca ttagatatgt gtgttggttt tttgtgtgca gtgcctctat    4140
ctggaggcca ggtagggctg gccttggggg aggggaggc cagaatgact ccaagagcta    4200
caggaaggca ggtcagagac cccactggac aaacagtggc tggactctgc accataacac   4260
acaatcaaca ggggagtgag ctggaaattt gctagcgaat tccagcacac tggcggccgt   4320
tactagttat taatagtaat caattacggg gtcattagtt catagcccat atatggagtt   4380
ccgcgttaca aacttacgg taaatggccc gcctggctga ccgcccaacg acccccgccc    4440
attgacgtca ataatgacgt atgttcccat agtaacgcca atagggactt ccattgacg   4500 tcaatgggtg gagtatttac ggtaaactgc ccacttggca gtacatcaag tgtatcatat   4560
```

-continued

```
gccaagtacg cccctattg acgtcaatga cggtaaatgg cccgcctggc attatgccca    4620
gtacatgacc ttatgggact ttcctacttg gcagtacatc tacgtattag tcatcgctat    4680
taccatggtg atgcggtttt ggcagtacat caatgggcgt ggatagcggt ttgactcacg    4740
gggatttcca agtctccacc ccattgacgt caatgggagt ttgttttggc accaaaatca    4800
acgggacttt ccaaaatgtc gtaacaactc cgccccattg acgcaaatgg gcggtaggcg    4860
tgtacggtgg gaggtctata taagcagagc tcgtttagtg aaccgtcaga tcgcctggag    4920
acgccatcca cgctgttttg acctccatag aagacaccgg gaccgatcca gcctccgcgg    4980
ccgggaacgg tgcattggaa cgcggattcc ccgtgccaag agtgacgtaa gtaccgccta    5040
tagagtctat aggcccaccc ccttggcttc ttatgcatgc tatactgttt ttggcttggg    5100
gtctatacac ccccgcttcc tcatgttata ggtgatggta tagcttagcc tataggtgtg    5160
ggttattgac cattattgac cactcccta ttggtgacga tactttccat tactaatcca    5220
taacatggct ctttgccaca actctcttta ttggctatat gccaatacac tgtccttcag    5280
agactgacac ggactctgta ttttacagg atggggtctc atttattatt tacaaattca    5340
catatacaac accaccgtcc ccagtgcccg cagttttat taaacataac gtgggatctc    5400
cacgcgaatc tcgggtacgt gttccggaca tgggctcttc tccggtagcg gcggagcttc    5460
tacatccgag ccctgctccc atgcctccag cgactcatgg tcgctcggca gctccttgct    5520
cctaacagtg gaggccagac ttaggcacag cacgatgccc accaccacca gtgtgccgca    5580
caaggccgtg gcggtagggt atgtgtctga aaatgagctc ggggagcggg cttgcaccgc    5640
tgacgcattt ggaagactta aggcagcggc agaagaagat gcaggcagct gagttgttgt    5700
gttctgataa gagtcagagg taactcccgt tgcggtgctg ttaacggtgg agggcagtgt    5760
agtctgagca gtactcgttg ctgccgcgcg cgccaccaga cataatagct gacagactaa    5820
cagactgttc cttccatgg gtcttttctg cagtcaccgt ccttgacacg cgtctcggga    5880
agcttgccgc caccatggga tggagctggg tctttctctt tctcctgtca ggaactgcag    5940
gtgtcctctc tgaggtccag ctgcaacagt ctggacctga gctggtgaag cctggggctt    6000
cagtaaagat gtcctgcaag acttctagat acacattcac tgaatacacc atacactggg    6060
tgagacagag ccatggaaag agccttgagt ggattggagg tattaatcct aacaatggta    6120
ttcctaacta caaccagaag ttcaagggca gggccacatt gactgtaggc aagtcctcca    6180
gcaccgccta catggagctc cgcagcctga catctgagga ttctgcggtc tatttctgtg    6240
caagaagaag aatcgcctat ggttacgacg agggccatgc tatggactac tggggtcaag    6300
gaacctcagt caccgtctcc tcaggtgagt ggatcctctg cgcctgggcc cagctctgtc    6360
ccacaccgcg gtcacatggc accacctctc ttgcagcctc caccaagggc ccatcggtct    6420
tccccctggc accctcctcc aagagcacct ctggggcac agcggccctg ggctgcctgg    6480
tcaaggacta cttccccgaa ccggtgacgg tgtcgtggaa ctcaggcgcc ctgaccagcg    6540
gcgtgcacac cttcccggct gtcctacagt cctcaggact ctactccctc agcagcgtgg    6600
tgaccgtgcc ctccagcagc ttgggcaccc agacctacat ctgcaacgtg aatcacaagc    6660
ccagcaacac caaggtggac aagaaagttg agcccaaatc ttgtgacaaa actcacacat    6720
gcccaccgtg cccagcacct gaactcctgg ggggaccgtc agtcttcctc ttccccccaa    6780
aacccaagga caccctcatg atctcccgga ccctgaggt cacatgcgtg gtggtggacg    6840
tgagccacga agaccctgag gtcaagttca actggtacgt ggacggcgtg gaggtgcata    6900
atgccaagac aaagccgcgg gaggagcagt acaacagcac gtaccgggtg gtcagcgtcc    6960
```

```
tcaccgtcct gcaccaggac tggctgaatg gcaaggagta caagtgcaag gtctccaaca    7020
aagccctccc agcccccatc gagaaaacca tctccaaagc caagggcag ccccgagaac    7080 cacaggtgta caccctgccc ccatcccggg aggagatgac caagaaccag gtcagcctga    7140
cctgcctggt caaaggcttc tatcccagcg acatcgccgt ggagtgggag agcaatgggc    7200
agccggagaa caactacaag accacgcctc ccgtgctgga ctccgacggc tccttcttcc    7260
tctacagcaa gctcaccgtg gacaagagca ggtggcagca ggggaacgtc ttctcatgct    7320
ccgtgatgca tgaggctctg cacaaccact acacgcagaa gagcctctcc ctgtctccgg    7380
gtaaatgagt gcgacggccg gcaagcccg ctccccgggc tctcgcggtc gcacgaggat    7440
gcttggcacg taccccctgt acatacttcc cgggcgccca gcatggaaat aaagcaccgg    7500
atctaataaa agatatttat tttcattaga tatgtgtgtt ggttttttgt gtgcagtgcc    7560
tctatctgga ggccaggtag ggctggcctt gggggagggg gaggccagaa tgactccaag    7620
agctacagga aggcaggtca gagaccccac tggacaaaca gtggctggac tctgcaccat    7680
aacacacaat caacagggga gtgagctgga aatttgctag cgaattaatt c             7731
```

<210> SEQ ID NO 30
<211> LENGTH: 472
<212> TYPE: PRT
<213> ORGANISM: Homo sapiens

<400> SEQUENCE: 30

```
Met Gly Trp Ser Trp Val Phe Leu Phe Leu Leu Ser Gly Thr Ala Gly
 1               5                  10                  15

Val Leu Ser Glu Val Gln Leu Gln Gln Ser Gly Pro Glu Leu Val Lys
            20                  25                  30

Pro Gly Ala Ser Val Lys Met Ser Cys Lys Thr Ser Arg Tyr Thr Phe
        35                  40                  45

Thr Glu Tyr Thr Ile His Trp Val Arg Gln Ser His Gly Lys Ser Leu
    50                  55                  60

Glu Trp Ile Gly Gly Ile Asn Pro Asn Asn Gly Ile Pro Asn Tyr Asn
65                  70                  75                  80

Gln Lys Phe Lys Gly Arg Ala Thr Leu Thr Val Gly Lys Ser Ser Ser
                85                  90                  95

Thr Ala Tyr Met Glu Leu Arg Ser Leu Thr Ser Glu Asp Ser Ala Val
            100                 105                 110

Tyr Phe Cys Ala Arg Arg Ile Ala Tyr Gly Tyr Asp Glu Gly His
        115                 120                 125

Ala Met Asp Tyr Trp Gly Gln Gly Thr Ser Val Thr Val Ser Ser Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
            180                 185                 190

His Thr Phe Pro Ala Val Leu Gln Ser Ser Gly Leu Tyr Ser Leu Ser
        195                 200                 205

Ser Val Val Thr Val Pro Ser Ser Ser Leu Gly Thr Gln Thr Tyr Ile
    210                 215                 220

Cys Asn Val Asn His Lys Pro Ser Asn Thr Lys Val Asp Lys Lys Val
225                 230                 235                 240
```

```
Glu Pro Lys Ser Cys Asp Lys Thr His Thr Cys Pro Pro Cys Pro Ala
                245                 250                 255

Pro Glu Leu Leu Gly Gly Pro Ser Val Phe Leu Phe Pro Pro Lys Pro
            260                 265                 270

Lys Asp Thr Leu Met Ile Ser Arg Thr Pro Glu Val Thr Cys Val Val
        275                 280                 285

Val Asp Val Ser His Glu Asp Pro Glu Val Lys Phe Asn Trp Tyr Val
    290                 295                 300

Asp Gly Val Glu Val His Asn Ala Lys Thr Lys Pro Arg Glu Glu Gln
305                 310                 315                 320

Tyr Asn Ser Thr Tyr Arg Val Val Ser Val Leu Thr Val Leu His Gln
                325                 330                 335

Asp Trp Leu Asn Gly Lys Glu Tyr Lys Cys Lys Val Ser Asn Lys Ala
            340                 345                 350

Leu Pro Ala Pro Ile Glu Lys Thr Ile Ser Lys Ala Lys Gly Gln Pro
        355                 360                 365

Arg Glu Pro Gln Val Tyr Thr Leu Pro Pro Ser Arg Glu Glu Met Thr
    370                 375                 380

Lys Asn Gln Val Ser Leu Thr Cys Leu Val Lys Gly Phe Tyr Pro Ser
385                 390                 395                 400

Asp Ile Ala Val Glu Trp Glu Ser Asn Gly Gln Pro Glu Asn Asn Tyr
                405                 410                 415

Lys Thr Thr Pro Pro Val Leu Asp Ser Asp Gly Ser Phe Phe Leu Tyr
            420                 425                 430

Ser Lys Leu Thr Val Asp Lys Ser Arg Trp Gln Gln Gly Asn Val Phe
        435                 440                 445

Ser Cys Ser Val Met His Glu Ala Leu His Asn His Tyr Thr Gln Lys
    450                 455                 460

Ser Leu Ser Leu Ser Pro Gly Lys
465                 470

<210> SEQ ID NO 31
<211> LENGTH: 339
<212> TYPE: DNA
<213> ORGANISM: Homo sapiens

<400> SEQUENCE: 31
gacattgtga tgacccaatc tccagactct ttggctgtgt ctctagggga gagggccacc      60
atcaactgca agtccagtca gagccttta tattctagaa atcaaaagaa ctacttggcc     120
tggtatcagc agaaaccagg acagccaccc aaactcctca tcttttgggc tagcactagg     180
gaatctgggg tacctgatag gttcagtggc agtgggtttg ggacagactt caccctcacc     240
attagcagcc tgcaggctga agatgtggca gtttattact gtcagcaata ttttagctat     300
ccgctcacgt tcggacaagg gaccaaggtg gaaataaaa                            339

<210> SEQ ID NO 32
<211> LENGTH: 113
<212> TYPE: PRT
<213> ORGANISM: Homo sapiens

<400> SEQUENCE: 32

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Tyr Ser
             20                  25                  30
```

```
Arg Asn Gln Lys Asn Tyr Leu Ala Trp Tyr Gln Gln Lys Pro Gly Gln
            35                  40                  45

Pro Pro Lys Leu Leu Ile Phe Trp Ala Ser Thr Arg Glu Ser Gly Val
     50                  55                  60

Pro Asp Arg Phe Ser Gly Ser Gly Phe Gly Thr Asp Phe Thr Leu Thr
 65                  70                  75                  80

Ile Ser Ser Leu Gln Ala Glu Asp Val Ala Val Tyr Cys Gln Gln
                85                  90                  95

Tyr Phe Ser Tyr Pro Leu Thr Phe Gly Gln Gly Thr Lys Val Glu Ile
            100                 105                 110

Lys

<210> SEQ ID NO 33
<211> LENGTH: 113
<212> TYPE: PRT
<213> ORGANISM: Homo sapiens

<400> SEQUENCE: 33

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Tyr Ser
             20                  25                  30

Arg Asn Gln Lys Asn Tyr Leu Ala Trp Phe Gln Gln Lys Pro Gly Gln
            35                  40                  45

Pro Pro Lys Leu Leu Ile Phe Trp Ala Ser Thr Arg Glu Ser Gly Val
     50                  55                  60

Pro Asp Arg Phe Ser Gly Ser Gly Phe Gly Thr Asp Phe Thr Leu Thr
 65                  70                  75                  80

Ile Ser Ser Leu Gln Ala Glu Asp Val Ala Val Tyr Asp Cys Gln Gln
                85                  90                  95

Tyr Phe Ser Tyr Pro Leu Thr Phe Gly Gln Gly Thr Lys Val Glu Ile
            100                 105                 110

Lys

<210> SEQ ID NO 34
<211> LENGTH: 113
<212> TYPE: PRT
<213> ORGANISM: Homo sapiens

<400> SEQUENCE: 34

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Ser Leu Leu Tyr Ser
             20                  25                  30

Arg Asn Gln Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
     50                  55                  60

Pro Asp Arg Phe Ser Gly Ser Gly Phe Gly Thr Asp Phe Thr Leu Thr
 65                  70                  75                  80

Ile Ser Ser Leu Gln Ala Glu Asp Val Ala Val Tyr Tyr Cys Gln Gln
                85                  90                  95

Tyr Phe Ser Tyr Pro Leu Thr Phe Gly Gln Gly Thr Lys Val Glu Ile
            100                 105                 110

Lys
```

<210> SEQ ID NO 35
<211> LENGTH: 8068
<212> TYPE: DNA
<213> ORGANISM: Homo sapiens

<400> SEQUENCE: 35

| | | | | | |
|---|---|---|---|---|---|
| gaattccagc | acactggcgg | ccgttactag | ttattaatag | taatcaatta | cggggtcatt | 60 |
| agttcatagc | ccatatatgg | agttccgcgt | tacataactt | acggtaaatg | gcccgcctgg | 120 |
| ctgaccgccc | aacgaccccc | gcccattgac | gtcaataatg | acgtatgttc | ccatagtaac | 180 |
| gccaataggg | actttccatt | gacgtcaatg | ggtggagtat | ttacggtaaa | ctgcccactt | 240 |
| ggcagtacat | caagtgtatc | atatgccaag | tacgccccct | attgacgtca | atgacggtaa | 300 |
| atggcccgcc | tggcattatg | cccagtacat | gaccttatgg | gactttccta | cttggcagta | 360 |
| catctacgta | ttagtcatcg | ctattaccat | ggtgatgcgg | ttttggcagt | acatcaatgg | 420 |
| gcgtggatag | cggtttgact | cacggggatt | tccaagtctc | caccccattg | acgtcaatgg | 480 |
| gagtttgttt | tggcaccaaa | atcaacggga | ctttccaaaa | tgtcgtaaca | actccgcccc | 540 |
| attgacgcaa | atgggcggta | ggcgtgtacg | gtgggaggtc | tatataagca | gagctcgttt | 600 |
| agtgaaccgt | cagatcgcct | ggagacgcca | tccacgctgt | tttgacctcc | atagaagaca | 660 |
| ccgggaccga | tccagcctcc | gcggccggga | acggtgcatt | ggaacgcgga | ttccccgtgc | 720 |
| caagagtgac | gtaagtaccg | cctatagagt | ctataggccc | accccttgg | cttcttatgc | 780 |
| atgctatact | gttttttggct | tggggtctat | acaccccgc | ttcctcatgt | tataggtgat | 840 |
| ggtatagctt | agcctatagg | tgtgggttat | tgaccattat | tgaccactcc | cctattggtg | 900 |
| acgatacttt | ccattactaa | tccataacat | ggctctttgc | cacaactctc | tttattggct | 960 |
| atatgccaat | acactgtcct | tcagagactg | acacggactc | tgtatttta | caggatgggg | 1020 |
| tctcatttat | tatttacaaa | ttcacatata | caacaccacc | gtccccagtg | cccgcagttt | 1080 |
| ttattaaaca | taacgtggga | tctccacgcg | aatctcggt | acgtgttccg | gacatgggct | 1140 |
| cttctccggt | agcggcggag | cttctacatc | cgagccctgc | tcccatgcct | ccagcgactc | 1200 |
| atggtcgctc | ggcagctcct | tgctcctaac | agtggaggcc | agacttaggc | acagcacgat | 1260 |
| gcccaccacc | accagtgtgc | cgcacaaggc | cgtggcggta | gggtatgtgt | ctgaaaatga | 1320 |
| gctcggggag | cgggcttgca | ccgctgacgc | atttggaaga | cttaaggcag | cggcagaaga | 1380 |
| agatgcaggc | agctgagttg | ttgtgttctg | ataagagtca | gaggtaactc | ccgttgcggt | 1440 |
| gctgttaacg | gtggagggca | gtgtagtctg | agcagtactc | gttgctgccg | cgcgcgccac | 1500 |
| cagacataat | agctgacaga | ctaacagact | gttccttttcc | atgggtcttt | tctgcagtca | 1560 |
| ccgtccttga | cacgcgtctc | gggaagcttg | ccgccaccat | ggagacagac | acactcctgc | 1620 |
| tatgggtgct | gctgctctgg | gttccaggtt | cctccggaga | cattgtgatg | acccaatctc | 1680 |
| cagactcttt | ggctgtgtct | ctaggggaga | gggccaccat | caactgcaag | tccagtcaga | 1740 |
| gccttttata | ttctagaaat | caaaagaact | acttggcctg | gtatcagcag | aaaccaggac | 1800 |
| agccacccaa | actcctcatc | ttttgggcta | gcactaggga | atctgggta | cctgataggt | 1860 |
| tcagtggcag | tgggtttggg | acagacttca | ccctcaccat | tagcagcctg | caggctgaag | 1920 |
| atgtggcagt | ttattactgt | cagcaatatt | ttagctatcc | gctcacgttc | ggacaaggga | 1980 |
| ccaaggtgga | aataaaacgt | gagtggatcc | atctgggata | agcatgctgt | tttctgtctg | 2040 |
| tccctaacat | gccctgtgat | tatgcgcaaa | caacacaccc | aagggcagaa | ctttgttact | 2100 |

-continued

```
taaacaccat cctgtttgct tctttcctca ggaactgtgg ctgcaccatc tgtcttcatc      2160
ttcccgccat ctgatgagca gttgaaatct ggaactgcct ctgttgtgtg cctgctgaat      2220
aacttctatc ccagagaggc caaagtacag tggaaggtgg ataacgccct ccaatcgggt      2280
aactcccagg agagtgtcac agagcaggac agcaaggaca gcacctacag cctcagcagc      2340
accctgacgc tgagcaaagc agactacgag aaacacaaag tctacgcctg cgaagtcacc      2400
catcagggcc tgagctcgcc cgtcacaaag agcttcaaca ggggagagtg ttagagggag      2460
aagtgccccc acctgctcct cagttccagc ctgaccccct cccatccttt ggcctctgac      2520
cctttttcca caggggacct acccctattg cggtcctcca gctcatcttt cacctcaccc      2580
ccctcctcct ccttggcttt aattatgcta atgttggagg agaatgaata aataaagtga      2640
atctttgcac ctgtggtgga tctaataaaa gatatttatt ttcattagat atgtgtgttg      2700
gttttttgtg tgcagtgcct ctatctggag gccaggtagg gctggccttg ggggagggg      2760 aggccagaat gactccaaga gctacaggaa ggcaggtcag agacccccact ggacaaacag      2820 tggctggact ctgcaccata acacacaatc aacaggggag tgagctggaa atttgctagc      2880
gaattcttga agacgaaagg gcctcgtgat acgcctattt ttataggtta atgtcatgat      2940
aataatggtt tcttagacgt caggtggcac ttttcgggga aatgtgcgcg gaaccccctat      3000 ttgtttattt ttctaaatac attcaaatat gtatccgctc atgagacaat aaccctgata      3060
aatgcttcaa taatattgaa aaaggaagag tatgagtatt caacatttcc gtgtcgccct      3120
tattcccttt tttgcggcat tttgccttcc tgttttttgct cacccagaaa cgctggtgaa      3180
agtaaaagat gctgaagatc agttgggtgc acgagtgggt tacatcgaac tggatctcaa      3240
cagcggtaag atccttgaga gttttcgccc cgaagaacgt tttccaatga tgagcacttt      3300
taaagttctg ctatgtggcg cggtattatc ccgtgttgac gccgggcaag agcaactcgg      3360
tcgccgcata cactattctc agaatgactt ggttgagtac tcaccagtca cagaaaagca      3420
tcttacggat ggcatgacag taagagaatt atgcagtgct gccataacca tgagtgataa      3480
cactgcggcc aacttacttc tgacaacgat cggaggaccg aaggagctaa ccgcttttt      3540 gcacaacatg ggggatcatg taactcgcct tgatcgttgg gaaccggagc tgaatgaagc      3600
cataccaaac gacgagcgtg acaccacgat gcctgcagca atggcaacaa cgttgcgcaa      3660
actattaact ggcgaactac ttactctagc ttcccggcaa caattaatag actggatgga      3720
ggcggataaa gttgcaggac cacttctgcg ctcggccctt ccggctggct ggtttattgc      3780
tgataaatct ggagccggtg agcgtgggtc tcgcggtatc attgcagcac tggggccaga      3840
tggtaagccc tcccgtatcg tagttatcta cacgacgggg agtcaggcaa ctatggatga      3900
acgaaataga cagatcgctg agataggtgc ctcactgatt aagcattggt aactgtcaga      3960
ccaagtttac tcatatatac tttagattga tttaaaactt catttttaat ttaaaaggat      4020
ctaggtgaag atccttttg ataatctcat gaccaaaatc ccttaacgtg agttttcgtt      4080
ccactgagcg tcagaccccg tagaaaagat caaaggatct tcttgagatc ctttttttct      4140
gcgcgtaatc tgctgcttgc aaacaaaaaa accaccgcta ccagcggtgg tttgtttgcc      4200
ggatcaagag ctaccaactc ttttccgaa ggtaactggc ttcagcagag cgcagatacc      4260
aaatactgtc cttctagtgt agccgtagtt aggccaccac ttcaagaact ctgtagcacc      4320
gcctacatac ctcgctctgc taatcctgtt accagtggct gctgccagtg gcgataagtc      4380
gtgtcttacc gggttggact caagacgata gttaccggat aaggcgcagc ggtcgggctg      4440
aacggggggt tcgtgcacac agcccagctt ggagcgaacg acctacaccg aactgagata      4500
```

-continued

```
cctacagcgt gagctatgag aaagcgccac gcttcccgaa gggagaaagg cggacaggta    4560
tccggtaagc ggcagggtcg gaacaggaga gcgcacgagg gagcttccag ggggaaacgc    4620
ctggtatctt tatagtcctg tcgggtttcg ccacctctga cttgagcgtc gattttttgtg   4680 atgctcgtca gggggggcgga gcctatggaa aaacgccagc aacgcggcct ttttacggtt   4740
cctggccttt tgctggcctt tgctcacat gttctttcct gcgttatccc ctgattctgt     4800
ggataaccgt attaccgcct ttgagtgagc tgataccgct cgccgcagcc gaacgaccga    4860
gcgcagcgag tcagtgagcg aggaagcgga agagcgcctg atgcggtatt ttctccttac   4920
gcatctgtgc ggtatttcac accgcatatg gtgcactctc agtacaatct gctctgatgc   4980
cgcatagtta agccagtata cactccgcta tcgctacgtg actgggtcat ggctgcgccc   5040
cgacacccgc caacacccgc tgacgcgccc tgacgggctt gtctgctccc ggcatccgct   5100
tacagacaag ctgtgaccgt ctccgggagc tgcatgtgtc agaggttttc accgtcatca   5160
ccgaaacgcg cgaggcagct gtggaatgtg tgtcagttag ggtgtggaaa gtccccaggc   5220
tccccagcag gcagaagtat gcaaagcatg catctcaatt agtcagcaac caggctcccc   5280
agcaggcaga agtatgcaaa gcatgcatct caattagtca gcaaccatag tcccgcccct   5340
aactccgccc atcccgcccc taactccgcc cagttccgcc cattctccgc ccatggctg    5400 actaatttt tttatttatg cagaggccga ggccgcctcg gcctctgagc tattccagaa    5460
gtagtgagga ggcttttttg gaggcctagg cttttgcaaa aagctagctt cacgctgccg   5520
caagcactca gggcgcaagg gctgctaaag gaagcggaac acgtagaaag ccagtccgca   5580
gaaacggtgc tgacccggga tgaatgtcag ctactgggct atctggacaa gggaaaacgc   5640
aagcgcaaag agaaagcagg tagcttgcag tgggcttaca tggcgatagc tagactgggc   5700
ggttttatgg acagcaagcg aaccggaatt gccagctggg gcgccctctg gtaaggttgg   5760
gaagccctgc aaagtaaact ggatggcttt cttgccgcca aggatctgat ggcgcagggg   5820
atcaagatct gatcaagaga caggatgagg atcgtttcgc atgattgaac aagatggatt   5880
gcacgcaggt tctccggccg cttgggtgga gaggctattc ggctatgact gggcacaaca   5940
gacaatcggc tgctctgatg ccgccgtgtt ccggctgtca gcgcagggc gcccggttct    6000 ttttgtcaag accgacctgt ccggtgccct gaatgaactg caggacgagg cagcgcggct   6060
atcgtggctg gccacgacgg gcgttccttg cgcagctgtg ctcgacgttg tcactgaagc   6120
gggaagggac tggctgctat tgggcgaagt gccggggcag gatctcctgt catctcacct   6180
tgctcctgcc gagaaagtat ccatcatggc tgatgcaatg cggcggctgc atacgcttga   6240
tccggctacc tgcccattcg accaccaagc gaaacatcgc atcgagcgag cacgtactcg   6300
gatggaagcc ggtcttgtcg atcaggatga tctggacgaa gagcatcagg ggctcgcgcc   6360
agccgaactg ttcgccaggc tcaaggcgcg catgcccgac ggcgaggatc tcgtcgtgac   6420
ccatggcgat gcctgcttgc cgaatatcat ggtggaaaat ggccgctttt ctggattcat   6480
cgactgtggc cggctgggtg tggcggaccg ctatcaggac atagcgttgg ctacccgtga   6540
tattgctgaa gagcttggcg gcgaatgggc tgaccgcttc ctcgtgcttt acggtatcgc   6600
cgctcccgat tcgcagcgca tcgccttcta tcgccttctt gacgagttct tctgagcggg   6660 actctgggt tcgaaatgac cgaccaagcg acgcccaacc tgccatcacg agatttcgat    6720
tccaccgccg ccttctatga aaggttgggc ttcggaatcg ttttccggga cgccggctgg   6780
atgatcctcc agcgcgggga tctcatgctg gagttcttcg cccaccccgg gctcgatccc   6840
```

```
ctcgcgagtt ggttcagctg ctgcctgagg ctggacgacc tcgcggagtt ctaccggcag    6900
tgcaaatccg tcggcatcca ggaaaccagc agcggctatc cgcgcatcca tgcccccgaa    6960
ctgcaggagt ggggaggcac gatggccgct tggtcccgg atctttgtga aggaacctta    7020
cttctgtggt gtgacataat tggacaaact acctacagag atttaaagct ctaaggtaaa    7080
tataaaattt ttaagtgtat aatgtgttaa actactgatt ctaattgttt gtgtatttta    7140
gattccaacc tatggaactg atgaatggga gcagtggtgg aatgccttta atgaggaaaa    7200
cctgttttgc tcagaagaaa tgccatctag tgatgatgag ctactgctg actctcaaca    7260 ttctactcct ccaaaaaga agagaaaggt agaagacccc aaggactttc cttcagaatt    7320
gctaagtttt ttgagtcatg ctgtgtttag taatagaact cttgcttgct ttgctattta    7380
caccacaaag gaaaaagctg cactgctata caagaaaatt atggaaaaat attctgtaac    7440
ctttataagt aggcataaca gttataatca taacatactg tttttctta ctccacacag    7500 gcatagagtg tctgctatta ataactatgc tcaaaaattg tgtaccttta gcttttttaat    7560 ttgtaaaggg gttaataagg aatatttgat gtatagtgcc ttgactagag atcataatca    7620
gccataccac atttgtagag gttttacttg ctttaaaaaa cctcccacac ctcccctga    7680 acctgaaaca taaatgaat gcaattgttg ttgttaactt gtttattgca gcttataatg    7740
gttacaaata aagcaatagc atcacaaatt tcacaaataa agcattttt tcactgcatt    7800 ctagttgtgg tttgtccaaa ctcatcaatg tatcttatca tgtctggatc taataaaaga    7860
tatttatttt cattagatat gtgtgttggt ttttgtgtg cagtgcctct atctggaggc    7920
caggtagggc tggccttggg ggaggggag gccagaatga ctccaagagc tacaggaagg    7980
caggtcagag accccactgg acaaacagtg gctggactct gcaccataac acacaatcaa    8040
caggggagtg agctggaaat ttgctagc                                      8068
```

<210> SEQ ID NO 36
<211> LENGTH: 240
<212> TYPE: PRT
<213> ORGANISM: Homo sapiens

<400> SEQUENCE: 36

```
Met Glu Thr Asp Thr Leu Leu Leu Trp Val Leu Leu Leu Trp Val Pro
  1               5                  10                  15

Gly Ser Ser Gly Asp Ile Val Met Thr Gln Ser Pro Asp Ser Leu Ala
                 20                  25                  30

Val Ser Leu Gly Glu Arg Ala Thr Ile Asn Cys Lys Ser Ser Gln Ser
             35                  40                  45

Leu Leu Tyr Ser Arg Asn Gln Lys Asn Tyr Leu Ala Trp Tyr Gln Gln
         50                  55                  60

Lys Pro Gly Gln Pro Pro Lys Leu Leu Ile Phe Trp Ala Ser Thr Arg
 65                  70                  75                  80

Glu Ser Gly Val Pro Asp Arg Phe Ser Gly Ser Gly Phe Gly Thr Asp
                 85                  90                  95

Phe Thr Leu Thr Ile Ser Ser Leu Gln Ala Glu Asp Val Ala Val Tyr
            100                 105                 110

Tyr Cys Gln Gln Tyr Phe Ser Tyr Pro Leu Thr Phe Gly Gln Gly Thr
        115                 120                 125

Lys Val Glu Ile Lys Arg Thr Val Ala Ala Pro Ser Val Phe Ile Phe
    130                 135                 140

Pro Pro Ser Asp Glu Gln Leu Lys Ser Gly Thr Ala Ser Val Val Cys
145                 150                 155                 160
```

```
Leu Leu Asn Asn Phe Tyr Pro Arg Glu Ala Lys Val Gln Trp Lys Val
                165                 170                 175

Asp Asn Ala Leu Gln Ser Gly Asn Ser Gln Glu Ser Val Thr Glu Gln
            180                 185                 190

Asp Ser Lys Asp Ser Thr Tyr Ser Leu Ser Ser Thr Leu Thr Leu Ser
        195                 200                 205

Lys Ala Asp Tyr Glu Lys His Lys Val Tyr Ala Cys Glu Val Thr His
    210                 215                 220

Gln Gly Leu Ser Ser Pro Val Thr Lys Ser Phe Asn Arg Gly Glu Cys
225                 230                 235                 240
```

<210> SEQ ID NO 37
<211> LENGTH: 372
<212> TYPE: DNA
<213> ORGANISM: Homo sapiens

<400> SEQUENCE: 37

```
caggtgcaac tagtgcagtc cggcgccgaa gtgaagaaac ccggtgcttc cgtgaaagtc    60
agctgtaaaa ctagtagata caccttcact gaatacacca tacactgggt tagacaggcc   120
cctggccaaa ggctggagtg gataggaggt attaatccta acaatggtat tcctaactac   180
aaccagaagt tcaagggccg ggccaccttg accgtaggca gtctgccag caccgcctac   240
atggaactgt ccagcctgcg ctccgaggac actgcagtct actactgcgc cagaagaaga   300
atcgcctatg gttacgacga gggccatgct atggactact ggggtcaagg aacccttgtc   360
accgtctcct ca                                                       372
```

<210> SEQ ID NO 38
<211> LENGTH: 124
<212> TYPE: PRT
<213> ORGANISM: Homo sapiens

<400> SEQUENCE: 38

```
Gln Val Gln Leu Val Gln Ser Gly Ala Glu Val Lys Lys Pro Gly Ala
  1               5                  10                  15

Ser Val Lys Val Ser Cys Lys Thr Ser Arg Tyr Thr Phe Thr Glu Tyr
             20                  25                  30

Thr Ile His Trp Val Arg Gln Ala Pro Gly Gln Arg Leu Glu Trp Ile
         35                  40                  45

Gly Gly Ile Asn Pro Asn Asn Gly Ile Pro Asn Tyr Asn Gln Lys Phe
     50                  55                  60

Lys Gly Arg Ala Thr Leu Thr Val Gly Lys Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser
        115                 120
```

<210> SEQ ID NO 39
<211> LENGTH: 124
<212> TYPE: PRT
<213> ORGANISM: Homo sapiens

<400> SEQUENCE: 39

```
Gln Val Gln Leu Val Gln Ser Gly Ala Glu Val Lys Lys Pro Gly Ala
```

-continued

```
             1               5                  10                 15
        Ser Val Lys Val Ser Cys Lys Thr Ser Arg Tyr Thr Phe Thr Glu Tyr
                         20                 25                 30

Thr Ile His Trp Val Arg Gln Ala Pro Gly Gln Arg Leu Glu Trp Ile
                     35                 40                 45

Gly Gly Ile Asn Pro Asn Asn Gly Ile Pro Asn Tyr Asn Gln Lys Phe
                 50                 55                 60

Lys Gly Arg Ala Thr Leu Thr Val Gly Lys Ser Ala Ser Thr Ala Tyr
         65                 70                 75                 80

Met Glu Leu Ser Ser Leu Arg Ser Glu Asp Thr Ala Val Tyr Phe Cys
                         85                 90                 95

Ala Arg Arg Arg Ile Ala Tyr Gly Tyr Asp Glu Gly His Ala Met Asp
                        100                105                110

Tyr Trp Gly Gln Gly Thr Leu Val Thr Val Ser Ser
                    115                120
```

<210> SEQ ID NO 40
<211> LENGTH: 124
<212> TYPE: PRT
<213> ORGANISM: Homo sapiens

<400> SEQUENCE: 40

```
             1               5                  10                 15
        Gln Val Gln Leu Val Gln Ser Gly Ala Glu Val Lys Lys Pro Gly Ala

Ser Val Lys Val Ser Cys Lys Thr Ser Arg Tyr Thr Phe Thr Glu Tyr
                         20                 25                 30

Thr Ile His Trp Val Arg Gln Ala Pro Gly Gln Arg Leu Glu Trp Ile
                     35                 40                 45

Gly Gly Ile Asn Pro Asn Asn Gly Ile Pro Asn Tyr Asn Gln Lys Phe
                 50                 55                 60

Lys Gly Arg Val Thr Ile Thr Val Asp Thr Ser Ala Ser Thr Ala Tyr
         65                 70                 75                 80

Met Glu Leu Ser Ser Leu Arg Ser Glu Asp Thr Ala Val Tyr Tyr Cys
                         85                 90                 95

Ala Arg Arg Arg Ile Ala Tyr Gly Tyr Asp Glu Gly His Ala Met Asp
                        100                105                110

Tyr Trp Gly Gln Gly Thr Leu Val Thr Val Ser Ser
                    115                120
```

<210> SEQ ID NO 41
<211> LENGTH: 124
<212> TYPE: PRT
<213> ORGANISM: Homo sapiens

<400> SEQUENCE: 41

```
             1               5                  10                 15
        Gln Val Gln Leu Val Gln Ser Gly Ala Glu Val Lys Lys Pro Gly Ala

Ser Val Lys Val Ser Cys Lys Thr Ser Gly Tyr Thr Phe Thr Glu Tyr
                         20                 25                 30

Thr Ile His Trp Val Arg Gln Ala Pro Gly Gln Arg Leu Glu Trp Ile
                     35                 40                 45

Gly Gly Ile Asn Pro Asn Asn Gly Ile Pro Asn Tyr Asn Gln Lys Phe
                 50                 55                 60

Lys Gly Arg Val Thr Ile Thr Val Asp Thr Ser Ala Ser Thr Ala Tyr
         65                 70                 75                 80

Met Glu Leu Ser Ser Leu Arg Ser Glu Asp Thr Ala Val Tyr Tyr Cys
```

-continued

```
                    85                  90                  95
Ala Arg Arg Arg Ile Ala Tyr Gly Tyr Asp Glu Gly His Ala Met Asp
                100                 105                 110
Tyr Trp Gly Gln Gly Thr Leu Val Thr Val Ser Ser
        115                 120

<210> SEQ ID NO 42
<211> LENGTH: 7731
<212> TYPE: DNA
<213> ORGANISM: Homo sapiens

<400> SEQUENCE: 42
ttgaagacga aagggcctcg tgatacgcct atttttatag gttaatgtca tgataataat      60
ggtttcttag acgtcaggtg cacttttcg gggaaatgtg cgcggaaccc ctatttgttt     120
attttctaa atacattcaa atatgtatcc gctcatgaga caataaccct gataaatgct     180
tcaataatat tgaaaaagga gagtatgag tattcaacat ttccgtgtcg cccttattcc     240
cttttttgcg gcattttgcc ttcctgtttt tgctcaccca gaaacgctgg tgaaagtaaa     300
agatgctgaa gatcagttgg gtgcacgagt gggttacatc gaactggatc tcaacagcgg     360
taagatcctt gagagttttc gccccgaaga acgttttcca atgatgagca cttttaaagt     420
tctgctatgt ggcgcggtat tatcccgtgt tgacgccggg caagagcaac tcggtcgccg     480
catacactat tctcagaatg acttggttga gtactcacca gtcacagaaa agcatcttac     540
ggatggcatg acagtaagag aattatgcag tgctgccata accatgagtg ataacactgc     600
ggccaactta cttctgacaa cgatcggagg accgaaggag ctaaccgctt ttttgcacaa     660
catgggggat catgtaactc gccttgatcg ttgggaaccg gagctgaatg aagccatacc     720
aaacgacgag cgtgacacca cgatgcctgc agcaatggca acaacgttgc gcaaactatt     780
aactggcgaa ctacttactc tagcttcccg gcaacaatta atagactgga tggaggcgga     840
taaagttgca ggaccacttc tgcgctcggc ccttccggct ggctggttta ttgctgataa     900
atctggagcc ggtgagcgtg ggtctcgcgg tatcattgca gcactgggc cagatggtaa     960
gccctcccgt atcgtagtta tctacacgac ggggagtcag gcaactatgg atgaacgaaa    1020
tagacagatc gctgagatag gtgcctcact gattaagcat tggtaactgt cagaccaagt    1080
ttactcatat atactttaga ttgatttaaa acttcatttt taatttaaaa ggatctaggt    1140
gaagatcctt tttgataatc tcatgaccaa aatcccttaa cgtgagtttt cgttccactg    1200
agcgtcagac cccgtagaaa agatcaaagg atcttcttga tccttttt ttctgcgcgt     1260
aatctgctgc ttgcaaacaa aaaaaccacc gctaccagcg gtggtttgtt tgccggatca    1320
agagctacca actcttttc cgaaggtaac tggcttcagc agagcgcaga taccaaatac    1380
tgtccttcta gtgtagccgt agttaggcca ccacttcaag aactctgtag caccgcctac    1440
atacctcgct ctgctaatcc tgttaccagt ggctgctgcc agtggcgata gtcgtgtct     1500
taccgggttg gactcaagac gatagttacc ggataaggcg cagcggtcgg gctgaacggg    1560
gggttcgtgc acacagccca gcttggagcg aacgacctac accgaactga gatacctaca    1620
gcgtgagcta tgagaaagcg ccacgcttcc gaagggaga aaggcggaca ggtatccggt     1680
aagcggcagg gtcggaacag gagagcgcac gagggagctt ccaggggaa acgcctggta    1740
tctttatagt cctgtcgggt ttcgccacct ctgacttgag cgtcgatttt tgtgatgctc    1800
gtcaggggg cggagcctat ggaaaaacgc cagcaacgc gcctttttac ggttcctggc     1860
cttttgctgg ccttttgctc acatgttctt tcctgcgtta tccctgatt ctgtggataa    1920
```

```
ccgtattacc gcctttgagt gagctgatac cgctcgccgc agccgaacga ccgagcgcag    1980
cgagtcagtg agcgaggaag cggaagagcg cctgatgcgg tattttctcc ttacgcatct    2040
gtgcggtatt tcacaccgca tatggtgcac tctcagtaca atctgctctg atgccgcata    2100
gttaagccag tatacactcc gctatcgcta cgtgactggg tcatggctgc gccccgacac    2160
ccgccaacac ccgctgacgc gccctgacgg gcttgtctgc tcccggcatc cgcttacaga    2220
caagctgtga ccgtctccgg gagctgcatg tgtcagaggt tttaccgtc atcaccgaaa     2280
cgcgcgaggc agcatgcatc tcaattagtc agcaaccata gtcccgcccc taactccgcc    2340
catcccgccc ctaactccgc ccagttccgc ccattctccg ccccatggct gactaatttt    2400
ttttatttat gcagaggccg aggccgcctc ggcctctgag ctattccaga agtagtgagg    2460
aggcttttt ggaggcctag gcttttgcaa aaagctagct tacagctcag gctgcgatt     2520
tcgcgccaaa cttgacggca atcctagcgt gaaggctgg aggattttat ccccgctgcc    2580
atcatggttc gaccattgaa ctgcatcgtc gccgtgtccc aaaatatggg gattggcaag    2640
aacggagacc taccctggcc tccgctcagg aacgagttca agtacttcca agaatgacc     2700
acaacctctt cagtggaagg taaacagaat ctggtgatta tgggtaggaa aacctggttc    2760
tccattcctg agaagaatcg accttttaaag gacagaatta atatagttct cagtagagaa    2820
ctcaaagaac caccacgagg agctcatttt cttgccaaaa gtttggatga tgccttaaga    2880
cttattgaac aaccggaatt ggcaagtaaa gtagacatgg tttggatagt cggaggcagt    2940
tctgtttacc aggaagccat gaatcaacca ggccacctca gactctttgt gacaaggatc    3000
atgcaggaat ttgaaagtga cacgtttttc ccagaaattg atttggggaa atataaactt    3060
ctcccagaat acccaggcgt cctctctgag gtccaggagg aaaaaggcat caagtataag    3120
tttgaagtct acgagaagaa agactaacag gaagatgctt tcaagttctc tgctcccctc    3180
ctaaagctat gcattttat aagaccatgg gacttttgct ggctttagat ctttgtgaag     3240
gaaccttact tctgtggtgt gacataattg gacaaactac ctacagagat ttaaagctct    3300
aaggtaaata taaattttt aagtgtataa tgtgttaaac tactgattct aattgtttgt     3360
gtatttaga ttccaaccta tggaactgat gaatgggagc agtggtggaa tgcctttaat     3420
gaggaaaacc tgttttgctc agaagaaatg ccatctagtg atgatgaggc tactgctgac    3480
tctcaacatt ctactcctcc aaaaaagaag agaaaggtag aagacccaa ggactttcct     3540
tcagaattgc taagtttttt gagtcatgct gtgtttagta atagaactct tgcttgcttt    3600
gctatttaca ccacaaagga aaagctgca ctgctataca agaaaattat ggaaaaatat     3660
tctgtaacct ttataagtag gcataacagt tataatcata acatactgtt ttttcttact    3720
ccacacaggc atagagtgtc tgctattaat aactatgctc aaaaattgtg tacctttagc    3780
tttttaattt gtaagggt taataaggaa tatttgatgt atagtgcctt gactagagat      3840
cataatcagc cataccacat ttgtagaggt tttacttgct ttaaaaaacc tcccacacct    3900
ccccctgaac ctgaaacata aaatgaatgc aattgttgtt gttaacttgt ttattgcagc    3960
ttataatggt tacaaataaa gcaatagcat cacaaatttc acaaataaag catttttttc    4020
actgcattct agttgtggtt tgtccaaact catcaatgta tcttatcatg tctggatcta    4080
ataaagata tttattttca ttagatatgt gtgttggttt tttgtgtgca gtgcctctat     4140
ctggaggcca gtagggctg gccttggggg aggggaggc cagaatgact ccaagagcta     4200
caggaaggca ggtcagagac cccactggac aaacagtggc tggactctgc accataacac    4260
```

-continued

```
acaatcaaca gggagtgag ctggaaattt gctagcgaat tccagcacac tggcggccgt    4320
tactagttat taatagtaat caattacggg gtcattagtt catagcccat atatggagtt    4380
ccgcgttaca taacttacgg taaatggccc gcctggctga ccgcccaacg accccccgccc   4440 attgacgtca ataatgacgt atgttcccat agtaacgcca atagggactt tccattgacg    4500
tcaatgggtg gagtatttac ggtaaactgc ccacttggca gtacatcaag tgtatcatat    4560
gccaagtacg cccctattg acgtcaatga cggtaaatgg cccgcctggc attatgccca    4620
gtacatgacc ttatgggact ttcctacttg gcagtacatc tacgtattag tcatcgctat    4680
taccatggtg atgcggtttt ggcagtacat caatgggcgt ggatagcggt ttgactcacg    4740
gggatttcca gtctccacc ccattgacgt caatgggagt ttgttttggc accaaaatca     4800
acgggacttt ccaaaatgtc gtaacaactc cgccccattg acgcaaatgg gcggtaggcg    4860
tgtacggtgg gaggtctata taagcagagc tcgtttagtg aaccgtcaga tcgcctggag    4920
acgccatcca cgctgtttg acctccatag aagacaccgg gaccgatcca gcctccgcgg     4980
ccgggaacgg tgcattggaa cgcggattcc ccgtgccaag agtgacgtaa gtaccgccta    5040
tagagtctat aggcccaccc ccttggcttc ttatgcatgc tatactgttt ttggcttggg    5100
gtctatacac ccccgcttcc tcatgttata ggtgatggta tagcttagcc tataggtgtg    5160
ggttattgac cattattgac cactcccta ttggtgacga actttccat tactaatcca      5220 taacatggct ctttgccaca actctcttta ttggctatat gccaatacac tgtccttcag    5280
agactgacac ggactctgta tttttacagg atggggtctc atttattatt tacaaattca    5340
catatacaac accaccgtcc ccagtgcccg cagtttttat taaacataac gtgggatctc    5400
cacgcgaatc tcgggtacgt gttccggaca tgggctcttc tccggtagcg gcggagcttc    5460
tacatccgag ccctgctccc atgcctccag cgactcatgg tcgctcggca gctccttgct    5520
cctaacagtg gaggccagac ttaggcacag cacgatgccc accaccacca gtgtgccgca    5580
caaggccgtg gcggtagggt atgtgtctga aaatgagctc ggggagcggg cttgcaccgc    5640
tgacgcattt ggaagactta aggcagcggc agaagaagat gcaggcagct gagttgttgt    5700
gttctgataa gagtcagagg taactcccgt tgcggtgctg ttaacggtgg agggcagtgt    5760
agtctgagca gtactcgttg ctgccgcgcg cgccaccaga cataatagct gacagactaa    5820
cagactgttc cttccatgg gtcttttctg cagtcaccgt ccttgacacg cgtctcggga    5880
agcttgccgc caccatggac tggacctggc gcgtgttttg cctgctcgcc gtggctcctg    5940
gggcccacag ccaggtgcaa ctggtgcagt ccggcgccga agtgaagaaa cccggtgctt    6000
ccgtgaaagt cagctgtaaa actagtagat acaccttcac tgaatacacc atacactggg    6060
ttagacaggc ccctggccaa aggctggagt ggataggagg tattaatcct aacaatggta    6120
ttcctaacta caaccagaag ttcaagggcc gggccacctt gaccgtaggc aagtctgcca    6180
gcaccgccta catggaactg tccagcctgc gctccgagga cactgcagtc tactactgcg    6240
ccagaagaag aatcgcctat ggttacgacg agggccatgc tatggactac tggggtcaag    6300
gaacccttgt caccgtctcc tcaggtgagt ggatcctctg cgcctgggcc cagctctgtc    6360
ccacaccgcg gtcacatggc accacctctc ttgcagcctc caccaagggc ccatcggtct    6420
tccccctggc accctcctcc aagagcacct ctggggggcac agcggccctg ggctgcctgg    6480
tcaaggacta cttccccgaa ccggtgacgg tgtcgtggaa ctcaggcgcc ctgaccagcg    6540
gcgtgcacac cttcccggct gtcctacagt cctcaggact ctactccctc agcagcgtgg    6600
tgaccgtgcc ctccagcagc ttgggcaccc agacctacat ctgcaacgtg aatcacaagc    6660
```

-continued

| | |
|---|---|
| ccagcaacac caaggtggac aagaaagttg agcccaaatc ttgtgacaaa actcacacat | 6720 |
| gcccaccgtg cccagcacct gaactcctgg ggggaccgtc agtcttcctc ttccccccaa | 6780 |
| aacccaagga caccctcatg atctcccgga cccctgaggt cacatgcgtg gtggtggacg | 6840 |
| tgagccacga agaccctgag gtcaagttca actggtacgt ggacggcgtg gaggtgcata | 6900 |
| atgccaagac aaagccgcgg gaggagcagt acaacagcac gtaccgggtg gtcagcgtcc | 6960 |
| tcaccgtcct gcaccaggac tggctgaatg gcaaggagta caagtgcaag gtctccaaca | 7020 |
| aagccctccc agcccccatc gagaaaacca tctccaaagc caaagggcag ccccgagaac | 7080 |
| cacaggtgta caccctgccc ccatcccggg aggagatgac caagaaccag gtcagcctga | 7140 |
| cctgcctggt caaaggcttc tatcccagcg acatcgccgt ggagtgggag agcaatgggc | 7200 |
| agccggagaa caactacaag accacgcctc ccgtgctgga ctccgacggc tccttcttcc | 7260 |
| tctacagcaa gctcaccgtg gacaagagca ggtggcagca ggggaacgtc ttctcatgct | 7320 |
| ccgtgatgca tgaggctctg cacaaccact acacgcagaa gagcctctcc ctgtctccgg | 7380 |
| gtaaatgagt gcgacggccg gcaagccccg ctccccgggc tctcgcggtc gcacgaggat | 7440 |
| gcttggcacg tacccctgt acatacttcc cgggcgccca gcatggaaat aaagcaccgg | 7500 |
| atctaataaa agatatttat tttcattaga tatgtgtgtt ggttttttgt gtgcagtgcc | 7560 |
| tctatctgga ggccaggtag ggctggcctt gggggagggg gaggccagaa tgactccaag | 7620 |
| agctacagga aggcaggtca gagacccac tggacaaaca gtggctggac tctgcaccat | 7680 |
| aacacacaat caacagggga gtgagctgga aatttgctag cgaattaatt c | 7731 |

<210> SEQ ID NO 43
<211> LENGTH: 472
<212> TYPE: PRT
<213> ORGANISM: Homo sapiens

<400> SEQUENCE: 43

```
Met Asp Trp Thr Trp Arg Val Phe Cys Leu Leu Ala Val Ala Pro Gly
 1               5                  10                  15

Ala His Ser Gln Val Gln Leu Val Gln Ser Gly Ala Glu Val Lys Lys
            20                  25                  30

Pro Gly Ala Ser Val Lys Val Ser Cys Lys Thr Ser Arg Tyr Thr Phe
        35                  40                  45

Thr Glu Tyr Thr Ile His Trp Val Arg Gln Ala Pro Gly Gln Arg Leu
    50                  55                  60

Glu Trp Ile Gly Gly Ile Asn Pro Asn Asn Gly Ile Pro Asn Tyr Asn
65                  70                  75                  80

Gln Lys Phe Lys Gly Arg Ala Thr Leu Thr Val Gly Lys Ser Ala Ser
                85                  90                  95

Thr Ala Tyr Met Glu Leu Ser Ser Leu Arg Ser Glu Asp Thr Ala Val
            100                 105                 110

Tyr Tyr Cys Ala Arg Arg Ile Ala Tyr Gly Tyr Asp Glu Gly His
        115                 120                 125

Ala Met Asp Tyr Trp Gly Gln Gly Thr Leu Val Thr Val Ser Ser Ser
    130                 135                 140

Thr Lys Gly Pro Ser Val Phe Pro Leu Ala Pro Ser Ser Lys Ser Thr
145                 150                 155                 160

Ser Gly Gly Thr Ala Ala Leu Gly Cys Leu Val Lys Asp Tyr Phe Pro
                165                 170                 175

Glu Pro Val Thr Val Ser Trp Asn Ser Gly Ala Leu Thr Ser Gly Val
```

```
                    180              185              190
His Thr Phe Pro Ala Val Leu Gln Ser Ser Gly Leu Tyr Ser Leu Ser
        195              200              205
Ser Val Val Thr Val Pro Ser Ser Leu Gly Thr Gln Thr Tyr Ile
    210              215              220
Cys Asn Val Asn His Lys Pro Ser Asn Thr Lys Val Asp Lys Lys Val
225              230              235              240
Glu Pro Lys Ser Cys Asp Lys Thr His Thr Cys Pro Pro Cys Pro Ala
                245              250              255
Pro Glu Leu Leu Gly Gly Pro Ser Val Phe Leu Phe Pro Pro Lys Pro
                260              265              270
Lys Asp Thr Leu Met Ile Ser Arg Thr Pro Glu Val Thr Cys Val Val
            275              280              285
Val Asp Val Ser His Glu Asp Pro Glu Val Lys Phe Asn Trp Tyr Val
290              295              300
Asp Gly Val Glu Val His Asn Ala Lys Thr Lys Pro Arg Glu Glu Gln
305              310              315              320
Tyr Asn Ser Thr Tyr Arg Val Val Ser Val Leu Thr Val Leu His Gln
                325              330              335
Asp Trp Leu Asn Gly Lys Glu Tyr Lys Cys Lys Val Ser Asn Lys Ala
                340              345              350
Leu Pro Ala Pro Ile Glu Lys Thr Ile Ser Lys Ala Lys Gly Gln Pro
                355              360              365
Arg Glu Pro Gln Val Tyr Thr Leu Pro Pro Ser Arg Glu Glu Met Thr
        370              375              380
Lys Asn Gln Val Ser Leu Thr Cys Leu Val Lys Gly Phe Tyr Pro Ser
385              390              395              400
Asp Ile Ala Val Glu Trp Glu Ser Asn Gly Gln Pro Glu Asn Asn Tyr
                405              410              415
Lys Thr Thr Pro Pro Val Leu Asp Ser Asp Gly Ser Phe Phe Leu Tyr
                420              425              430
Ser Lys Leu Thr Val Asp Lys Ser Arg Trp Gln Gln Gly Asn Val Phe
            435              440              445
Ser Cys Ser Val Met His Glu Ala Leu His Asn His Tyr Thr Gln Lys
        450              455              460
Ser Leu Ser Leu Ser Pro Gly Lys
465              470

<210> SEQ ID NO 44
<211> LENGTH: 25
<212> TYPE: DNA
<213> ORGANISM: Homo sapiens

<400> SEQUENCE: 44
accgtctcct caggtgagtg gatcc                                              25

<210> SEQ ID NO 45
<211> LENGTH: 26
<212> TYPE: DNA
<213> ORGANISM: Homo sapiens

<400> SEQUENCE: 45
cctctcttgc agcctccacc aagggc                                             26

<210> SEQ ID NO 46
<211> LENGTH: 14
```

```
<212> TYPE: DNA
<213> ORGANISM: Homo sapiens

<400> SEQUENCE: 46
cctctcttgc agcc                                                      14

<210> SEQ ID NO 47
<211> LENGTH: 4
<212> TYPE: PRT
<213> ORGANISM: Homo sapiens

<400> SEQUENCE: 47

Thr Val Ser Ser
  1

<210> SEQ ID NO 48
<211> LENGTH: 4
<212> TYPE: PRT
<213> ORGANISM: Homo sapiens

<400> SEQUENCE: 48

Ser Thr Lys Gly
  1

<210> SEQ ID NO 49
<211> LENGTH: 27
<212> TYPE: DNA
<213> ORGANISM: Homo sapiens

<400> SEQUENCE: 49
accgtctcct cagcctccac caagggc                                        27

<210> SEQ ID NO 50
<211> LENGTH: 8
<212> TYPE: PRT
<213> ORGANISM: Homo sapiens

<400> SEQUENCE: 50

Thr Val Ser Ser Ser Thr Lys Gly
  1               5

<210> SEQ ID NO 51
<211> LENGTH: 27
<212> TYPE: DNA
<213> ORGANISM: Homo sapiens

<400> SEQUENCE: 51
accgtctcct cagcctccac caagggc                                        27

<210> SEQ ID NO 52
<211> LENGTH: 9
<212> TYPE: PRT
<213> ORGANISM: Homo sapiens

<400> SEQUENCE: 52

Thr Val Ser Ser Ala Ser Thr Lys Gly
  1               5

<210> SEQ ID NO 53
<211> LENGTH: 22
<212> TYPE: DNA
<213> ORGANISM: Homo sapiens

<400> SEQUENCE: 53
```

```
gaaataaaac gtgagtggat cc                                           22
```

<210> SEQ ID NO 54
<211> LENGTH: 27
<212> TYPE: DNA
<213> ORGANISM: Homo sapiens

<400> SEQUENCE: 54

```
cttctttcct caggaactgt ggctgca                                      27
```

<210> SEQ ID NO 55
<211> LENGTH: 4
<212> TYPE: PRT
<213> ORGANISM: Homo sapiens

<400> SEQUENCE: 55

Thr Val Ala Ala
 1

<210> SEQ ID NO 56
<211> LENGTH: 24
<212> TYPE: DNA
<213> ORGANISM: Homo sapiens

<400> SEQUENCE: 56

```
gaaataaaac gaactgtggc tgca                                         24
```

<210> SEQ ID NO 57
<211> LENGTH: 7
<212> TYPE: PRT
<213> ORGANISM: Homo sapiens

<400> SEQUENCE: 57

Glu Ile Lys Thr Val Ala Ala
 1               5

<210> SEQ ID NO 58
<211> LENGTH: 24
<212> TYPE: DNA
<213> ORGANISM: Homo sapiens

<400> SEQUENCE: 58

```
gaaataaaac gaactgtggc tgca                                         24
```

<210> SEQ ID NO 59
<211> LENGTH: 8
<212> TYPE: PRT
<213> ORGANISM: Homo sapiens

<400> SEQUENCE: 59

Glu Ile Lys Arg Thr Val Ala Ala
 1               5

<210> SEQ ID NO 60
<211> LENGTH: 20
<212> TYPE: PRT
<213> ORGANISM: Homo sapiens

<400> SEQUENCE: 60

Met Asp Ser Gln Ala Gln Val Leu Met Leu Leu Leu Trp Val Ser
 1               5                  10                  15
Gly Thr Cys Gly
            20

```
<210> SEQ ID NO 61
<211> LENGTH: 19
<212> TYPE: PRT
<213> ORGANISM: Homo sapiens

<400> SEQUENCE: 61

Met Gly Trp Ser Trp Val Phe Leu Phe Leu Leu Ser Gly Thr Ala Gly
 1               5                  10                  15

Val Leu Ser

<210> SEQ ID NO 62
<211> LENGTH: 9
<212> TYPE: DNA
<213> ORGANISM: Homo sapiens

<400> SEQUENCE: 62 gccgccacc                                                                 9

<210> SEQ ID NO 63
<211> LENGTH: 37
<212> TYPE: DNA
<213> ORGANISM: Homo sapiens
<220> FEATURE:
<223> OTHER INFORMATION: Description of Artificial Sequence: DNA Primer

<400> SEQUENCE: 63
cagaaagctt gccgccacca tggattcaca ggcccag                                 37

<210> SEQ ID NO 64
<211> LENGTH: 6
<212> TYPE: PRT
<213> ORGANISM: Homo sapiens

<400> SEQUENCE: 64

Met Asp Ser Gln Ala Gln
 1               5

<210> SEQ ID NO 65
<211> LENGTH: 35
<212> TYPE: DNA
<213> ORGANISM: Homo sapiens
<220> FEATURE:
<223> OTHER INFORMATION: Description of Artificial Sequence: DNA Primer

<400> SEQUENCE: 65
ccgaggatcc actcacgttt cagctccagc ttggt                                   35

<210> SEQ ID NO 66
<211> LENGTH: 37
<212> TYPE: DNA
<213> ORGANISM: Homo sapiens
<220> FEATURE:
<223> OTHER INFORMATION: Description of Artificial Sequence: DNA Primer

<400> SEQUENCE: 66
cagaaagctt gccgccacca tgggatggag ctgggtc                                 37

<210> SEQ ID NO 67
<211> LENGTH: 6
<212> TYPE: PRT
<213> ORGANISM: Homo sapiens

<400> SEQUENCE: 67

Met Gly Trp Ser Trp Val
```

-continued

<210> SEQ ID NO 68
<211> LENGTH: 35
<212> TYPE: DNA
<213> ORGANISM: Homo sapiens
<220> FEATURE:
<223> OTHER INFORMATION: Description of Artificial Sequence: DNA Primer

<400> SEQUENCE: 68
ccgaggatcc actcacctga ggagacggtg actga                              35

<210> SEQ ID NO 69
<211> LENGTH: 36
<212> TYPE: DNA
<213> ORGANISM: Homo sapiens
<220> FEATURE:
<223> OTHER INFORMATION: Description of Artificial Sequence: DNA Primer

<400> SEQUENCE: 69
gtcatcacaa tgtctccgga ggaacctgga acccag                             36

<210> SEQ ID NO 70
<211> LENGTH: 29
<212> TYPE: DNA
<213> ORGANISM: Homo sapiens
<220> FEATURE:
<223> OTHER INFORMATION: Description of Artificial Sequence: DNA Primer

<400> SEQUENCE: 70
ctccggagac attgtgatga cccaatctc                                     29

<210> SEQ ID NO 71
<211> LENGTH: 45
<212> TYPE: DNA
<213> ORGANISM: Homo sapiens
<220> FEATURE:
<223> OTHER INFORMATION: Description of Artificial Sequence: DNA Primer

<400> SEQUENCE: 71
gaatataaaa ggctctgact ggacttgcag ttgatggtgg ccctc                   45

<210> SEQ ID NO 72
<211> LENGTH: 72
<212> TYPE: DNA
<213> ORGANISM: Homo sapiens
<220> FEATURE:
<223> OTHER INFORMATION: Description of Artificial Sequence: DNA Primer

<400> SEQUENCE: 72
cagtcagagc cttttatatt ctagaaatca aagaactac ttggcctggt atcagcagaa    60
accaggacag cc                                                       72

<210> SEQ ID NO 73
<211> LENGTH: 44
<212> TYPE: DNA
<213> ORGANISM: Homo sapiens
<220> FEATURE:
<223> OTHER INFORMATION: Description of Artificial Sequence: DNA Primer

<400> SEQUENCE: 73
accccagatt ccctagtgct agcccaaaag atgaggagtt tggg                    44

<210> SEQ ID NO 74
<211> LENGTH: 67

```
<212> TYPE: DNA
<213> ORGANISM: Homo sapiens
<220> FEATURE:
<223> OTHER INFORMATION: Description of Artificial Sequence: DNA Primer

<400> SEQUENCE: 74
tagcactagg gaatctgggg tacctgatag gttcagtggc agtgggtttg ggacagactt    60
caccctc                                                              67

<210> SEQ ID NO 75
<211> LENGTH: 53
<212> TYPE: DNA
<213> ORGANISM: Homo sapiens
<220> FEATURE:
<223> OTHER INFORMATION: Description of Artificial Sequence: DNA Primer

<400> SEQUENCE: 75
gtcccttgtc cgaacgtgag cggatagcta aatattgct gacagtaata aac            53

<210> SEQ ID NO 76
<211> LENGTH: 33
<212> TYPE: DNA
<213> ORGANISM: Homo sapiens
<220> FEATURE:
<223> OTHER INFORMATION: Description of Artificial Sequence: DNA Primer

<400> SEQUENCE: 76
gctcacgttc ggacaaggga ccaaggtgga aat                                 33

<210> SEQ ID NO 77
<211> LENGTH: 72
<212> TYPE: DNA
<213> ORGANISM: Homo sapiens
<220> FEATURE:
<223> OTHER INFORMATION: Description of Artificial Sequence: DNA Primer

<400> SEQUENCE: 77
cagtcagagc cttttatatt ctagaaatca aagaactac ttggcctggt tccagcagaa     60
accaggacag cc                                                        72

<210> SEQ ID NO 78
<211> LENGTH: 56
<212> TYPE: DNA
<213> ORGANISM: Homo sapiens
<220> FEATURE:
<223> OTHER INFORMATION: Description of Artificial Sequence: DNA Primer

<400> SEQUENCE: 78
tcccttgtcc gaacgtgagc ggatagctaa aatattgctg acagtcataa actgcc        56

<210> SEQ ID NO 79
<211> LENGTH: 34
<212> TYPE: DNA
<213> ORGANISM: Homo sapiens
<220> FEATURE:
<223> OTHER INFORMATION: Description of Artificial Sequence: DNA Primer

<400> SEQUENCE: 79
cccaaactcc tcatctattg ggctagcact aggg                                34

<210> SEQ ID NO 80
<211> LENGTH: 34
<212> TYPE: DNA
<213> ORGANISM: Homo sapiens
<220> FEATURE:
```

<223> OTHER INFORMATION: Description of Artificial Sequence: DNA Primer

<400> SEQUENCE: 80
ccctagtgct agcccaatag atgaggagtt tggg                          34

<210> SEQ ID NO 81
<211> LENGTH: 17
<212> TYPE: DNA
<213> ORGANISM: Homo sapiens
<220> FEATURE:
<223> OTHER INFORMATION: Description of Artificial Sequence: DNA Primer

<400> SEQUENCE: 81
tacgcaaacc gcctctc                                             17

<210> SEQ ID NO 82
<211> LENGTH: 18
<212> TYPE: DNA
<213> ORGANISM: Homo sapiens
<220> FEATURE:
<223> OTHER INFORMATION: Description of Artificial Sequence: DNA Primer

<400> SEQUENCE: 82
gagtgcacca tatgcggt                                            18

<210> SEQ ID NO 83
<211> LENGTH: 16
<212> TYPE: DNA
<213> ORGANISM: Homo sapiens
<220> FEATURE:
<223> OTHER INFORMATION: Description of Artificial Sequence: DNA Primer

<400> SEQUENCE: 83
aacagctatg accatg                                              16

<210> SEQ ID NO 84
<211> LENGTH: 17
<212> TYPE: DNA
<213> ORGANISM: Homo sapiens
<220> FEATURE:
<223> OTHER INFORMATION: Description of Artificial Sequence: DNA Primer

<400> SEQUENCE: 84
gttttcccag tcacgac                                             17

<210> SEQ ID NO 85
<211> LENGTH: 47
<212> TYPE: DNA
<213> ORGANISM: Homo sapiens
<220> FEATURE:
<223> OTHER INFORMATION: Description of Artificial Sequence: DNA Primer

<400> SEQUENCE: 85
gtgtattcag tgaaggtgta tctactagtt ttacagctga ctttcac            47

<210> SEQ ID NO 86
<211> LENGTH: 53
<212> TYPE: DNA
<213> ORGANISM: Homo sapiens
<220> FEATURE:
<223> OTHER INFORMATION: Description of Artificial Sequence: DNA Primer

<400> SEQUENCE: 86
tagtagatac accttcactg aatacaccat acactgggtt agacaggccc ctg     53

-continued

```
<210> SEQ ID NO 87
<211> LENGTH: 71
<212> TYPE: DNA
<213> ORGANISM: Homo sapiens
<220> FEATURE:
<223> OTHER INFORMATION: Description of Artificial Sequence: DNA Primer

<400> SEQUENCE: 87
cccttgaact tctggttgta gttaggaata ccattgttag gattaatacc tcctatccac      60
tccagccttt g                                                          71

<210> SEQ ID NO 88
<211> LENGTH: 71
<212> TYPE: DNA
<213> ORGANISM: Homo sapiens
<220> FEATURE:
<223> OTHER INFORMATION: Description of Artificial Sequence: DNA Primer

<400> SEQUENCE: 88
taactacaac cagaagttca agggccgggc caccttgacc gtaggcaagt ctgccagcac      60
cgcctacatg g                                                          71

<210> SEQ ID NO 89
<211> LENGTH: 63
<212> TYPE: DNA
<213> ORGANISM: Homo sapiens
<220> FEATURE:
<223> OTHER INFORMATION: Description of Artificial Sequence: DNA Primer

<400> SEQUENCE: 89
gcatggccct cgtcgtaacc ataggcgatt cttcttctgg cgcagtagta gactgcagtg      60
tcc                                                                   63

<210> SEQ ID NO 90
<211> LENGTH: 48
<212> TYPE: DNA
<213> ORGANISM: Homo sapiens
<220> FEATURE:
<223> OTHER INFORMATION: Description of Artificial Sequence: DNA Primer

<400> SEQUENCE: 90
ctatggttac gacgagggcc atgctatgga ctactggggt caaggaac                  48

<210> SEQ ID NO 91
<211> LENGTH: 71
<212> TYPE: DNA
<213> ORGANISM: Homo sapiens
<220> FEATURE:
<223> OTHER INFORMATION: Description of Artificial Sequence: DNA Primer

<400> SEQUENCE: 91
taactacaac cagaagttca agggccgggt caccatcacc gtagacacct ctgccagcac      60
cgcctacatg g                                                          71

<210> SEQ ID NO 92
<211> LENGTH: 27
<212> TYPE: DNA
<213> ORGANISM: Homo sapiens
<220> FEATURE:
<223> OTHER INFORMATION: Description of Artificial Sequence: DNA Primer

<400> SEQUENCE: 92
ggacactgca gtctacttct gcgccag                                         27
```

<210> SEQ ID NO 93
<211> LENGTH: 17
<212> TYPE: DNA
<213> ORGANISM: Homo sapiens
<220> FEATURE:
<223> OTHER INFORMATION: Description of Artificial Sequence: DNA Primer

<400> SEQUENCE: 93
tacgcaaacc gcctctc                                                          17

<210> SEQ ID NO 94
<211> LENGTH: 18
<212> TYPE: DNA
<213> ORGANISM: Homo sapiens
<220> FEATURE:
<223> OTHER INFORMATION: Description of Artificial Sequence: DNA Primer

<400> SEQUENCE: 94
gagtgcacca tatgcggt                                                         18

<210> SEQ ID NO 95
<211> LENGTH: 75
<212> TYPE: DNA
<213> ORGANISM: Homo sapiens
<220> FEATURE:
<223> OTHER INFORMATION: Description of Artificial Sequence: DNA Primer

<400> SEQUENCE: 95
cctttggcca ggggcctgtc taacccagtg tatggtgtat tcagtgaagg tgtatccact           60
agtttccact agttt                                                            75

<210> SEQ ID NO 96
<211> LENGTH: 28
<212> TYPE: DNA
<213> ORGANISM: Homo sapiens
<220> FEATURE:
<223> OTHER INFORMATION: Description of Artificial Sequence: DNA Primer

<400> SEQUENCE: 96
gtcaccgtcc ttgacacgcg tctcggga                                              28

<210> SEQ ID NO 97
<211> LENGTH: 17
<212> TYPE: DNA
<213> ORGANISM: Homo sapiens
<220> FEATURE:
<223> OTHER INFORMATION: Description of Artificial Sequence: DNA Primer

<400> SEQUENCE: 97
ttggaggagg gtgccag                                                          17

<210> SEQ ID NO 98
<211> LENGTH: 22
<212> TYPE: DNA
<213> ORGANISM: Homo sapiens
<220> FEATURE:
<223> OTHER INFORMATION: Description of Artificial Sequence: DNA Primer

<400> SEQUENCE: 98
gagacattgt gacccaatct cc                                                    22

<210> SEQ ID NO 99
<211> LENGTH: 25
<212> TYPE: DNA
<213> ORGANISM: Homo sapiens
<220> FEATURE:
<223> OTHER INFORMATION: Description of Artificial Sequence: DNA Primer

<400> SEQUENCE: 99
gacagtcata aactgccaca tcttc                                          25

<210> SEQ ID NO 100
<211> LENGTH: 23
<212> TYPE: DNA
<213> ORGANISM: Homo sapiens
<220> FEATURE:
<223> OTHER INFORMATION: Description of Artificial Sequence: DNA Primer

<400> SEQUENCE: 100
ttgacacgcg tctcgggaag ctt                                            23

<210> SEQ ID NO 101
<211> LENGTH: 22
<212> TYPE: DNA
<213> ORGANISM: Homo sapiens
<220> FEATURE:
<223> OTHER INFORMATION: Description of Artificial Sequence: DNA Primer

<400> SEQUENCE: 101
ggcgcagagg atccactcac ct                                             22

<210> SEQ ID NO 102
<211> LENGTH: 339
<212> TYPE: DNA
<213> ORGANISM: Homo sapiens

<400> SEQUENCE: 102
gacattgtga tgacccaatc tccagactct ttggctgtgt ctctagggga gagggccacc     60
atcaactgca agtccagtca gagccttttta tattctagaa atcaaaagaa ctacttggcc   120
tggttccagc agaaaccagg acagccaccc aaactcctca tcttttgggc tagcactagg   180
gaatctgggg tacctgatag gttcagtggc agtgggtttg ggacagactt caccctcacc   240
attagcagcc tgcaggctga agatgtggca gtttatgact gtcaacaata ttttagctat   300
ccgctcacgt tcggacaagg gaccaaggtg gaaataaaa                           339

<210> SEQ ID NO 103
<211> LENGTH: 339
<212> TYPE: DNA
<213> ORGANISM: Homo sapiens

<400> SEQUENCE: 103
gacattgtga tgacccaatc tccagactct ttggctgtgt ctctagggga gagggccacc     60
atcaactgca agtccagtca gagccttttta tattctagaa atcaaaagaa ctacttggcc   120
tggtatcagc agaaaccagg acagccaccc aaactcctca tctattgggc tagcactagg   180
gaatctgggg tacctgatag gttcagtggc agtgggtttg ggacagactt caccctcacc   240
attagcagcc tgcaggctga agatgtggca gtttattact gtcagcaata ttttagctat   300
ccgctcacgt tcggacaagg gaccaaggtg gaaataaaa                           339

<210> SEQ ID NO 104
<211> LENGTH: 372
<212> TYPE: DNA
<213> ORGANISM: Homo sapiens

<400> SEQUENCE: 104

-continued

```
caggtgcaac tagtgcagtc cggcgccgaa gtgaagaaac ccggtgcttc cgtgaaagtc      60
agctgtaaaa ctagtagata caccttcact gaatacacca tacactgggt tagacaggcc     120
cctggccaaa ggctggagtg gataggaggt attaatccta acaatggtat tcctaactac     180
aaccagaagt tcaagggccg ggccaccttg accgtaggca agtctgccag caccgcctac     240
atggaactgt ccagcctgcg ctccgaggac actgcagtct acttctgcgc cagaagaaga     300
atcgcctatg gttacgacga gggccatgct atggactact ggggtcaagg aacccttgtc     360
accgtctcct ca                                                         372
```

<210> SEQ ID NO 105
<211> LENGTH: 372
<212> TYPE: DNA
<213> ORGANISM: Homo sapiens

<400> SEQUENCE: 105

```
caggtgcaac tagtgcagtc cggcgccgaa gtgaagaaac ccggtgcttc cgtgaaagtc      60
agctgtaaaa ctagtagata caccttcact gaatacacca tacactgggt tagacaggcc     120
cctggccaaa ggctggagtg gataggaggt attaatccta acaatggtat tcctaactac     180
aaccagaagt tcaagggccg ggtcaccatc accgtagaca cctctgccag caccgcctac     240
atggaactgt ccagcctgcg ctccgaggac actgcagtct actactgcgc cagaagaaga     300
atcgcctatg gttacgacga gggccatgct atggactact ggggtcaagg aacccttgtc     360
accgtctcct ca                                                         372
```

<210> SEQ ID NO 106
<211> LENGTH: 372
<212> TYPE: DNA
<213> ORGANISM: Homo sapiens

<400> SEQUENCE: 106

```
caggtgcaac tagtgcagtc cggcgccgaa gtgaagaaac ccggtgcttc cgtgaaagtc      60
agctgtaaaa ctagtagata caccttcact gaatacacca tacactgggt tagacaggcc     120
cctggccaaa ggctggagtg gataggaggt attaatccta acaatggtat tcctaactac     180
aaccagaagt tcaagggccg ggtcaccatc accgtagaca cctctgccag caccgcctac     240
atggaactgt ccagcctgcg ctccgaggac actgcagtct acttctgcgc cagaagaaga     300
atcgcctatg gttacgacga gggccatgct atggactact ggggtcaagg aacccttgtc     360
accgtctcct ca                                                         372
```

<210> SEQ ID NO 107
<211> LENGTH: 372
<212> TYPE: DNA
<213> ORGANISM: Homo sapiens

<400> SEQUENCE: 107

```
caggtgcaac tagtgcagtc cggcgccgaa gtgaagaaac ccggtgcttc cgtgaaagtc      60
agctgtaaaa ctagtggata caccttcact gaatacacca tacactgggt tagacaggcc     120
cctggccaaa ggctggagtg gataggaggt attaatccta acaatggtat tcctaactac     180
aaccagaagt tcaagggccg ggtcaccatc accgtagaca cctctgccag caccgcctac     240
atggaactgt ccagcctgcg ctccgaggac actgcagtct actactgcgc cagaagaaga     300
atcgcctatg gttacgacga gggccatgct atggactact ggggtcaagg aacccttgtc     360
accgtctcct ca                                                         372
```

<210> SEQ ID NO 108
<211> LENGTH: 124
<212> TYPE: PRT
<213> ORGANISM: Homo sapiens

<400> SEQUENCE: 108

```
Gln Val Gln Leu Val Gln Ser Gly Ala Glu Val Lys Lys Pro Gly Ala
 1               5                  10                  15

Ser Val Lys Val Ser Cys Lys Thr Ser Arg Tyr Thr Phe Thr Glu Tyr
            20                  25                  30

Thr Ile His Trp Val Arg Gln Ala Pro Gly Gln Arg Leu Glu Trp Ile
        35                  40                  45

Gly Gly Ile Asn Pro Asn Asn Gly Ile Pro Asn Tyr Asn Gln Lys Phe
    50                  55                  60

Lys Gly Arg Val Thr Ile Thr Val Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Ala Arg Arg Arg Ile Ala Tyr Gly Tyr Asp Glu Gly His Ala Met Asp
            100                 105                 110

Tyr Trp Gly Gln Gly Thr Leu Val Thr Val Ser Ser
        115                 120
```